(12) United States Patent
Kufe

(10) Patent No.: US 8,809,002 B2
(45) Date of Patent: Aug. 19, 2014

(54) MUC1, CASPASE-8, AND DED-CONTAINING PROTEINS

(75) Inventor: Donald W. Kufe, Wellesley, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 636 days.

(21) Appl. No.: 13/003,539

(22) PCT Filed: Jul. 9, 2009

(86) PCT No.: PCT/US2009/050118
§ 371 (c)(1),
(2), (4) Date: Apr. 25, 2011

(87) PCT Pub. No.: WO2010/006177
PCT Pub. Date: Jan. 14, 2010

(65) Prior Publication Data
US 2011/0207656 A1 Aug. 25, 2011

Related U.S. Application Data

(60) Provisional application No. 61/079,793, filed on Jul. 10, 2008, provisional application No. 61/082,120, filed on Jul. 18, 2008.

(51) Int. Cl.
*G01N 33/53* (2006.01)
*A61K 38/00* (2006.01)
*C07K 5/00* (2006.01)
*C07K 7/00* (2006.01)
*C07K 16/00* (2006.01)
*C07K 17/00* (2006.01)

(52) U.S. Cl.
USPC ............. 435/7.8; 530/324; 530/325; 530/326

(58) Field of Classification Search
CPC ............................................ G01N 2333/4725
See application file for complete search history.

(56) References Cited

U.S. PATENT DOCUMENTS

| | | |
|---|---|---|
| 6,586,571 B1 | 7/2003 | Wallach et al. ............... 530/350 |
| 2004/0229260 A1 | 11/2004 | Wallach et al. .................... 435/6 |
| 2007/0202134 A1 | 8/2007 | Kufe et al. ................. 424/277.1 |

OTHER PUBLICATIONS

Agata et al. MUC1 Oncoprotein Blocks Death Receptor-Mediated Apoptosis by Inhibiting Recruitment of Caspase-8. Cancer Research, 2008, vol. 68, pp. 6136-6144.*

Chaturvedi et al. Augmentation of Fas ligand-induced apoptosis by MUC1 mucin. International JOurnal of Oncology, 2005, vol. 26, pp. 1169-1176.* de Jong et al. Receptor-ligand binding assays: Technologies and Applications. Journal of Chromatography B, 2005, vol. 829, pp. 1-25.*

Agata et al., MUC1 Oncoprotein Blocks Death Receptor-Mediated Apoptosis by Inhibiting Recruitment of Caspase-8, Cancer Res. 68(15):6136-6144 (Aug. 2008).

Micheau et al., The Long Form of FLIP Is an Activator of Caspase-8 at the Fas Death-inducing Signaling Complex, J. Biological Chemistry, 277(47):45162-45171 (Nov. 2002).

Wei et al., Human Mucin 1 Oncoprotein Represses Transcription of the p53 Tumor Suppressor Gene, Cancer Res., 67(4):1853-1858 (Feb. 2007).

\* cited by examiner

*Primary Examiner* — Marcela M Cordero Garcia
(74) *Attorney, Agent, or Firm* — Fish & Richardson P.C.

(57) ABSTRACT

The disclosure features a variety of compositions and methods for modulating an interaction between MUC1 and caspase-8 and/or an interaction between MUC1 and a DED-containing protein (e.g., an anti-apoptotic DED-containing protein or a pro-apoptotic DED-containing protein). Such methods and compositions are useful for the treatment or prevention of e.g., a variety of pathological disorders characterized by elevated or decreased levels of apoptosis. Moreover, the compositions and methods are also useful to identify, design, and generate compounds that modulate the interactions. The compounds and/or pharmaceutical compositions containing the compounds can be used in the treatment of disease.

10 Claims, 22 Drawing Sheets

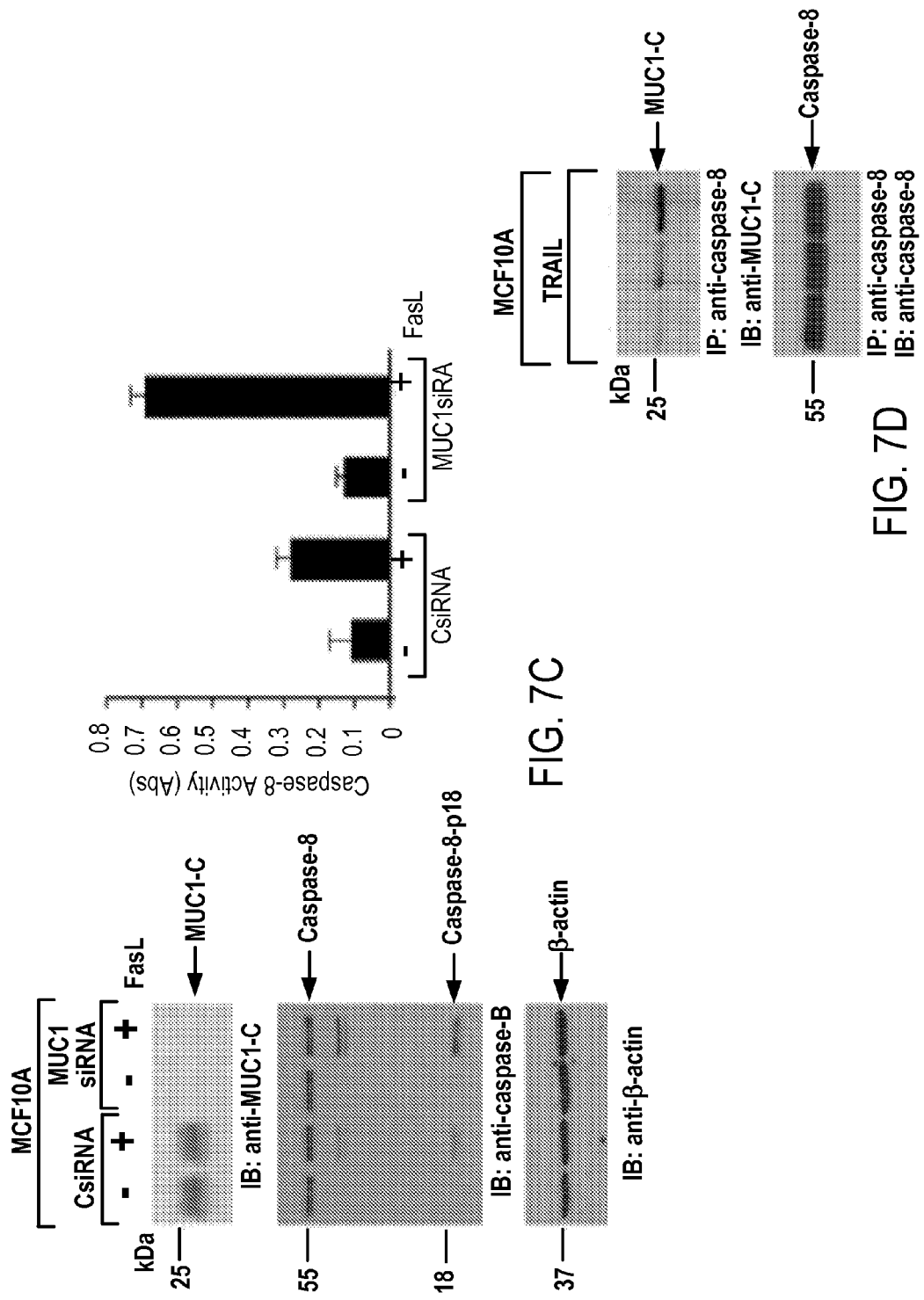

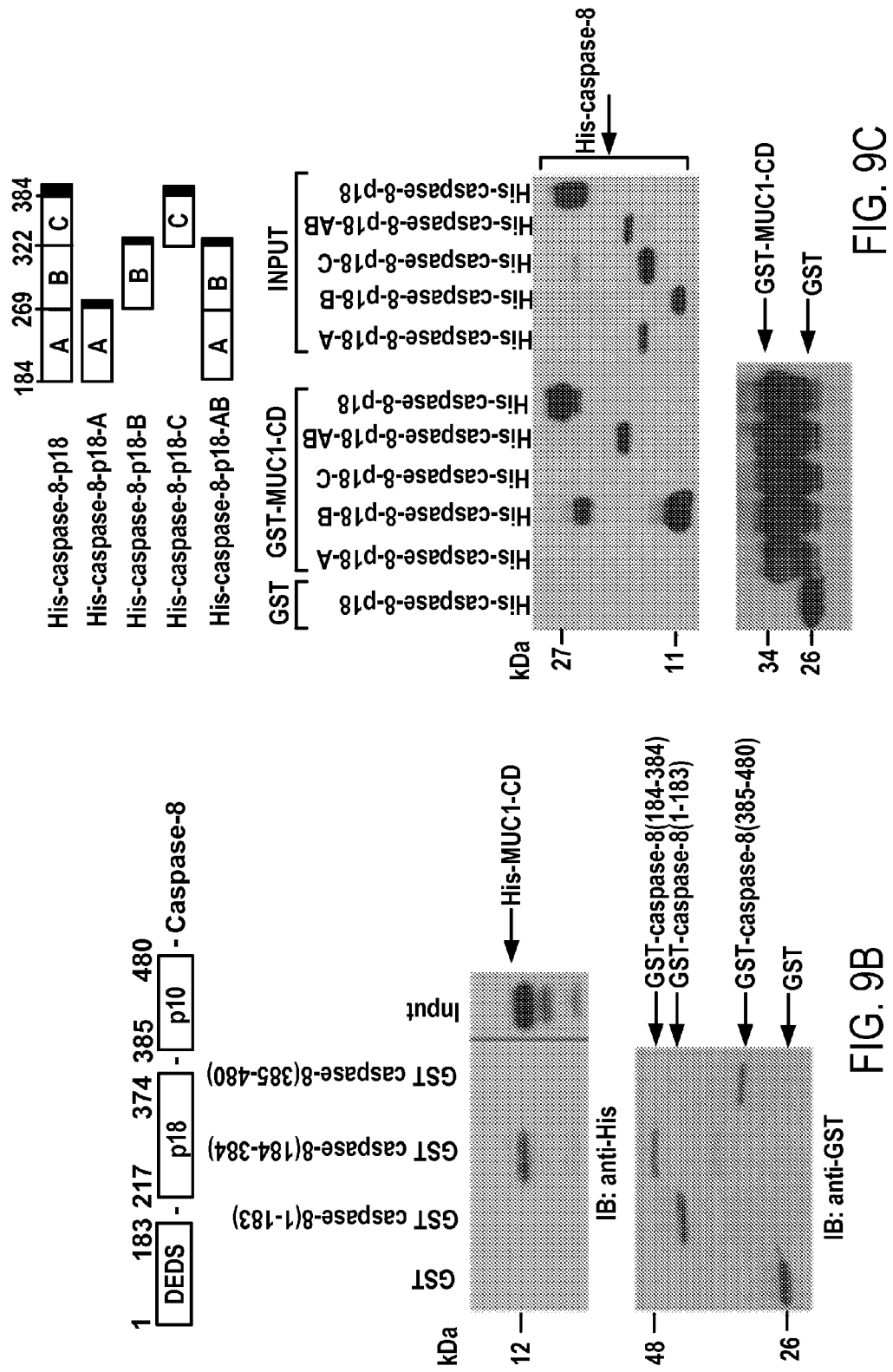

Caspase-8
270 ──────────────────────────────────────── 322
KLHSIRDRNGTHLDAGALTTTFEELHFEIKPHHDCTVEQIYEILKIYQLMDHS

MUC1, CASPASE-8, AND DED-CONTAINING PROTEINS

This application is a U.S. National Phase Application of International Application No. PCT/US2009/050118, filed Jul. 9, 2009, which claims priority of U.S. Provisional Application No. 61/082,120, filed Jul. 18, 2008, and U.S. Provisional Application No. 61/079,793, filed Jul. 10, 2008. The disclosures of International Application No. PCT/US2009/050118, U.S. Provisional Application No. 61/082,120, and U.S. Provisional Application No. 61/079,793 are incorporated herein by reference in their entirety.

STATEMENT REGARDING FEDERALLY SPONSORED RESEARCH OR DEVELOPMENT

The research described in this application was supported by a grant nos. CA100707, CA98628, and CA97098, each awarded by the National Cancer Institute of the National Institutes of Health of the United States of America. Thus, the government has certain rights in this invention.

SUMMARY

This disclosure relates to the role of MUC1 in death receptor-mediated apoptosis. The findings described herein demonstrate, inter alia, that MUC1 blocks activation of caspase-8 and apoptosis in cancer cells exposed to tumor necrosis factor alpha (TNFα), TRAIL, and Fas ligand (FasL). Moreover, the findings also demonstrate that MUC1: (i) interacts with caspase-8 and the DED domain of Fas-associated death domain (FADD) in vivo and in vitro; (ii) competes with caspase-8 for binding to FADD; and (iii) inhibits the recruitment of caspase-8 to the death-inducing signaling complex (DISC). Thus, the disclosure supports a conclusion that inhibition of MUC1-caspase-8 and/or MUC1-FADD interactions could be beneficial in treating cancers. Since the caspase-8 and MUC1 pathways are implicated not only in regulating cancer cell growth (and viability) but also regulation of the growth and viability of inflammatory cells (e.g., immune cells), inhibition of MUC1-caspase-8 or MUC1-FADD interactions could also be useful in the treatment of inflammatory conditions (e.g., autoimmune disorders or any of the other inflammatory conditions described herein). Moreover, in pathological conditions characterized by increased levels of apoptosis (e.g., neurological disorders or ischemic disorders), enhancement of the interaction of MUC1 and caspase-8 and/or MUC1 and FADD could be beneficial to treat such conditions. A variety of compositions and methods are described below for not only modulating interactions between MUC1 and caspase-8 and/or MUC1 and FADD, but also for identifying compounds that modulate the interactions.

In one aspect, the disclosure features a method of identifying a compound that modulates (e.g., inhibits or enhances) the binding of MUC1 to caspase-8. The method includes the steps of: contacting a MUC1 reagent with a caspase-8 reagent in the presence of a candidate compound; and determining whether the candidate compound modulates binding of the MUC1 reagent to the caspase-8 reagent. The caspase-8 reagent can comprise or be a full-length, unprocessed caspase-8. The caspase-8 can contain, or be, the amino acid sequence depicted in SEQ ID NO:5. The caspase-8 reagent can contain, or be, the p18 subunit of caspase-8 such as the human caspase-8 p18 unit having the amino acid sequence depicted in SEQ ID NO:6 or amino acids 270-322 of caspase-8 (e.g., SEQ ID NO:27 or SEQ ID NO:28).

In another aspect, the disclosure features a method for identifying a compound that modulates (e.g., inhibits or enhances) the binding of MUC1 to a DED-containing protein, which method includes the steps of: contacting a MUC1 reagent with a DED-containing protein reagent in the presence of a candidate compound; and determining whether the candidate compound modulates binding of the MUC1 reagent to the DED-containing protein reagent. The DED-containing protein reagent can be, or contain, FADD or a DED-containing fragment thereof. The DED-containing fragment can contain, or be, SEQ ID NO:8. FADD can be, for example, the amino acid sequence depicted in SEQ ID NO:7. The DED-containing protein reagent can contain a protein selected from the group consisting of caspase-10, DEDD, BAR, DEDD2, Hip-1, BAP31, c-FLIP$_L$, c-FLIP$_S$, Hippi, and a DED-containing fragment of any of the foregoing. The DED-containing protein reagent can be or contain, e.g., a mammalian (e.g., a rat, mouse, non-human primate, or human) protein.

In some embodiments of any of the methods described herein, the MUC1 reagent can comprise the cytoplasmic domain of MUC1. The cytoplasmic domain of MUC1 can be, for example, the amino acid sequence depicted in SEQ ID NO: 2 (MUC1-CD). The MUC1 reagent can comprise, or be, amino acids 1-20 of the MUC1-CD (SEQ ID NO:3) or amino acids 46-72 of the MUC1-CD (SEQ ID NO:4).

In some embodiments of any of the methods described herein, the modulation is inhibition. In some embodiments, the modulation is enhancement.

In some embodiments of any of the methods described herein, the contacting and/or determining can occur in a cell.

In another aspect, the disclosure features a method of generating a compound that modulates the interaction between MUC1 and caspase-8. The method includes the steps of: providing a three-dimensional structure of a molecule or a molecular complex comprising: (a) the cytoplasmic domain of MUC1 or caspase-8-binding fragment thereof; (b) a molecule comprising caspase-8 or a MUC1-binding fragment thereof; or (c) a molecular complex comprising (a) and (b); designing, based on the three-dimensional structure, a compound comprising a region that inhibits the interaction between MUC1 and caspase-8; and producing the compound. The caspase-8 can be, or contain, a full-length, unprocessed caspase-8 such as full-length, unprocessed human caspase-8 (SEQ ID NO:5). The caspase-8 can comprise the p18 subunit of caspase-8 such as the human caspase-8 p18 unit having the amino acid sequence depicted in SEQ ID NO:6 or amino acids 270-322 of caspase-8 (e.g., SEQ ID NO:27 or SEQ ID NO:28).

In yet another aspect, the disclosure features a method of generating a compound that modulates the interaction between MUC1 and a DED-containing protein. The method includes the steps of: providing a three-dimensional structure of a molecule or a molecular complex comprising: (a) the cytoplasmic domain of MUC1 or a DED-binding fragment thereof; (b) a molecule comprising DED-containing protein or a MUC1-binding fragment thereof; or (c) a molecular complex comprising (a) and (b); designing, based on the three-dimensional structure, a compound comprising a region that inhibits the interaction between MUC1 and the DED-containing protein; and producing the compound. The DED-containing protein can comprise, or be, FADD or a DED-containing fragment thereof. The DED-containing fragment can comprise, or be, SEQ ID NO:8. FADD can be, for example, the human amino acid sequence depicted in SEQ ID NO:7. The DED-containing protein can be a protein selected from the group consisting of caspase-10, DEDD, BAR, DEDD2, Hip-1, BAP31, c-FLIP$_L$, c-FLIP$_S$, Hippi, and a DED-containing fragment of any of the foregoing. The DED-containing protein can be a mammalian protein such as a human protein.

In some embodiments of any of the methods described herein, the caspase-8-binding fragment can comprise the cytoplasmic domain of MUC1. The cytoplasmic domain of MUC1 can be, for example, the amino acid sequence depicted in SEQ ID NO: 2. The caspase-8-binding fragment can comprise, or be, amino acids 1-20 of the MUC1-CD (SEQ ID NO:3) or amino acids 46-72 of the MUC1-CD (e.g., SEQ ID NO:4).

In yet another aspect, the disclosure features a compound identified by any of the methods described herein and/or a pharmaceutical composition comprising the compound and a pharmaceutically acceptable carrier.

In another aspect, the disclosure features a process of manufacturing a compound. The process includes the steps of performing any of the methods described herein; and after determining that a candidate compound modulates the interaction between the MUC1 reagent and the caspase-8 reagent, manufacturing the candidate compound or after determining that a candidate compound inhibits the interaction between the MUC1 reagent and the DED-containing protein reagent, manufacturing the candidate compound.

In yet another aspect, the disclosure features an in vitro method of modulating an interaction between MUC1 and caspase-8. The method includes the steps of identifying a cell as one expressing one or both of caspase-8 and MUC1; and culturing the cell with an effective amount of a compound that modulates an interaction between MUC1 and caspase-8.

In another aspect, the disclosure features an in vitro method of modulating an interaction between MUC1 and a DED-containing protein such as FADD or any of the DED-containing proteins described herein. The method includes the steps of identifying a cell as one expressing one or both of a DED-containing protein and MUC1; and culturing the cell with an effective amount of a compound that modulates an interaction between MUC1 and the DED-containing protein.

In another aspect, the disclosure features an in vivo method of inhibiting an interaction between MUC1 and caspase-8, which method includes the steps of providing a subject having, or suspected of having, a cancer comprising one or more cells expressing one or both of caspase-8 and MUC1; and delivering to the subject an effective amount of a compound that inhibits an interaction between MUC1 and caspase-8.

In another aspect, the disclosure features an in vivo method of inhibiting an interaction between MUC1 and a pro-apoptotic DED-containing protein. The method includes the steps of providing a subject having, or suspected of having, a cancer comprising one or more cells expressing one or both of MUC1 and a pro-apoptotic DED-containing protein; and delivering to the subject an effective amount of a compound that inhibits an interaction between MUC1 and the pro-apoptotic DED-containing protein. Pro-apoptotic DED-containing proteins include, e.g., FADD, caspase-10, DEDD, Hip-1, Hippi, and BAP31.

In another aspect, the disclosure features an in vivo method of activating caspase-8, which method includes the steps of providing a subject having, or suspected of having, a cancer comprising one or more cells expressing one or both of MUC1 and caspase-8; and delivering to the subject an effective amount of a compound that activates caspase-8. The compound can be, e.g., FADD.

In another aspect, the disclosure features an in vivo method of enhancing an interaction between MUC1 and an anti-apoptotic DED-containing protein, which includes the steps of providing a subject having, or suspected of having, a cancer comprising one or more cells expressing one or both of MUC1 and an anti-apoptotic DED-containing protein; and delivering to the subject an effective amount of a compound that enhances an interaction between MUC1 and the anti-apoptotic DED-containing protein. Anti-apoptotic DED-containing proteins include, e.g., DEDD2, c-FLIP (long and short), PEA-15, and BAR.

In yet another aspect, the disclosure features an in vivo method of inhibiting an interaction between MUC1 and caspase-8. The method includes the steps of providing a subject having, or suspected of having, an inflammatory condition mediated by one or more cells expressing one or both of caspase-8 and MUC1; and delivering to the subject an effective amount of a compound that inhibits an interaction between MUC1 and caspase-8.

In another aspect, the disclosure features an in vivo method of inhibiting an interaction between MUC1 and a pro-apoptotic DED-containing protein. The method includes the steps of providing a subject having, or suspected of having, an inflammatory condition mediated by one or more cells expressing one or both of MUC1 and a pro-apoptotic DED-containing protein; and delivering to the subject an effective amount of a compound that inhibits an interaction between MUC1 and the pro-apoptotic DED-containing protein.

In another aspect, the disclosure features an in vivo method of enhancing an interaction between MUC1 and an anti-apoptotic DED-containing protein, the method comprising: providing a subject having, or suspected of having, an inflammatory condition mediated by one or more cells expressing one or both of MUC1 and an anti-apoptotic DED-containing protein; and delivering to the subject an effective amount of a compound that enhances an interaction between MUC1 and the anti-apoptotic DED-containing protein.

In another aspect, the disclosure features a method for enhancing cell viability, which method includes delivering to a cell population an effective amount of a compound that enhances an interaction between MUC1 and caspase-8 to thereby enhance the viability of the cell population, wherein a plurality of cells of the cell population expresses one or both of MUC1 and caspase-8.

In another aspect, the disclosure features a method for enhancing cell viability, the method comprising delivering to a cell population an effective amount of a compound that enhances an interaction between MUC1 and a pro-apoptotic DED-containing protein to thereby enhance the viability of the cell population, wherein a plurality of cells of the cell population expresses one or both of MUC1 and the pro-apoptotic DED-containing protein.

In another aspect, the disclosure features a method for enhancing cell viability, the method comprising delivering to a cell population an effective amount of a compound that inhibits an interaction between MUC1 and an anti-apoptotic DED-containing protein to thereby enhance the viability of the cell population, wherein a plurality of cells of the cell population expresses one or both of MUC1 and the anti-apoptotic DED-containing protein.

In some embodiments of any of the methods described herein, the cell population is in a tissue or organ. The cell population can be in a neuronal tissue or a muscle tissue. For example, the cell population can be in heart tissue, brain tissue, or spinal cord tissue. In some embodiments, the cell population can be in a subject (e.g., a mammal such as a human). The subject can be one who has, is suspected of having, or is at risk for developing a neurodegenerative disorder such as, but not limited to, Alzheimer's disease, Parkinson's disease, Huntingdon's disease, multiple sclerosis, amyotrophic lateral sclerosis (ALS), spinobulbar atrophy, denervation atrophy, spinal muscular dystrophy (SMA), pigmentary degeneration of the retina and glaucoma, cerebellar degeneration and neonatal jaundice, otosclerosis, stroke, dementia, or successive delayed neuronal death (DND). The subject can be one who has, is suspected of having, or is at risk for developing an ischemic disorder such as, but not limited to, a stroke, ischemic acute renal failure, intestinal ischemia, myocardial infarction, myocardial ischemia and disorder after reperfusion, liver ischemia, brain ischemia, and ischemia retinae.

In yet another aspect, the disclosure features a method for treating a pathological condition characterized by an elevated level of apoptosis, which method includes the step of delivering to a subject having, suspected of having, or at risk for developing a pathological condition characterized by an elevated level of apoptosis an effective amount of a compound that enhances an interaction between MUC1 and caspase-8.

In another aspect, the disclosure features a method for treating a pathological condition characterized by an elevated level of apoptosis. The method includes the step of delivering to a subject having, suspected of having, or at risk for developing a pathological condition characterized by an elevated level of apoptosis an effective amount of a compound that enhances an interaction between MUC1 and a pro-apoptotic DED-containing protein.

In another aspect, the disclosure features a method for treating a pathological condition characterized by an elevated level of apoptosis, the method comprising delivering to a subject having, suspected of having, or at risk for developing a pathological condition characterized by an elevated level of apoptosis an effective amount of a compound that inhibits an interaction between MUC1 and an anti-apoptotic DED-containing protein.

In some embodiments of any of the methods described herein, the pathological condition characterized by an elevated level of apoptosis is a neurodegenerative disorder or an ischemic disorder.

In some embodiments, any of the methods described herein can include the step of, prior to administering the compound, determining that the subject has, is suspected of having, or is at risk for developing a pathological condition characterized by an elevated level of apoptosis.

In another aspect, the disclosure features a method for treating a pathological condition characterized by a decreased level of apoptosis. The method includes the step of delivering to a subject having, suspected of having, or at risk for developing a pathological condition characterized by a decreased level of apoptosis an effective amount of a compound that inhibits an interaction between MUC1 and caspase-8.

In another aspect, the disclosure features a method for treating a pathological condition characterized by a decreased level of apoptosis, which method includes the step of delivering to a subject having, suspected of having, or at risk for developing a pathological condition characterized by a decreased level of apoptosis in a cell population an effective amount of a compound that activates caspase-8, wherein a plurality of cells of the cell population expresses MUC1.

In another aspect, the disclosure features a method for treating a pathological condition characterized by a decreased level of apoptosis. The method includes the step of delivering to a subject having, suspected of having, or at risk for developing a pathological condition characterized by a decreased level of apoptosis a compound in an amount effective to inhibit an interaction between MUC1 and a pro-apoptotic DED-containing protein.

In another aspect, the disclosure features a method for treating a pathological condition characterized by a decreased level of apoptosis. The method includes the step of delivering to a subject having, suspected of having, or at risk for developing a pathological condition characterized by a decreased level of apoptosis a compound in an amount effective to enhance an interaction between MUC1 and an anti-apoptotic DED-containing protein.

In some embodiments, the pathological condition characterized by a decreased level of apoptosis can be, e.g., a cancer, an inflammatory disorder, or a microbial infection (e.g., infection by a virus encoding a protein that inhibits apoptosis such as a adenoviruses, Epstein Barr virus, or pox viruses), or a developmental disorder such as a morphogenic disorder (e.g., syndactyly).

In some embodiments of the methods described herein, the subject can be a mammal such as a human, a non-human primate (e.g., monkeys, baboons, or chimpanzees), a horse, cow, pig, sheep, goat, dog, cat, rabbit, guinea pig, gerbil, hamster, rat, or mouse.

In some embodiments of any of the methods described herein, the compound can inhibit or increase the expression of MUC1, caspase-8, or DED-containing protein. Expression can be protein or mRNA expression.

In some embodiments of any of the methods described herein, the cell can be a cancer cell selected from the group consisting of a lung cancer cell, a breast cancer cell, a colon cancer cell, a pancreatic cancer cell, a renal cancer cell, a stomach cancer cell, a liver cancer cell, a bone cancer cell, a hematological cancer cell, a neural tissue cancer cell, a melanoma cell, a thyroid cancer cell, an ovarian cancer cell, a testicular cancer cell, a prostate cancer cell, a cervical cancer cell, a vaginal cancer cell, or a bladder cancer cell.

In some embodiments of any of the methods described herein, the cancer can be, e.g., lung cancer, breast cancer, colon cancer, pancreatic cancer, renal cancer, stomach cancer, liver cancer, bone cancer, hematological cancer, neural tissue cancer, melanoma, thyroid cancer, ovarian cancer, testicular cancer, prostate cancer, cervical cancer, vaginal cancer, or bladder cancer.

In some embodiments, the inflammatory condition can be an autoimmune disease such as, but not limited to, multiple sclerosis (MS), rheumatoid arthritis (RA), insulin-dependent diabetes mellitus (IDDM), or muscular dystrophy (MD). In some embodiments of any of the method described herein, the inflammatory condition can be selected from the group consisting of: osteoarthritis, spondyloarthrophathies, POEMS syndrome, Crohn's disease, multicentric Castleman's disease, systemic lupus erythematosus, dermatomyositis, polymyositis, Guillain Barre syndrome, Wegener's granulomatosus, polyarteritis nodosa, polymyalgia rheumatica, temporal arteritis, Sjogren's syndrome, Bechet's disease, Churg-Strauss syndrome, ulcerative colitis, and Takayasu's arteritis.

In some embodiments, any of the methods described herein can include administering to the subject one or more additional therapeutic agents. The one or more additional therapeutic agents can comprise, or be, one or more chemotherapeutic agents, one or more forms of ionizing radiation, one or more immunotherapy agents, or one or more hyperthermotherapy agents. The one or more forms of ionizing radiation can be gamma-irradiation, X-irradiation, or beta-irradiation. The one or more chemotherapeutic agents can be selected from the group consisting of cisplatin, carboplatin, procarbazine, mechlorethamine, cyclophosphamide, camptothecin, adriamycin, ifosfamide, melphalan, chlorambucil, bisulfan, nitrosurea, dactinomycin, daunorubicin, doxorubicin, blcomycin, plicomycin, mitomycin, ctoposide, vcrampil, podophyllotoxin, tamoxifen, taxol, transplatinum, 5-flurouracil, vincristin, vinblastin, methotrexate, and an analog of any of the aforementioned. In some embodiments, e.g., in embodiments where the subject has, is at risk of developing, or is suspected of having, an inflammatory disorders, the one or more therapeutic agents can be a non-steroidal anti-inflammatory drug (NSAID), a disease-modifying anti-rheumatic drug (DMARD), a biological response modifier, or a corticosteroid. The biological response modifier can be an anti-TNF agent. The anti-TNF agent can be, or contain, a soluble TNFα receptor or an antibody specific for TNFα. The antibody specific for TNFα can be, e.g., adulimumab, infliximab, or etanercept.

In some embodiments of any of the methods described herein, the compound can be, e.g., an aptamer, an siRNA, an miRNA, a small molecule, an antibody, an antibody fragment, a polypeptide, or a peptidomimetic.

In some embodiments of any of the methods described herein, the delivery can include administering to a subject a compound identified by any of the methods described herein or a pharmaceutical composition containing the compound.

In some embodiments, any of the methods described herein can include the step of identifying a subject as one who has, is suspected of having, or at risk of developing a pathological condition characterized by an elevated level of apoptosis or a pathological condition characterized by an decreased level of apoptosis.

In some embodiments, any of the methods described herein can include the step of, after delivering the compound to the subject, determining whether modulation (e.g., inhibition or enhancement) occurred.

In some embodiments, any of the methods described herein can include the step of, after delivering the compound to the subject, monitoring the subject for an improvement in one or more symptoms of a condition being treated.

In some embodiments of any of the methods described herein, the delivery can include, where the compound is a polypeptide, administering to the subject a nucleic acid comprising a nucleotide sequence encoding the polypeptide, the nucleotide sequence being operably-linked to a transcriptional regulatory sequence. The nucleic acid can be in a recombinant cell transfected with the nucleic acid and secreting the polypeptide. The recombinant cell can be a transfected cell, or the progeny of a transfected cell, made by transfecting a cell derived from the subject.

In yet another aspect, the disclosure features an isolated peptide consisting of an amino acid sequence that contains, or consists of, amino acids 1-20 of the MUC1-CD. The isolated polypeptide can be at least 80 (e.g., 81, 82, 83, 84, 85, 86, 87, 88, 89, 90, 91, 92, 93, 94, 95, 96, 97, 98, 99, or 100) % identical to SEQ ID NO:3 (amino acids 1-20 of human MUC1-CD). The peptide can inhibit an interaction between MUC1 and caspase-8.

In yet another aspect, the disclosure features an isolated peptide consisting of an amino acid sequence that contains, or consists of, amino acids 270-322 of human caspase-8. The isolated polypeptide can be at least 80 (e.g., 81, 82, 83, 84, 85, 86, 87, 88, 89, 90, 91, 92, 93, 94, 95, 96, 97, 98, 99, or 100) % identical to the amino acids 270-322 of human caspase-8 (e.g., to SEQ ID NO:27 or to SEQ ID NO:2). The peptide can inhibit an interaction between MUC1 and caspase-8.

In another aspect, the disclosure features an isolated peptide comprising: a first amino acid sequence consisting of a peptide that (i) contains, or consists of, amino acids 1-20 of the MUC1-CD or (ii) that is at least 80 (e.g., 81, 82, 83, 84, 85, 86, 87, 88, 89, 90, 91, 92, 93, 94, 95, 96, 97, 98, 99, or 100) % identical to SEQ ID NO:3 (amino acids 1-20 of human MUC1-CD); and a second amino acid sequence that is heterologous to the first amino acid sequence.

In another aspect, the disclosure features an isolated peptide comprising: a first amino acid sequence consisting of a peptide that: (i) contains, or consists of, amino acids 270-322 of human caspase-8 or to SEQ ID NO:27 or to SEQ ID NO:28; or (ii) that is at least 80 (e.g., 81, 82, 83, 84, 85, 86, 87, 88, 89, 90, 91, 92, 93, 94, 95, 96, 97, 98, 99, or 100) % identical to the amino acids 270-322 of human caspase-8 (or to SEQ ID NO:27 or to SEQ ID NO:28); and a second amino acid sequence that is heterologous to the first amino acid sequence.

In another aspect, the disclosure features an isolated peptide containing, or consisting of, amino acids 1-20 of the MUC1-CD (or SEQ ID NO:3 (amino acids 1-20 of human MUC1-CD), but with not more than four (e.g., four, three, two, or one) substitutions.

In another aspect, the disclosure features an isolated peptide containing, or consisting of, amino acids 270-322 of caspase-8 (e.g., SEQ ID NO:27 or SEQ ID NO:28), but with not more than four (e.g., four, three, two, or one) substitutions.

In another aspect, the disclosure features an isolated peptide comprising: a first amino acid sequence that (i) contains, or consists of, amino acids 1-20 of the MUC1-CD or (ii) SEQ ID NO:3 (amino acids 1-20 of human MUC1-CD), but with not more than four (e.g., four, three, two, or one) substitutions; and a second amino acid sequence that is heterologous to the first amino acid sequence.

In another aspect, the disclosure features an isolated peptide comprising: a first amino acid sequence that contains, or consists of, amino acids 270-322 of human caspase-8 (e.g., the amino acid sequence depicted in SEQ ID NO:27 or SEQ ID NO:28), but with not more than four (e.g., four, three, two, or one) substitutions; and a second amino acid sequence that is heterologous to the first amino acid sequence.

In another aspect, the disclosure features any a polypeptide comprising or consisting of any of the amino acid sequences depicted herein or a nucleic acid encoding the polypeptide.

In another aspect, the disclosure features a nucleic acid comprising, or consisting of, any of the nucleic acid sequences depicted herein.

In some embodiments of any of the peptides, the substitutions can be conservative or non-conservative, or a combination of both.

In another aspect, the disclosure also features a vector (e.g., an expression vector) comprising any of the nucleic acids described herein (e.g., a nucleic acid encoding any of the peptides described herein) and a cell containing the vector. In expression vectors, coding sequences are operably linked to expression control sequences (e.g., transcriptional regulatory elements (TRE)). Cells containing vectors (host cells) can be eukaryotic (e.g., mammalian, insect, or fungal, including, yeast) cells or prokaryotic (e.g., bacterial) cells. Also featured is a method of producing the protein, wherein the cell is cultured under conditions that permit the expression of the peptide. The method can also include isolating the peptide from the cells or from the medium in which the cell is cultured.

As noted above, anti-apoptotic DED-containing proteins include, e.g., DEDD2, c-FLIP (long and short), PEA-15, and BAR, Pro-apoptotic DED-containing proteins include, e.g., FADD, caspase-10, DEDD, Hip-1, Hippi, and BAP31. Exemplary amino acid sequences for, as well as sequence alignments of, several DED-containing proteins are provided herein and in, e.g., Tibbets et al. (Nature Immunology (2003) 4(5):404-409), the disclosure of which is incorporated by reference.

As used herein, a subject "at risk of developing a pathological condition characterized by a decreased level of apoptosis" is a subject that has a predisposition to develop the condition (i.e., a genetic predisposition to develop a cancer such as a mutation in a tumor suppressor gene (e.g., mutation in BRCA1, p53, RB, or APC) or a genetic predisposition to develop an inflammatory condition (e.g., a family history of rheumatoid arthritis or Crohn's disease)) or has been exposed to conditions that can result in the condition. Thus, a subject can be one "at risk of developing a cancer" when the subject has been exposed to mutagenic or carcinogenic levels of certain compounds (e.g., carcinogenic compounds in cigarette smoke such as acrolein, arsenic, benzene, benz{a}anthracene, benzo {a}pyrene, polonium-210 (Radon), urethane, or vinyl chloride). Moreover, the subject can be "at risk of developing a cancer" when the subject has been exposed to, e.g., large doses of ultraviolet light or X-irradiation, or exposed (e.g., infected) to a tumor-causing/associated virus such as papillomavirus, Epstein-Barr virus, hepatitis B virus, or human T-cell leukemia-lymphoma virus. A subject "at risk of developing an inflammatory disorder" refers to a subject with a family history of one or more inflammatory disorders (e.g., a genetic predisposition to one or more inflammatory disorders) or one exposed to one or more inflammation-inducing conditions. For example, a subject can have been exposed to a viral or bacterial superantigen such as, but not limited to, Staphylococcal enterotoxins (SEs), a *Streptococcus pyogenes* exotoxin (SPE), a *Staphylococcus aureus* toxic shock-syndrome toxin (TSST-1), a Streptococcal mitogenic exotoxin (SME) and a Streptococcal superantigen (SSA). Where the condition results or can result from a microbial infection, the "at risk" subject can also be one who has been exposed (or is under threat of exposure) to a microbe encoding a protein that can inhibit apoptosis in a cell (such as any of the microbes described herein).

Cancer is a class of diseases or disorders characterized by uncontrolled division of cells and the ability of these to spread, either by direct growth into adjacent tissue through invasion, or by implantation into distant sites by metastasis (where cancer cells are transported through the bloodstream or lymphatic system). Cancer can affect people at all ages, but risk tends to increase with age. Types of cancers can include, e.g., lung cancer, breast cancer, colon cancer, pancreatic cancer, renal cancer, stomach cancer, liver cancer, bone cancer, hematological cancer, neural tissue cancer (e.g., glioblastoma such as glioblastoma multiforme), melanoma, thyroid cancer, ovarian cancer, testicular cancer, prostate cancer, cervical cancer, vaginal cancer, or bladder cancer.

An "inflammatory disorder," as used herein, refers to a process in which one or more substances (e.g., substances not naturally occurring in the subject), via the action of white blood cells (e.g., B cells, T cells, macrophages, monocytes, or dendritic cells), inappropriately trigger a pathological response, e.g., a pathological immune response. Accordingly, such immune cells involved in the inflammatory response are referred to as "inflammatory cells." The inappropriately triggered inflammatory response can be one where no foreign substance (e.g., an antigen, a virus, a bacterium, or a fungus) is present in or on the subject. The inappropriately triggered response can be one where a self-component (e.g., a self-antigen) is targeted (e.g., an autoimmune disorder such as multiple sclerosis) by the inflammatory cells. The inappropriately triggered response can also be a response that is inappropriate in magnitude or duration, e.g., anaphylaxis. Thus, the inappropriately targeted response can be due to the presence of a microbial infection (e.g., viral, bacterial, or fungal). Types of inflammatory disorders (e.g., autoimmune disease) can include, but are not limited to, osteoarthritis, rheumatoid arthritis (RA), spondyloarthropathies, POEMS syndrome, Crohn's disease, graft-versus host disease, multicentric Castleman's disease, systemic lupus erythematosus (SLE), multiple sclerosis (MS), muscular dystrophy (MD), insulin-dependent diabetes mellitus (IDDM), dermatomyositis, polymyositis, inflammatory neuropathies such as Guillain Barre syndrome, vasculitis such as Wegener's granulomatosus, polyarteritis nodosa, polymyalgia rheumatica, temporal arteritis, Sjogren's syndrome, Bechet's disease, Churg-Strauss syndrome, or Takayasu's arteritis. Also included in inflammatory disorders are certain types of allergies such as rhinitis, sinusitis, urticaria, hives, angioedema, atopic dermatitis, food allergies (e.g., a nut, such as a peanut, allergy), drug allergies (e.g., penicillin), insect allergies (e.g., allergy to a bee sting), or mastocytosis. Inflammatory disorders can also include ulcerative colitis and asthma.

A subject "suspected of having a pathological condition characterized by a decreased level of apoptosis" is one having one or more symptoms of the condition. Symptoms of cancer are well-known to those of skill in the art and include, without limitation, breast lumps, nipple changes, breast cysts, breast pain, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, or pain), pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, and pancreas metastases, difficulty swallowing, and the like. Symptoms of inflammatory disorders are well known in the art and include, but are not limited to, redness, swelling (e.g., swollen joints), joints that are warm to the touch, joint pain, stiffness, loss of joint function, fever, chills, fatigue, loss of energy, headaches, loss of appetite, muscle stiffness, insomnia, itchiness, stuffy nose, sneezing, coughing, one or more neurologic symptoms such as dizziness, seizures, or pain.

From the above it will be clear that neither subjects "at risk of developing a pathological condition characterized by a decreased level of apoptosis" nor subjects "suspected of having a pathological condition characterized by a decreased level of apoptosis" are all the subjects within a species of interest.

As used herein, a subject "at risk of developing a pathological condition characterized by an elevated level of apoptosis" is a subject that has a predisposition to develop the condition (i.e., a genetic predisposition to develop a neurological disorder (e.g., Alzheimer's disease) or a genetic predisposition to develop a ischemic event (e.g., a family history of cardiovascular disorders)) or has been exposed to conditions that can result in the condition. Conditions that may put a subject at risk for developing a pathological condition characterized by an elevated level of apoptosis will vary depending on the particular condition. For example, risk factors for an ischemic event include, e.g., smoking, diet (e.g., a diet high in fat or LDL cholesterol), lack of physical activity, alcoholism, and/or race (e.g., African-American heritage) and gender.

Pathological conditions characterized by an elevated level of apoptosis include any of those described herein and known in the art.

A subject "suspected of having a pathological condition characterized by an elevated level of apoptosis" is one having one or more symptoms of the condition. Symptoms of these conditions vary greatly depending on the particular condition and are well-known in the art. Symptoms of a neurodegenerative disorders include, e.g., memory loss, impaired sensory perception, impaired motor function, incontinence, and/or difficulties speaking. Symptoms of an ischemic event include, e.g., chest pain, pain in the arm, difficulty breathing, paralysis (e.g., on one side of the body), loss of circulation, gangrene, blueness or paleness of an affected limb, muscle weakness, and/or numbness of an affected limb or region.

From the above it will be clear that neither subjects "at risk of developing a pathological condition characterized by a decreased level of apoptosis" nor subjects "suspected of having a pathological condition characterized by an elevated level of apoptosis" are all the subjects within a species of interest.

"Polypeptide" and "protein" are used interchangeably and mean any peptide-linked chain of amino acids, regardless of length or post-translational modification. The MUC1, caspase-8, and DED-containing protein (e.g., FADD or any other DED-containing proteins described herein) molecules and reagents used in any of the methods described herein can contain or be wild-type proteins or can be variants that have not more than 50 (e.g., not more than one, two, three, four, five, six, seven, eight, nine, ten, 12, 15, 20, 25, 30, 35, 40, or 50) conservative amino acid substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. All that is required as that: (i) such variants of MUC1 have at least 25% (e.g., at least: 30%; 40%; 50%; 60%; 70%; 75%; 80%; 85%; 90%; 95%; 97%; 98%; 99%; 99.5%, or 100% or even greater) of the ability of wild-type, full-length, mature MUC1 or MUC1-CD (cytoplasmic domain) to bind to caspase-8 or to a DED-containing protein (e.g., FADD); (ii) such variants of caspase-8 have at least 25% (e.g., at least: 30%; 40%; 50%; 60%; 70%; 75%; 80%; 85%; 90%; 95%; 97%; 98%; 99%; 99.5%, or 100% or even greater) of the ability of wild-type, full-length, caspase-8 (or the p18 subunit of caspase-8) to bind to bind to wild-type, full-length, mature MUC1 or MUC1-CD; and (iii) such variants of DED-containing proteins (e.g., FADD or any other DED-containing protein described herein) have at least 25% (e.g., at least: 30%; 40%; 50%; 60%; 70%; 75%; 80%; 85%; 90%; 95%; 97%; 98%; 99%; 99.5%, or 100% or even greater) of the ability of the relevant wild-type, full-length DED-containing protein to bind to wild-type, full-length, mature MUC1 or MUC1-CD.

The disclosure features fragments (e.g., functional, immunogenic, and antigenic fragments) of all of the polypeptides disclosed herein. A "polypeptide fragment," as used herein, refers to a segment of the polypeptide that is shorter than a full-length, immature polypeptide. A "functional fragment" of a polypeptide has at least 10% (e.g., at least 10%, at least 15%, at least 20%, at least 25%, at least 30%, at least 35%, at least 40%, at least 50%, at least 55%, at least 60%, at least 70%, at least 80%, at least 90%, at least 95%, at least 98%, at least 99%, at least 99.5%, or 100% or more) of the activity of the mature, polypeptide (or in the case of the p18 subunit of caspase-8 and/or the DED from a corresponding DED-containing protein, the activity of the p18 subunit or DED).

Fragments of a polypeptide include terminal as well internal deletion variants of a polypeptide. Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. An immunogenic fragment is one that has at least 25% (e.g., at least: 30%; 40%; 50%; 60%; 70%; 75%; 80%; 85%; 90%; 95%; 97%; 98%; 99%; 99.5%, or 100% or even more) of the ability of the relevant full-length, wild-type protein to stimulate an immune response (e.g., an antibody response or a cellular immune response) in an animal of interest. An antigenic fragment of a protein is one having at least 25% (e.g., at least: 30%; 40%; 50%; 60%; 70%; 75%; 80%; 85%; 90%; 95%; 97%; 98%; 99%; 99.5%, or 100% or even greater) of the ability of the relevant full-length, wild-type polypeptide or test agent to be recognized by an antibody specific for the protein or a T cell specific to the protein.

As used herein, an "caspase-8 reagent" or "caspase-8 polypeptide" contains, or is: (a) a full-length, wild-type, unprocessed caspase-8; (b) a p18 subunit of caspase-8; (c) a functional fragment of (a) or (b); or (d) (a), (b), or (c) with not more than 50 (see above) conservative substitutions. "MUC1-binding fragments" of caspase-8 polypeptides, as used herein, refer to any caspase-8 fragments that substantially retain the ability to bind MUC1 (e.g., the MUC1-CD) (i.e., that have at least 25% (e.g., at least 25%, at least 30%, at least 35%, at least 40%, at least 50%, at least 55%, at least 60%, at least 70%, at least 80%, at least 90%, at least 95%, at least 98%, at least 99%, at least 99.5%, or 100% or more) of the ability of the full-length, wild-type, unprocessed caspase-8 to bind to MUC1 (e.g., the MUC1-CD). "Functional fragments" of caspase-8 include fragments that contain the p18 subunit, e.g., amino acids 270-322 of full-length, unprocessed caspase-8. In addition, "caspase-8 reagents" can include with (a), (b), (c), or (d) above, internal or terminal (C or N) irrelevant or heterologous amino acid sequences (e.g., sequences derived from other proteins or synthetic sequences not corresponding to any naturally occurring protein). The sequences can be, for example, an antigenic tag (e.g., FLAG, polyhistidine, hemagluttanin (HA), glutathione-S-transferase (GST), or maltose-binding protein (MBP)). Heterologous sequences can also be proteins useful as diagnostic or detectable markers, for example, luciferase, green fluorescent protein (GFP), or chloramphenicol acetyl transferase (CAT). Heterologous sequences can be of varying length and in some cases can be a larger sequences than the caspase-8 polypeptide. Generally, the heterologous sequences are about 1-50 (e.g., two, four, eight, ten, 15, 20, 25, 30, 35, 40, or 45) amino acids in length. Caspase-8 reagents, other than full-length, wild-type, unprocessed caspase-8 molecules, have at least 30% (e.g., at least 30%, at least 35%, at least 40%, at least 50%, at least 55%, at least 60%, at least 70%, at least 80%, at least 90%, at least 95%, at least 98%, at least 99%, at least 99.5%, or 100% or more) of the ability of the full-length, wild-type, unprocessed caspase-8 to bind to the cytoplasmic domain of MUC1.

As used herein, a "DED-containing protein reagent" or "DED-containing polypeptide" contains, or is: (a) full-length, wild-type mature DED-containing protein; (b) a functional fragment of the DED-containing protein; or (c) (a) or (b) but with not more than 50 (see above) conservative substitutions. In addition, "DED-containing protein reagents" or "DED-containing polypeptides" can include with (a), (b), or (c), internal or terminal (C or N) irrelevant amino acid sequences (e.g., sequences derived from other proteins or synthetic sequences not corresponding to any naturally occurring protein) as described above for caspase-8 reagents and caspase-8 polypeptides. DED-containing proteins can be, e.g., pro-apoptotic or anti-apoptotic, examples of each of which are described herein. Exemplary MUC1-binding fragments of DED-containing proteins include, e.g., the DED of a FADD (e.g., SEQ ID NO:8).

As used herein, a "MUC1 reagent" or "MUC1 polypeptide" contains, or is: (a) full-length, wild-type mature MUC1; (b) a functional fragment of MUC1; or (c) (a) or (b) but with not more than 50 (see above) conservative substitutions. In addition, "MUC1 reagents" or "MUC1 polypeptides" can include with (a), (b), or (c), internal or terminal (C or N) irrelevant amino acid sequences (e.g., sequences derived from other proteins or synthetic sequences not corresponding to any naturally occurring protein) as described above for caspase-8 reagents and caspase-8 polypeptides.

As used herein, "MUC1 cytoplasmic domain" or MUC1-CD" refers to a 72 amino acid portion of the full-length MUC1 (SEQ ID NO:1) and is depicted in SEQ ID NO:2. Caspase-8 binding fragments of MUC1 include, e.g., amino acids 1-20 of MUC1-CD (e.g., SEQ ID NO:3). DED-containing protein-binding fragments of MUC1 include, e.g., amino acids 46-72 of the MUC1-CD (e.g., SEQ ID NO:4).

A caspase-8 polypeptide, a DED-containing polypeptide, and MUC1 polypeptide can be from any species (e.g., nematode, insect, plant, bird, reptile, or mammal (e.g., a mouse, rat, dog, cat, goat, pig, cow, horse, whale, or monkey) that expresses a homolog of the relevant human polypeptide.

Exemplary Amino Acid Sequences

The following is an exemplary amino acid sequence for a full-length, wild-type, human MUC1:

```
                                          (SEQ ID NO: 1)
MTPGTQSPFFLLLLLTVLTVVTGSGHASSTPGGEKETSATQRSSVPSSTE

KNAIPAPTTTKSCRETFLKCFCRFINKGVFWASPILSSVSDVPFPFSAQS

GAGVPGWGIALLVLVCVLVALAIVYLIALAVCQCRRKNYGQLDIFPARDT

YHPMSEYPTYHTHGRYVPPSSTDRSPYEKVSAGNGGSSLSYTNPAVAATS

ANL.
```

The following the amino acid sequence of the human MUC1-CD polypeptide:

```
                                          (SEQ ID NO: 2)
CQCRRKNYGQLDIFPARDTYHPMSEYPTYHTHGRYVPPSSTDRSPYEKVS

AGNGGSSLSYTNPAVAATSANL.
```

The following is the amino acid sequence for amino acids 1-20 of the human MUC1-CD:

```
    CQCRRKNYGQLDIFPARDTY.         (SEQ ID NO: 3)
```

The following is the amino acid sequence for amino acids 46-72 of the human MUC1-CD:

```
    YEKVSAGNGGSSLSYTNPAVAATSANL   (SEQ ID NO: 4).
```

The following is the amino acid sequence for full-length, human, unprocessed caspase-8 (UNIPROT:Q14790):

```
                                          (SEQ ID NO: 5)
MDFSRNLYDIGEQLDSEDLASLKFLSLDYIPQRKQEPIKDALMLFQRLQE

KRMLEESNLSFLKELLFRINRLDLLITYLNTRKEEMERELQTPGRAQISA

YRVMLYQISEEVSRSELRSFKFLLQEEISKCKLDDDMNLLDIFIEMEKRV

ILGEGKLDILKRVCAQINKSLLKIINDYEEFSKERSSSLEGSPDEFSNGE

ELCGVMTISDSPREQDSESQTLDKVYQMKSKPRGYCLIINNHNFAKAREK

VPKLHSIRDRNGTHLDAGALTTTFEELHFEIKPHDDCTVEQIYEILKIYQ

LMDHSNMDCFICCILSHGDKGIIYGTDGQEAPIYELTSQFTGLKCPSLAG

KPKVFFIQACQGDNYQKGIPVETDSEEQPYLEMDLSSPQTRYIPDEADFL

LGMATVNNCVSYRNPAEGTWYIQSLCQSLRERCPRGDDILTILTEVNYEV

SNKDDKKNMGKQMPQPTFTLRKKLVFPSD.
```

The following are the amino acid sequences of two DED in human caspase-8:

```
                                          (SEQ ID NO: 34)
MDFSRNLYDIGEQLDSEDLASLKFLSLDYIPQRKQEPIKDALMLFQRLQE

KRMLEESNLSFLKELLFRINR (SEQ ID NO: 35)
SAYRVMLYQISEEVSRSELRSFKFLLQEEISKCKLDDDMNLLDIFIEMEK

RVILGEGKLDILKRVCAQINK
```

The following is the amino acid sequence for the p18 subunit of processed human caspase-8 (UNIPROT:Q14790|217-374):

```
                                          (SEQ ID NO: 6)
SESQTLDKVYQMKSKPRGYCLIINNHNFAKAREKVPKLHSIRDRNGTHLD

AGALTTTFEELHFEIKPHDDCTVEQIYEILKIYQLMDHSNMDCFICCILS

HGDKGIIYGTDGQEAPIYELTSQFTGLKCPSLAGKPKVFFIQACQGDNYQ

KGIPVETD.
```

The following is the amino acid sequence for full-length, human FADD (UNIPROT:Q13158):

```
                                          (SEQ ID NO: 7)
MDPFLVLLHSVSSSLSSSELTELKFLCLGRVGKRKLERVQSGLDLFSMLL

EQNDLEPGHTELLRELLASLRRHDLLRRVDDFEAGAAAGAAPGEEDLCAA

FNVICDNVGKDWRRLARQLKVSDTKIDSIEDRYPRNLTERVRESLRIWKN

TEKENATVAHLVGALRSCQMNLVADLVQEVQQARDLQNRSGAMSPMSWNS

DASTSEAS.
```

The following is the amino acid sequence for a DED in human FADD (UNIPROT:Q13158|3-81):

```
                                          (SEQ ID NO: 8)
PFLVLLHSVSSSLSSSELTELKFLCLGRVGKRKLERVQSGLDLFSMLLEQ

NDLEPGHTELLRELLASLRRHDLLRRVDD.
```

The following is the amino acid sequence for full-length human caspase-10 (UNIPROT:Q92851):

```
                                          (SEQ ID NO: 9)
MKSQGQHWYSSSDKNCKVSFREKLLIIDSNLGVQDVENLKFLCIGLVPNK

KLEKSSSASDVFEHLLAEDLLSEEDPFFLAELLYIIRQKKLLQHLNCTKE
```

EVERLLPTRQRVSLFRNLLYELSEGIDSENLKDMIFLLKDSLPKTEMTSL

SFLAFLEKQGKIDEDNLTCLEDLCKTVVPKLLRNIEKYKREKAIQIVTPP

VDKEAESYQGEEELVSQTDVKTFLEALPQESWQNKHAGSNGNRATNGAPS

LVSRGMQGASANTLNSETSTKRAAVYRMNRNHRGLCVIVNNHSFTSLKDR

QGTHKDAEILSHVFQWLGFTVHIHNNVTKVEMEMVLQKQKCNPAHADGDC

FVFCILTHGRFGAVYSSDEALIPIREIMSHFTALQCPRLAEKPKLFFIQA

CQGEEIQPSVSIEADALNPEQAPTSLQDSIPAEADFLLGLATVPGYVSFR

HVEEGSWYIQSLCNHLKKLVPRMLKFLEKTMEIRGRKRTVWGAKQISATS

LPTAISAQTPRPPMRRWSSVS.

The following are the amino acid sequences for two DED in human caspase-10:

(SEQ ID NO: 10)
VSFREKLLIIDSNLGVQDVENLKFLCIGLVPNKKLEKSSSASDVFEHLLA

EDLLSEEDPFFLAELLYIIRQKKLLQHLN (SEQ ID NO: 29)
SLFRNLLYELSEGIDSENLKDMIFLLKDSLPKTEMTSLSFLAFLEKQGKI

DEDNLTCLEDLCKTVVPKLLRNIE.

The following is the amino acid sequence for full-length human DEDD protein (UNIPROT:O75618):

(SEQ ID NO: 11)
MAGLKRRASQVWPEEHGEQEHGLYSLHRMFDIVGTHLTHRDVRVLSFLFV

DVIDDHERGLIRNGRDFLLALERQGRCDESNFRQVLQLLRIITRHDLLPY

VTLKRRRAVCPDLVDKYLEETSIRYVTPRALSDPEPRPPQPSKTVPPHYP

VVCCPTSGPQMCSKRPARGRATLGSQRKRRKSVTPDPKEKQTCDIRLRVR

AEYCQHETALQGNVFSNKQDPLERQFERFNQANTILKSRDLGSIICDIKF

SELTYLDAFWRDYINGSLLEALKGVFITDSLKQAVGHEAIKLLVNVDEED

YELGRQKLLRNLMLQALP.

The following is the amino acid sequence for a DED in human DEDD protein (UNIPROT:O75618|25-103):

(SEQ ID NO: 12)
SLHRMFDIVGTHLTHRDVRVLSFLFVDVIDDHERGLIRNGRDFLLALERQ

GRCDESNFRQVLQLLRIITRHDLLPYVTL.

The following is the amino acid sequence for full-length human BAR protein (UNIPROT:Q9NZS9):

(SEQ ID NO: 13)
MEEPQKSYVNTMDLERDEPLKSTGPQISVSEFSCHCCYDILVNPTTLNCG

HSFCRHCLALWWASSKKTECPECREKWEGFPKVSILLRDAIEKLFPDAIR

LRFEDIQQNNDIVQSLAAFQKYGNDQIPLAPNTGRANQQMGGGFFSGVLT

ALTGVAVVLLVYHWSSRESEHDLLVHKAVAKWTAEEVVLWLEQLGPWASL

YRERFLSERVNGRLLLTLTEEEFSKTPYTIENSSHRRAILMELERVKALG

VKPPQNLWEYKAVNPGRSLFLLYALKSSPRLSLLYLYLFDYTDTFLPFIH

TICPLQEDSSGEDIVTKLLDLKEPTWKQWREFLVKYSFLPYQLIAEFAWD

WLEVHYWTSRFLIINAMLLSVLELFSFWRIWSRSELKTVPQRMWSHFWKV

STQGLFVAMFWPLIPQFVCNCLFYWALYFNPIINIDLVVKELRRLETQV.

The following is the amino acid sequence of a DED in human BAR:

(SEQ ID NO: 36)
ALKSSPRLSLLYLYLFDYTDTFLPFIHTICPLQEDSSGEDIVTKLLDLKE

PTWKQWREFLVKYSFLPYQLIA

The following is the amino acid sequence for full-length human DEDD2 protein (UNIPROT:Q8WXF8):

(SEQ ID NO: 15)
MALSGSTPAPCWEEDECLDYYGMLSLHRMFEVVGGQLTECELELLAFLLD

EAPGAAGGLARARSGLELLLELERRGQCDESNLRLLGQLLRVLARHDLLP

HLARKRRRPVSPERYSYGTSSSSKRTEGSCRRRRQSSSSANSQQGQWETG

SPPTKRQRRSRGRPSGGARRRRRGAPAAPQQQSEPARPSSEGKVTCDIRL

RVRAEYCEHGPALEQGVASRRPQALARQLDVFGQATAVLRSRDLGSVVCD

IKFSELSYLDAFWGDYLSGALLQALRGVFLTEALREAVGREAVRLLVSVD

EADYEAGRRRLLLMEEEGGRRPTEAS.

The following is the amino acid sequence of a DED in human DEDD2 protein (UNIPROT:Q8WXF8|25-104):

(SEQ ID NO: 16)
SLHRMFEVVGGQLTECELELLAFLLDEAPGAAGGLARARSGLELLLELER

RGQCDESNLRLLGQLLRVLARHDLLPHLAR.

The following is the amino acid sequence of full-length human Hip-1 protein (UNIPROT:O00291):

(SEQ ID NO: 17)
MKQVPNPLPKVLSRRGVGAGLEAAERESFERTQTVSINKAINTQEVAVKE

KHARTCILGTHHEKGAQTFWSVVNRLPLSSNAVLCWKFCHVFHKLLRDGH

PNVLKDSLRYRNELSDMSRMWGHLSEGYGQLCSIYLKLLRTKMEYHTKNP

RFPGNLQMSDRQLDEAGESDVNNFFQLTVEMFDYLECELNLFQTVFNSLD

MSRSVSVTAAGQCRLAPLIQVILDCSHLYDYTVKLLFKLHSCLPADTLQG

HRDRFMEQFTKLKDLFYRSSNLQYFKRLIQIPQLPENPPNFLRASALSEH

ISPVVVIPAEASSPDSEPVLEKDDLMDMDASQQNLFDNKFDDIFGSSFSS

DPFNFNSQNGVNKDEKDHLIERLYREISGLKAQLENMKTESQRVVLQLKG

HVSELEADLAEQQHLRQQAADDCEFLRAELDELRRQREDTEKAQRSLSEI

ERKAQANEQRYSKLKEKYSELVQNHADLLRKNAEVTKQVSMARQAQVDLE

REKKELEDSLERISDQGQRKTQEQLEVLESLKQELATSQRELQVLQGSLE

TSAQSEANWAAEFAELEKERDSLVSGAAHREEELSALRKELQDTQLKLAS

TEESMCQLAKDQRKMLLVGSRKAAEQVIQDALNQLEEPPLISCAGSADHL

LSTVTSISSCIEQLEKSWSQYLACPEDISGLLHSITLLAHLTSDAIAHGA

TTCLRAPPEPADSLTEACKQYGRETLAYLASLEEEGSLENADSTAMRNCL

-continued
```
SKIKAIGEELLPRGLDIKQEELGDLVDKEMAATSAAIETATARIEEMLSK

SRAGDTGVKLEVNERILGCCTSLMQAIQVLIVASKDLQREIVESGRGTAS

PKEFYAKNSRWTEGLISASKAVGWGATVMVDAADLVVQGRGKFEELMVCS

HEIAASTAQLVAASKVKADKDSPNLAQLQQASRGVNQATAGVVASTISGK

SQIEETDNMDFSSMTLTQIKRQEMDSQVRVLELENELQKERQKLGELRKK

HYELAGVAEGWEEGTEASPPTLQEVVTEKE.
```

The following is the amino acid sequence for a DED domain in human Hip-1 protein (UNIPROT:O00291|403-484):

```
                                      (SEQ ID NO: 18)
SELEADLAEQQHLRQQAADDCEFLRAELDELRRQREDTEKAQRSLSEIER

KAQANEQRYSKLKEKYSELVQNHADLLRKNAE.
```

The following is the amino acid sequence for full-length human BAP31 protein:

```
                                      (SEQ ID NO: 19)
MTLQWTAVATFLYAEVFVVLLLCIPFISPKRWQKIFKSRLVELLVSYGNT

FFVVLIVILVLLVIDAVREIRKYDDVTEKVNLQNNPGAMEHFHMKLFRAQ

RNLYIAGFSLLLSFLLRRLVTLISQQATLLASNEAFKKQAESASEAAKKY

MEENDQLKKGAAVDGGKLDVGNAEVKLEEENRSLKADLQKLKDELASTKQ

KLEKAENEVLAMIAVDGPMDKKEE.
```

The following is the amino acid sequence for a DED in human BAP31 protein:

```
                                      (SEQ ID NO: 37)
DVGNAEVKLEEENRSLKADLQKLKDELASTKQKLEKAENEVLAMRKQSEG

LTKEYDRLLEEHA
```

The following is the amino acid sequence for full-length human c-FLIP$_L$ protein (UNIPROT:O15519-1):

```
                                      (SEQ ID NO: 21)
MSAEVIHQVEEALDTDEKEMLLFLCRDVAIDVVPPNVRDLLDILRERGKL

SVGDLAELLYRVRRFDLLKRILKMDRKAVETHLLRNPHLVSDYRVLMAEI

GEDLDKSDVSSLIFLMKDYMGRGKISKEKSFLDLVVELEKLNLVAPDQLD

LLEKCLKNIHRIDLKTKIQKYKQSVQGAGTSYRNVLQAAIQKSLKDPSNN

FRLHNGRSKEQRLKEQLGAQQEPVKKSIQESEAFLPQSIPEERYKMKSKP

LGICLIIDCIGNETELLRDTFTSLGYEVQKFLHLSMHGISQILGQFACMP

EHRDYDSFVCVLVSRGGSQSVYGVDQTHSGLPLHHIRRMFMGDSCPYLAG

KPKMFFIQNYVVSEGQLEDSSLLEVDGPAMKNVEFKAQKRGLCTVHREAD

FFWSLCTADMSLLEQSHSSPSLYLQCLSQKLRQERKRPLLDLHIELNGYM

YDWNSRVSAKEKYYVWLQHTLRKKLILSYT.
```

The following is the amino acid sequence for a DED in full length human c-FLIP$_L$ protein:

```
                                      (SEQ ID NO: 22)
SDYRVLMAEIGEDLDKSDVSSLIFLMKDYMGRGKISKEKSFLDLVVELEK

LNLVAPDQLDLLEKCLKNIHRIDLKTKIQ.
```

The following is the amino acid sequence for full-length human c-FLIPs (UNIPROT:>O15519-2):

```
                                      (SEQ ID NO: 23)
MSAEVIHQVEEALDTDEKEMLLFLCRDVAIDVVPPNVRDLLDILRERGKL

SVGDLAELLYRVRRFDLLKRILKMDRKAVETHLLRNPHLVSDYRVLMAEI

GEDLDKSDVSSLIFLMKDYMGRGKISKEKSFLDLVVELEKLNLVAPDQLD

LLEKCLKNIHRIDLKTKIQKYKQSVQGAGTSYRNVLQAAIQKSLKDPSNN

FRMITPYAHCPDLKILGNCSM.
```

The following is the amino acid sequence for a DED in human c-FLIPs:

```
                                      (SEQ ID NO: 38)
MSAEVIHQVEEALDTDEKEMLLFLCRDVAIDVVPPNVRDLLDILRERGKL

SVGDLAELLYRVRRFDLL
```

The following is the amino acid sequence for a full-length human Hippi protein (UNTPROT:Q9NWB7):

```
                                      (SEQ ID NO: 25)
MTAALAVVTTSGLEDGVPRSRGEGTGEVVLERGPGAAYHMFVVMEDLVEK

LKLLRYEEEFLRKSNLKAPSRHYFALPTNPGEQFYMFCTLAAWLINKAGR

PFEQPQEYDDPNATISNILSELRSFGRTADFPPSKLKSGYGEHVCYVLDC

FAEEALKYIGFTWKRPIYPVEELEEESVAEDDAELTLNKVDEEFVEEETD

NEENFIDLNVLKAQTYHLDMNETAKQEDILESTTDAAEWSLEVERVLPQL

KVTIRTDNKDWRIHVDQMHQHRSGIESALKETKGFLDKLHNEITRTLEKI

SSREKYINNQLENLVQEYRAAQAQLSEAKERYQQGNGGVTERTRLLSEVM

EELEKVKQEMEEKGSSMTDGAPLVKIKQSLTKLKQETVEMDIRIGIVEHT

LLQSKLKEKSNMTRNMHATVIPEPATGFY.
```

The following is the amino acid sequence for a DED in full-length human Hippi (UNIPROT:Q9NWB7|335-426):

```
                                      (SEQ ID NO: 26)
GNGGVTERTRLLSEVMEELEKVKQEMEEKGSSMTDGAPLVKIKQSLTKLK

QETVEMDIRIGIVEHTLLQSKLKEKSNMTRNMHATVIPEPAT.
```

The following are the amino acid sequences for amino acids 270-322 of a human caspase-8 protein:

```
                                      (SEQ ID NO: 27)
KLHSIRDRNGTHLDAGALTTTFEELHFEIKPHHDCTVEQIYEILKIYQLM

DHS
                                      (SEQ ID NO: 28)
KLHSIRDRNGTHLDAGALTTTFEELHFEIKPHDDCTVEQIYEILKIYQLM

DHS.
```

SEQ ID NO:27 differs from SEQ ID NO:28 in having an "H" at position 33 rather than a "D". The "H" at position 33 in SEQ ID NO:27 and the "D" at position 33 in SEQ ID NO:28 are shown in bold. It is understood that in caspase-8 reagents and polypeptides of the present disclosure that include the relevant residue, it can be a "D" or an "H". It is noted that in the full-length, unprocessed human caspase-8 polypeptide depicted as SEQ ID NO:5 (see above), the relevant residue is a "D".

As used herein, "operably linked" means incorporated into a genetic construct so that expression control sequences effectively control expression of a coding sequence of interest.

Unless otherwise defined, all technical and scientific terms used herein have the same meaning as commonly understood by one of ordinary skill in the art to which this invention pertains. Preferred methods and materials are describe below, although methods and materials similar or equivalent to those described herein can be used in the practice or testing of the present invention. All publications, patent applications, patents, and other references mentioned herein are incorporated by reference in their entirety. The materials, methods, and examples disclosed herein are illustrative only and not intended to be limiting.

Other features and advantages of the disclosure, e.g., methods for treating cancer, will be apparent from the following description, from the drawings, and from the claims.

BRIEF DESCRIPTION OF THE DRAWINGS

FIG. 1A: BC-1 cells were infected with lentiviruses expressing the CsiRNA, MUC1siRNA#1 or MUC1siRNA#2. Lysates from the indicated cell populations were immunoblotted with anti-MUC1-C and anti-β-actin antibodies as indicated to the right of the photographs. The molecular weights of each of the proteins (in kilodaltons (kDa)) are indicated to the left of each of the photographs.

FIG. 1B: The indicated BC-1 cell populations were treated with 50 ng/ml FasL for 8 hours. Lysates were immunoblotted with anti-caspase-8 or anti-β-actin antibodies as indicated to the right of the photographs. The molecular weights of each of the proteins (in kilodaltons (kDa)) are indicated to the left of each of the photographs.

FIG. 1C: The indicated BC-1 cell populations were treated with 50 ng/ml FasL for 24 hours and then analyzed by fluorescence assisted cell sorting (FACS) to determine the sub-G1 DNA content in the cells.

FIG. 1D: The results obtained with the indicated BC-1 cell populations left untreated (open bars) or treated with FasL (solid bars) are expressed as the percentage apoptosis (mean+SD for three experiments).

FIG. 4A: U-937 cells were infected with retroviruses expressing the control pLXIN vector or pLXIN-MUC1-C. Lysates were immunoblotted with anti-MUC1-C and anti-β-actin antibodies as indicated to the right of the photographs. The molecular weights of each of the proteins (in kilodaltons (kDa)) are indicated to the left of each of the photographs.

FIG. 4B: Lysates from the indicated U-937 cell populations treated with 10 ng/ml TNFα were immunoblotted with anti-caspase-8 or anti-β-actin antibodies as indicated to the right of the photographs. The molecular weights of each of the proteins (in kilodaltons (kDa)) are indicated to the left of each of the photographs.

FIG. 4C: The indicated U-937 cell populations were treated with 10 ng/ml TNFα or 50 ng/ml FasL for 24 hours and monitored for sub-G1 content.

FIG. 4D: The results of the experiment depicted in FIG. 4C are expressed as the percentage apoptosis (mean+SD of three experiments).

FIGS. 7A-D are a series of photographs of western blots and bar graphs.

FIGS. 7A-7C: MCF-10A cells were transfected with control siRNA or MUC1 siRNA pools for 72 h and then stimulated with TRAIL (FIG. 7A), TNFα (FIG. 7B), or FasL (FIG. 7C). Lysates were immunoblotted with anti-caspase-8 or anti-β-actin antibodies as indicated to the right of the photographs. The molecular weights of each of the proteins (in kilodaltons (kDa)) are indicated to the left of each of the photographs. Lysates were also assayed for caspase-8 activity using the BD ApoAlert kit (right panels). The results are expressed as the absorbance (Abs) at 405 nm.

FIG. 7D: Lysates from MCF-10A cells left untreated or stimulated with 100 ng/ml TRAIL for the indicated times were immunoprecipitated with anti-caspase-8 antibody. The precipitates were immunoblotted with the indicated antibodies.

FIGS. 9A-9D are a series of photographs of western blots as well as a series of schematic diagrams evidencing that MUC1-CD directly binds to caspase-8-p18.

FIG. 9A depicts the amino acid sequence for human MUC1-CD (SEQ ID NO:2). Phosphorylation sites and regions for β-catenin, IKKβ and IKKγ binding are indicated by brackets of arrows (upper panel). GST (glutathione-S-transferase) or GST-caspase-8 protein were incubated with purified His-MUC1-CD. The adsorbates and the input protein were immunoblotted with anti-His and anti-GST antibodies as indicated to the right of the photographs. The molecular weights of each of the proteins (in kilodaltons (kDa)) are indicated to the left of each of the photographs.

FIG. 9B is a schematic of caspase-8 depicting the N-terminal region containing the DEDs, and the p18 and p10 fragments (upper panel). GST and the indicated GST-caspase-8 fragments were incubated with His-MUC1-CD. The adsorbates and input protein were immunoblotted with anti-His and anti-GST antibodies as indicated to the right of the photographs.

FIG. 9C is a schematic of his-tagged caspasc-8 p18 fragment depicting the A, B, C and AB subfragments (upper panel). The shaded region denotes position of the His tag. GST or GST-MUC1-CD was incubated with the indicated His-caspase-8 proteins. The adsorbates and input proteins (1/10th that used in the reactions) were immunoblotted with anti-His and anti-GST antibodies as indicated to the right of the photographs.

FIG. 9D: GST or the indicated GST-MUC1-CD proteins were incubated with His-caspase-8-p18 (upper panel). The adsorbates were immunoblotted with anti-His and anti-GST antibodies. GST or GST-MUC1-CD(1-20) was incubated with His-caspase-8-p18 in the presence of increasing amounts of MUC1-CD(1-20) peptide (lower panel). The adsorbates were immunoblotted with anti-caspase-8 antibody as indicated to the right of the photographs. Input of the GST proteins was assessed by Coomassie blue staining.

FIG. 11A: MCF-10A cells were transfected with the CsiRNA or MUC1siRNA pools for 72 hours and then incubated with Flag-TRAIL. Anti-Flag immune complexes were precipitated with protein-G-sepharose to isolate the DISC and then immunoblotted with the indicated antibodies.

FIG. 11B: MCF-10A cells were transfected with a control siRNA or FADDsiRNA for 72 h and then incubated with Flag-TRAIL to isolate the DISC. Anti-Flag precipitates were immunoblotted with anti-MUC1-C (upper panel). Whole cell lysates (WCL) were immunoblotted with anti-FADD antibody to confirm FADD silencing (lower panel).

FIGS. 11C and 11D: MCF-10A (FIG. 11C) and MCF-7 (FIG. 11D) cells were incubated with TRAIL and then immunoprecipitated with a control IgG or anti-FADD. Immune complexes were immunoblotted with the indicated antibodies. The molecular weights of each of the proteins (in kilodaltons (kDa)) are indicated to the left of each of the photographs.

FIG. 12A: GST and the indicated GST-MUC1-CD proteins were incubated with purified FADD. The adsorbates and input FADD were immunoblotted with anti-FADD antibody. The GST and GSTMUC1-CD proteins were stained with Coomassie blue.

FIG. 12B: Schematic representation of full length FADD, N-FADD and C-FADD with positioning of the DED and DD (upper panel). The indicated GST or GST-FADD proteins were incubated with purified MUC1-CD. The adsorbates and input MUC1-CD were immunoblotted with anti-MUC1-C (lower panel). Input of the GST and GST-FADD proteins was assessed with Coomassie blue staining.

FIG. 12C: GST or GST-caspase-8(1-183) containing the DEDs was incubated with FADD in the absence or presence of increasing amounts of purified MUC1-CD. The adsorbates and input FADD were immunoblotted with anti-FADD antibody. Input of GST and GST-caspase-8(1-183) was determined by Coomassie blue staining. Input of MUC1-CD was determined by immunoblotting.

The molecular weights of each of the proteins (in kilodaltons (kDa)) are indicated to the left of each of the photographs.

Figures 12A, 12B:
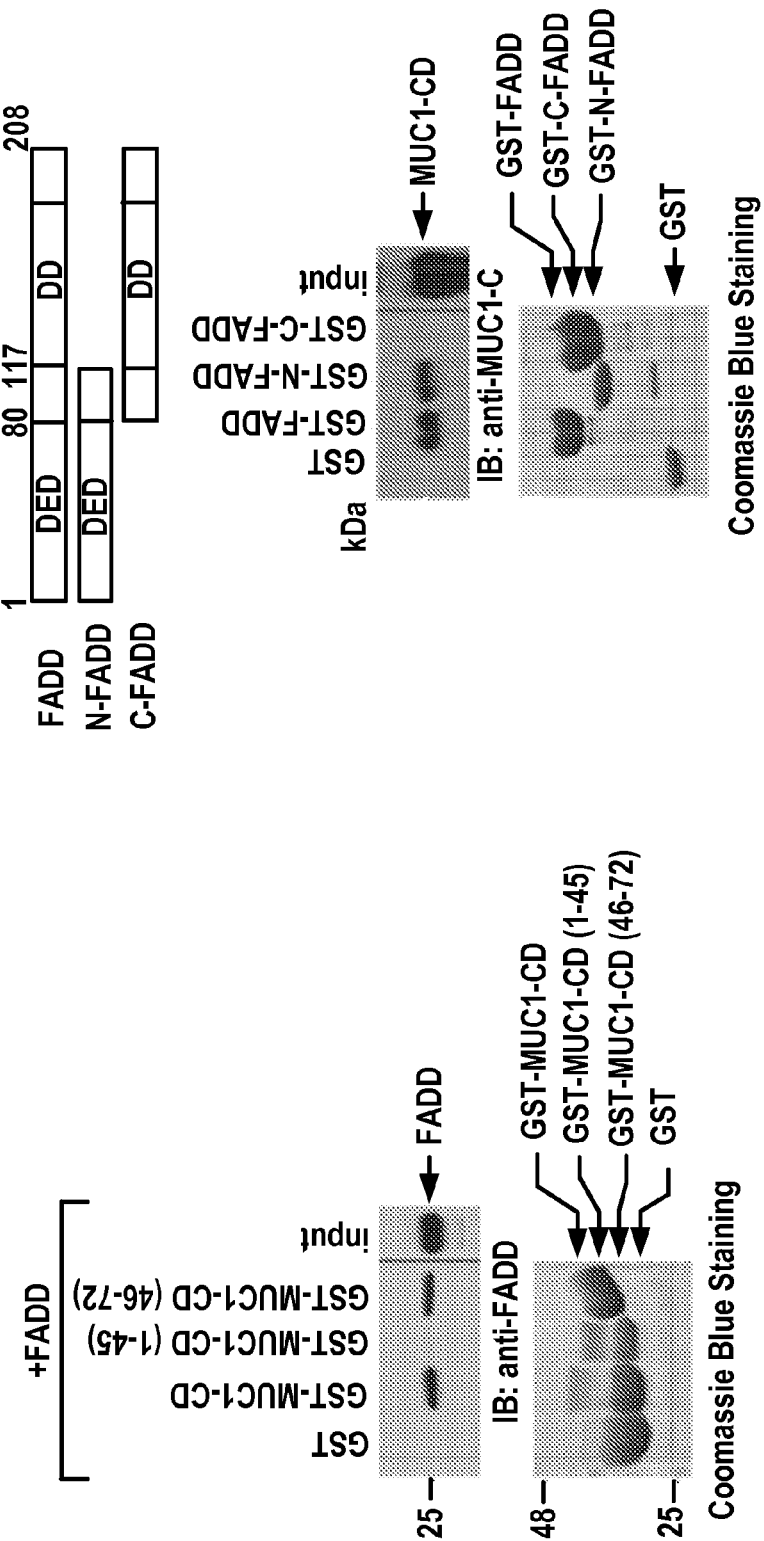
FIGS. 12A-12D are a series of photographs of western blots and a pair of schematic diagrams (FIGS. 12B and 12D) evidencing that MUC1-CD competes with caspasc-8 for direct binding to the FADD DED.
Figure 12C:
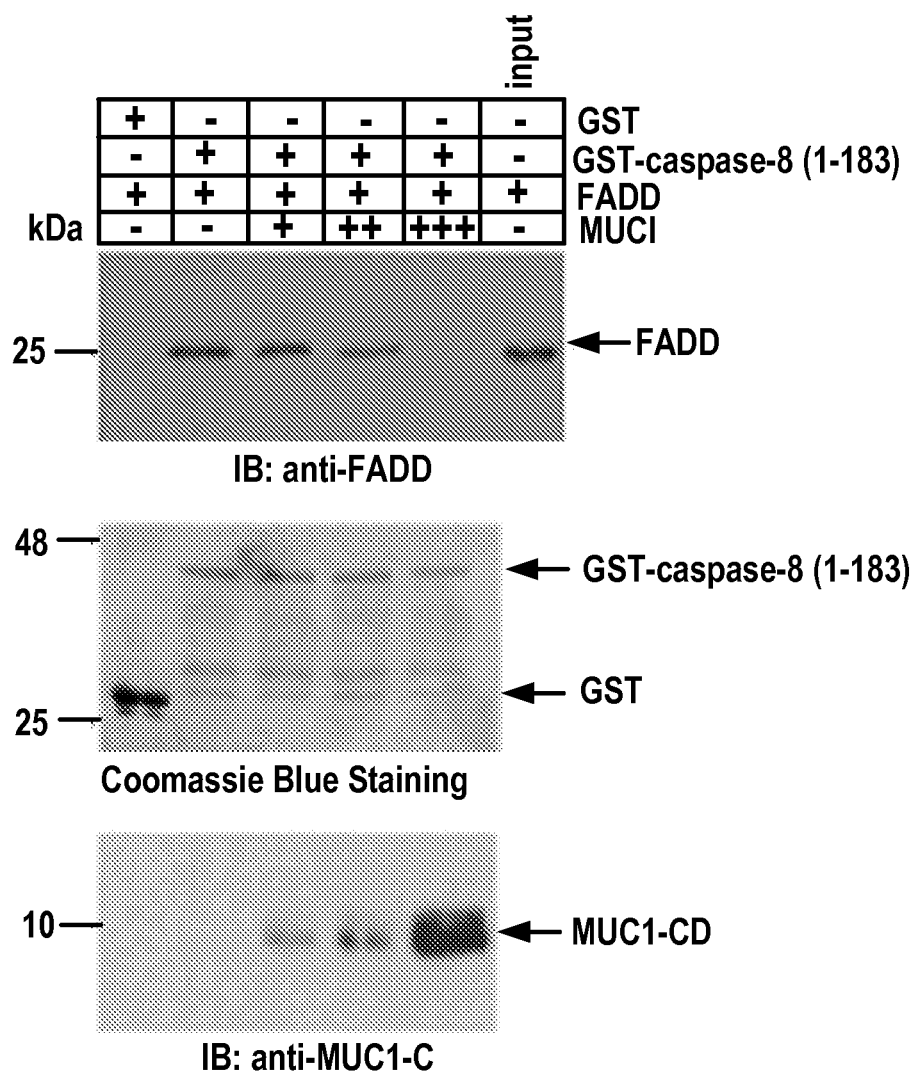
Figure 12D:
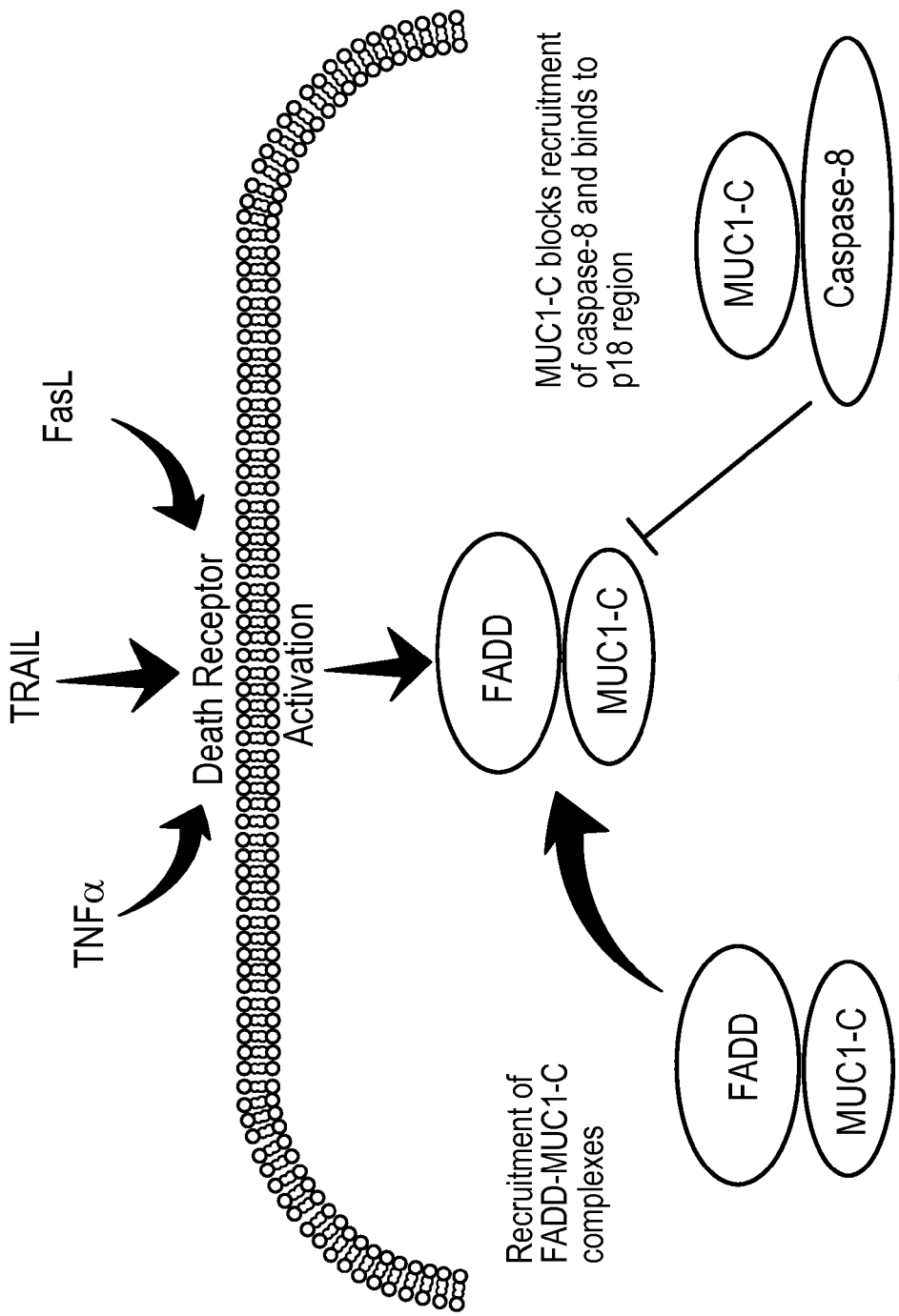

FIG. 12D: Proposed interactions of MUC1-C with FADD and caspase-8 in blocking death receptor signaling. While this schematic diagram indicates a proposed mechanism of action, the invention embodied by the present disclosure is not limited by any particular mechanism of action.

DETAILED DESCRIPTION

The disclosure features a variety of compositions and methods for modulating an interaction between MUC1 and caspasc-8 and/or an interaction between MUC1 and a DED-containing protein (e.g., FADD or any of the DED-containing proteins described herein). Such methods and compositions are useful for the treatment or prevention of, e.g., a variety of pathological disorders characterized by elevated or decreased levels of apoptosis. Moreover, the compositions and methods are also useful to identify, design, and generate compounds that modulate the interactions. The compounds and/or pharmaceutical compositions containing the compounds can be used in the treatment of disease.

While in no way intended as limiting or exhaustive, exemplary compositions and methods, as well as applications in which the compositions and methods can be used are as follows.

Screening Methods

The present disclosure provides in vitro methods (e.g., "screening methods") for identifying compounds (e.g., small molecules or macromolecules) that modulate an interaction between caspase-8 (or a MUC1-binding fragment thereof (e.g., the p18 subunit of processed caspase-8)) and MUC1 (e.g., the MUC1-CD). These methods can be performed using: (a) isolated MUC1 reagents and isolated caspase-8 reagents; or (b) cells expressing a MUC1 reagent and a caspase-8 reagent.

The present disclosure also features in vitro methods (e.g., "screening methods") for identifying compounds (e.g., small molecules or macromolecules) that modulate an interaction between a DED-containing protein (or a MUC1-binding fragment thereof (e.g., a DED such as the DED of FADD)) and MUC1 (e.g., the MUC1-CD). These methods can be performed using: (a) isolated MUC1 reagents and isolated DED-containing protein reagents; or (b) cells expressing a MUC1 reagent and a DED-containing protein reagent.

The term "isolated" as applied to any of the polypeptide reagents described herein refers to a polypeptide, or a peptide fragment thereof, which either has no naturally-occurring counterpart or has been separated or purified from components which naturally accompany it, e.g., in tissues such as pancreas, liver, spleen, ovary, testis, muscle, joint tissue, neural tissue, gastrointestinal tissue or tumor tissue (e.g., breast cancer or colon cancer tissue), or body fluids such as blood, serum, or urine. Typically, the polypeptide or peptide fragment is considered "isolated" when it is at least 70%, by dry weight, free from the proteins and other naturally-occurring organic molecules with which it is naturally associated. A preparation of a reagent can be at least 80 (e.g., 81, 82, 83, 84, 85, 86, 87, 88, 89, 90, 91, 92, 93, 94, 95, 96, 97, 98, or 99 or more) % by dry weight, the reagent. Since a polypeptide that is chemically synthesized is, by its nature, separated from the components that naturally accompany it, a synthetic polypeptide reagent is "isolated."

An isolated polypeptide reagent can be obtained, for example, by extraction from a natural source (e.g., from tissues); by expression of a recombinant nucleic acid encoding the polypeptide; or by chemical synthesis. A polypeptide reagent that is produced in a cellular system different from the source from which it naturally originates is "isolated," because it will necessarily be free of components which naturally accompany it. The degree of isolation or purity can be measured by any appropriate method, e.g., column chromatography, polyacrylamide gel electrophoresis, or HPLC analysis. Methods for generating and purifying MUC1, caspase-8, and DED-containing protein reagents are known in the art and set forth in the accompanying working examples.

Prior to testing, any of the reagents described herein can undergo modification, e.g., phosphorylation or glycosylation, by methods known in the art.

In methods of screening for compounds that modulate binding of an isolated MUC1 reagent to an isolated caspase-8 reagent, for example, a MUC1 reagent is contacted with a caspase-8 reagent in the presence of one or more concentrations of a test compound and binding between the two reagents in the presence and absence of the test compound is detected, tested for, and/or measured. In such assays neither of the reagents need be detectably labeled. For example, by exploiting the phenomenon of surface plasmon resonance, the MUC1 reagent can be bound to a suitable solid substrate and a caspasc-8 reagent exposed to the substrate-bound MUC1 reagent in the presence and absence of the compound of interest. Binding of the caspase-8 reagent to the MUC1 reagent on the solid substrate results in a change in the intensity of surface plasmon resonance that can be detected qualitatively or quantitatively by an appropriate instrument, e.g., a Biacore apparatus (Biacore International AB, Rapsgatan, Sweden). It will be appreciated that the experiment can be performed in reverse, i.e., with the caspase-8 reagent bound to the solid substrate and the MUC1 reagent added to it in the presence of the test compound. It is understood that through routine adaptation of the foregoing description a skilled artisan can also screen for compounds that modulate an interaction between MUC1 and a DED-containing protein.

Moreover, assays to test for modulation (e.g., inhibition or enhancement) of binding to MUC1 can involve the use, for example, of: (a) a single MUC1-specific "detection" antibody that is detectably labeled; (b) an unlabeled MUC1-specific antibody and a detectably labeled secondary antibody; or (c) a biotinylated MUC1-specific antibody and detectably labeled avidin. In addition, combinations of these approaches (including "multi-layer" assays) familiar to those in the art can be used to enhance the sensitivity of assays. In these assays, the caspase-8 reagent (or DED-containing protein reagent) can be immobilized on a solid substrate such as a nylon or nitrocellulose membrane by, for example, "spotting" an aliquot of a sample containing the reagent onto a membrane or by blotting onto a membrane an electrophoretic gel on which the sample or an aliquot of the sample has been subjected to electrophoretic separation. Alternatively, the caspase-8 reagent can be bound to a plastic substrate (e.g., the plastic bottom of an ELISA (enzyme-linked immunosorbent assay) plate well) using methods known in the art. The substrate-bound reagent is then exposed to the MUC1 reagent in the presence and absence of the test compound. After incubating the resulting mixture for a period of time and at a temperature useful for the system of interest, the presence and/or amount of MUC1 reagent bound to the caspase-8 reagent on the solid substrate is then assayed using a detection antibody that binds to the MUC1 reagent and, where required, appropriate detectably labeled secondary antibodies or avidin. It will be appreciated that instead of binding the caspase-8 reagent to the solid substrate, the MUC1 reagent can be bound to it. In this case binding of the caspase-8 reagent to the substrate-bound MUC1 is tested by obvious adaptations of the method described above for substrate-bound caspase-8 reagent. It is understood that through routine adaptation of the foregoing description a skilled artisan can also screen for compounds that modulate an interaction between MUC1 and a DED-containing protein.

The disclosure also features "sandwich" assays. In these sandwich assays, instead of immobilizing reagents on solid substrates by the methods described above, an appropriate reagent can be immobilized on the solid substrate by, prior to exposing the solid substrate to the reagent, conjugating a "capture" reagent-specific antibody (polyclonal or mAb) to the solid substrate by any of a variety of methods known in the art. The reagent is then bound to the solid substrate by virtue of its binding to the capture antibody conjugated to the solid substrate. The procedure is carried out in essentially the same manner described above for methods in which the appropriate reagent is bound to the solid substrate by techniques not involving the use of a capture antibody. It is understood that in these sandwich assays, the capture antibody should not bind to the same epitope (or range of epitopes in the case of a polyclonal antibody) as the detection antibody. Thus, if a mAb is used as a capture antibody, the detection antibody can be either: (a) another mAb that binds to an epitope that is either completely physically separated from or only partially overlaps with the epitope to which the capture mAb binds; or (b) a polyclonal antibody that binds to epitopes other than or in addition to that to which the capture mAb binds. On the other hand, if a polyclonal antibody is used as a capture antibody, the detection antibody can be either: (a) a mAb that binds to an epitope that is either completely physically separated from or partially overlaps with any of the epitopes to which the capture polyclonal antibody binds; or (b) a polyclonal antibody that binds to epitopes other than or in addition to that to which the capture polyclonal antibody binds. Assays which involve the use of a capture and a detection antibody include sandwich ELISA assays, sandwich Western blotting assays, and sandwich immunomagnetic detection assays.

Suitable solid substrates to which the capture antibody can be bound include, without limitation, the plastic bottoms and sides of wells of microtiter plates, membranes such as nylon or nitrocellulose membranes, polymeric (e.g., without limitation, agarose, cellulose, or polyacrylamide) beads or particles.

Methods of detecting and/or for quantifying a detectable label depend on the nature of the label and are known in the art. Appropriate labels include, without limitation, radionuclides (e.g., $^{125}$I, $^{131}$I, $^{35}$S, $^{3}$H, $^{32}$P, or $^{14}$C), fluorescent reagents (e.g., fluorescein, rhodamine, or phycoerythrin), luminescent reagents (e.g., Qdot™ nanoparticles supplied by the Quantum Dot Corporation, Palo Alto, Calif.), compounds that absorb light of a defined wavelength, or enzymes (e.g., alkaline phosphatase or horseradish peroxidase). The products of reactions catalyzed by appropriate enzymes can be, without limitation, fluorescent, luminescent, or radioactive or they may absorb visible or ultraviolet light. Examples of detectors include, without limitation, x-ray film, radioactivity counters, scintillation counters, spectrophotometers, colorimeters, fluorometers, luminometers, and densitometers.

Candidate compounds can also be tested for their ability to modulate binding of MUC1 to caspase-8 or MUC1 to a DED-containing protein in cells. The cells can either naturally express an appropriate MUC1 reagent and/or a caspase-8 reagent of interest (i.e., the cells encode an endogenous MUC1 and/or caspase-8 gene, which can be expressed to yield a MUC1 and/or caspase-8 polypeptide or their functional fragments) or they can recombinantly express either or both reagents. The cells can be normal or malignant and of any histological type, e.g., without limitation, epithelial cells, fibroblasts, lymphoid cells, macrophages/monocytes, granulocytes, keratinocytes, neuronal cells, or muscle cells. Suitable cell lines include those recited in the examples, e.g., breast cancer or colon cancer cell lines. The test compound can be added to the solution (e.g., culture medium) containing the cells or, where the compound is a protein, the cells can recombinantly express it. The cells can optionally also be exposed to a stimulus of interest (e.g., TNFα, FasL, or TRAIL) prior to or after exposure of the cells to the compound. Following incubation of cells expressing the reagents of interest in the absence or presence of a compound (optionally at various concentrations), physical association between the reagents can be determined microscopically using appropriately labeled antibodies specific for both reagents, e.g., by confocal microscopy. Alternatively, the cells can be lysed under non-dissociating conditions and the lysates tested for the presence of physically associated reagents. Such methods include adaptions of those described using isolated reagents. For example, an antibody specific for one of the two reagents (reagent 1) can be bound to a solid substrate (e.g., the bottom and sides of the well of a microtiter plate or a nylon membrane). After washing away unbound antibody, the solid substrate with bound antibody is contacted with the cell lysate. Any reagent 1 in the lysate, bound or not bound to the second reagent (reagent 2), will bind to the antibody specific for reagent 1 on the solid substrate. After washing away unbound lysate components, the presence of reagent 2 (bound via reagent 1 and the antibody specific for reagent 1 to the solid substrate) is tested for using a detectably labeled antibody (see above) specific for reagent 2. Alternatively, reagent 1 can be immunoprecipitated with an antibody specific for reagent 1 and the immunoprecipitated material can be subjected to electrophoretic separation (e.g., by polyacrylamide gel electrophoresis performed under non-dissociating conditions). The electrophoretic gel can then be blotted onto a membrane (e.g., a nylon or a nitrocellulose membrane) and any reagent 2 on the membrane detected and/or measured with a detectably labeled antibody (see above) specific for reagent 2 by any of the above-described methods. It is understood that in the above-described assays, reagent 1 can be either the MUC1 reagent or the caspase-8 reagent or vice versa. The test compounds can bind to one or both of the MUC1 and caspase-8 reagents. It is understood that through routine adaptation of the foregoing description a skilled artisan can also screen for compounds that modulate an interaction between MUC1 and a DED-containing protein.

Exemplary MUC1 reagents for use in the methods described above can include MUC1 reagents that contain the MUC1-cytoplasmic domain (CD), e.g., the human MUC1-CD depicted by SEQ ID NO:2 (or a functional fragment of the MUC1-CD, e.g., amino acids 1-20 of the MUC1 as depicted in SEQ ID NO:3 or amino acids 46-72 of the MUC1-CD as depicted in SEQ ID NO:4).

Exemplary caspase-8 reagents for use in the methods described herein include, e.g., reagents comprising the p18 subunit of caspase-8 (e.g., amino-acids 270-322 of caspase-8 (e.g., SEQ ID NO:27 or SEQ ID NO:28)), Exemplary DED-containing protein reagents include, e.g., FADD or the DED of FADD (e.g., SEQ ID NO:8).

Screening assays can optionally be performed in formats that allow for rapid preparation, processing, and analysis of multiple reactions. This can be, for example, in multi-well assay plates (e.g., 96 wells or 386 wells). Stock solutions for various agents can be provided manually or robotically, and subsequent pipetting, diluting, mixing, distribution, washing, incubating, sample readout, data collection and/or analysis can be done robotically using commercially available analysis software, robotics, and detection instrumentation capable of detecting the signal generated from the assay. Examples of such detectors include, but are not limited to, spectrophotometers, luminometers, fluorimeters, and devices that measure radioisotope decay. Exemplary high-throughput cell-based assays (e.g., detecting modulation of an interaction between two proteins in a cell) can utilize ArrayScan® VTI HCS Reader or KineticScan® HCS Reader technology (Cellomics Inc., Pittsburgh, Pa.).

Methods of Designing and Producing Compounds

The present disclosure also relates to using MUC1 reagents, caspase-8 reagents, and DED-containing protein reagents to predict or design compounds that can interact with and potentially thereby modulate the interaction between these polypeptides. Such compounds would be useful to inhibit the ability of MUC1 to promote cell survival in cancer cells, or enhance the ability of MUC1 to promote cell survival in neuronal cells (e.g., neuronal cells affected by a neurodegenerative disorder). One of skill in the art would know how to use standard molecular modeling or other techniques to identify small molecules that would bind to "appropriate sites" on MUC1, caspase-8, and/or a DED-containing protein. One such example is provided in Park et al. (*Annual Review Immunology* (2007) 25:561-586). Generally, an "appropriate site" on a MUC1, caspase-8, or a DED-containing protein is a site directly involved in the physical interaction between the two molecule types. However, an "appropriate site" can also be an allosteric site, i.e., a region of the molecule not directly involved in a physical interaction with another molecule (and possibly even remote from such a "physical interaction" site) but to which binding of a compound results (e.g., by the induction in a conformational change in the molecule) in modulation of the binding of the molecule to another molecule.

By "molecular modeling" is meant quantitative and/or qualitative analysis of the structure and function of protein-protein physical interaction based on three-dimensional structural information and protein-protein interaction models. This includes conventional numeric-based molecular dynamic and energy minimization models, interactive computer graphic models, modified molecular mechanics models, distance geometry and other structure-based constraint models. Molecular modeling typically is performed using a computer and may be further optimized using known methods.

Methods of designing compounds that bind specifically (e.g., with high affinity) to the region of MUC1 that interacts with caspase-8 (i.e., the cytoplasmic domain of MUC1), the region of caspase-8 that binds to MUC1 (e.g., the p18 subunit of caspase-8), or the region of a DED-containing protein that binds to MUC1 (e.g., the DED such as the DED of FADD) typically are also computer-based, and involve the use of a computer having a program capable of generating an atomic model. Computer programs that use X-ray crystallography data are particularly useful for designing such compounds. Programs such as RasMol, for example, can be used to generate a three dimensional model of, e.g., the region of MUC1 that interacts with caspase-8 or the region of caspase-8 that binds to MUC1 and/or determine the structures involved in MUC1-capase-8 binding. Computer programs such as INSIGHT (Accelrys, Burlington, Mass.), GRASP (Anthony Nicholls, Columbia University), Dock (Molecular Design Institute, University of California at San Francisco), and Auto-Dock (Accelrys) allow for further manipulation and the ability to introduce new structures.

Compounds can be designed using, for example, computer hardware or software, or a combination of both. However, designing is preferably implemented in one or more computer programs executing on one or more programmable computers, each containing a processor and at least one input device. The computer(s) preferably also contain(s) a data storage system (including volatile and non-volatile memory and/or storage elements) and at least one output device. Program code is applied to input data to perform the functions described above and generate output information. The output information is applied to one or more output devices in a known fashion. The computer can be, for example, a personal computer, microcomputer, or work station of conventional design.

Each program is preferably implemented in a high level procedural or object oriented programming language to communicate with a computer system. However, the programs can be implemented in assembly or machine language, if desired. In any case, the language can be a compiled or interpreted language.

Each computer program is preferably stored on a storage media or device (e.g., ROM or magnetic diskette) readable by a general or special purpose programmable computer. The computer program serves to configure and operate the computer to perform the procedures described herein when the program is read by the computer. The method described herein can also be implemented by means of a computer-readable storage medium, configured with a computer program, where the storage medium so configured causes a computer to operate in a specific and predefined manner to perform the functions described herein.

For example, the computer-requiring steps in a method of designing a compound can involve:

(a) inputting into an input device, e.g., through a keyboard, a diskette, or a tape, data (e.g. atomic coordinates) that define the three-dimensional (3-D) structure of a first molecule (e.g., MUC1 or a part of MUC1) that binds to a second molecule (e.g., caspase-8 or DED-containing protein or a part thereof) or a molecular complex (e.g., MUC1, or a part thereof, bound to caspase-8 or a DED-containing protein, or a part thereof, or MUC1 bound to a macromolecular caspase-8 or DED-containing complex), e.g., a region of MUC1 that interacts with caspase-8 or a DED-containing protein (i.e., the cytoplasmic domain of MUC1), the region of caspase-8 that binds to MUC1 (i.e., the p18 subunit of caspase-8), or all or a part (e.g., the cytoplasmic domain) of MUC1 bound to all or a part of caspasc-8 or a DED-containing protein; and (b) determining, using a processor, the 3-D structure (e.g., an atomic model) of: (i) the site on the first molecule involved in binding to the second molecule; or (ii) one or more sites on the molecular components of molecular complex of interaction between molecular components of the molecular complex.

From the information obtained in this way, one skilled in the art will be able to design and make modulatory (e.g., inhibitory or enhancing) compounds (e.g., peptides, non-peptide small molecules, aptamers (e.g., nucleic acid aptamers) with the appropriate 3-D structure).

Moreover, if computer-usable 3-D data (e.g., x-ray crystallographic or nuclear magnetic resonance (NMR) data) for a candidate compound are available, the following computer-based steps can be performed in conjunction with computer-based steps (a) and (b) described above: (c) inputting into an input device, e.g., through a keyboard, a diskette, or a tape, data (e.g. atomic coordinates) that define the three-dimensional (3-D) structure of a candidate compound; (d) determining, using a processor, the 3-D structure (e.g., an atomic model) of the candidate compound; (e) determining, using the processor, whether the candidate compound binds to the site on the first molecule or the one or more sites on the molecular components of the molecular complex; and (f) identifying the candidate compound as a compound that modulates the interaction between the first and second molecule or the between the molecular components of the molecular complex.

The method can involve the additional step of outputting to an output device a model of the 3-D structure of the compound. In addition, the 3-D data of candidate compounds can be compared to a computer database of, for example, 3-D structures (e.g., of MUC1, the cytoplasmic domain of MUC1, caspase-8, a MUC1-interacting fragment of caspase-8, a DED-containing protein or a MUC1-interacting fragment of a DED-containing protein) stored in a data storage system.

Compounds useful for the methods described herein also may be interactively designed from structural information of the compounds described herein using other structure-based design/modeling techniques (see, e.g., Jackson (1997) *Seminars in Oncology* 24:L164-172; and Jones et al. (1996) *J. Med. Chem.* 39:904-917, the disclosures of which are incorporated herein by reference in their entirety). Compounds and polypeptides can also be identified by, for example, identifying candidate compounds by computer modeling as fitting spatially and preferentially (i.e., with high affinity) into the appropriate acceptor sites on MUC1, caspase-8, or FADD.

Candidate compounds identified as described above can then be tested in standard cellular or cell-free binding or binding inhibition or enhancement assays familiar to those skilled in the art. Exemplary assays are described herein.

A candidate compound whose presence requires at least 2-fold (e.g., 4-fold, 6-fold, 10-fold, 100-fold, 1000-fold, 10,000 fold, or 100,000-fold) more of a given MUC1 reagent to achieve a defined arbitrary level of binding to a fixed amount of a caspase-8 or DED-containing protein reagent than is achieved in the absence of the compound can be useful for modulating the interaction between MUC1 and the relevant caspase-8 or DED-containing protein, and thus can be useful as, e.g., a cancer therapeutic or prophylactic agent. Alternatively, a candidate compound whose presence requires at least 2-fold (e.g., 2-fold, 4-fold, 6-fold, 10-fold, 100-fold, 1000-fold, 10,000 fold, or 100,000-fold) more of a given caspase-8 or DED-containing protein reagent to achieve a defined arbitrary level of binding to a fixed amount of a MUC1 reagent than is achieved in the absence of the compound can be useful for modulating the interaction between MUC1 and the relevant caspasc-8 or DED-containing protein, and thus can be useful as a cancer therapeutic or prophylactic agent.

The 3-D structure of biological macromolecules (e.g., proteins, nucleic acids, carbohydrates, and lipids) can be determined from data obtained by a variety of methodologies. These methodologies, which have been applied most effectively to the assessment of the 3-D structure of proteins, include: (a) x-ray crystallography; (b) nuclear magnetic resonance (NMR) spectroscopy; (c) analysis of physical distance constraints formed between defined sites on a macromolecule, e.g., intramolecular chemical crosslinks between residues on a protein (e.g., International Patent Application No. PCT/US00/14667, the disclosure of which is incorporated herein by reference in its entirety), and (d) molecular modeling methods based on a knowledge of the primary structure of a protein of interest, e.g., homology modeling techniques, threading algorithms, or ab initio structure modeling using computer programs such as MONSSTER (Modeling Of New Structures from Secondary and Tertiary Restraints) (see, e.g., International Application No. PCT/US99/11913, the disclosure of which is incorporated herein by reference in its entirety). Other molecular modeling techniques may also be employed in accordance with the methods described herein [e.g., Cohen et al. (1990) *J. Med. Chem.* 33: 883-894; Navia et al (1992) *Current Opinions in Structural Biology* 2, pp. 202-210, the disclosures of which are incorporated herein by reference in its entirety]. All these methods produce data that are amenable to computer analysis. Other spectroscopic methods that can also be useful in the methods described herein, but that do not currently provide atomic level structural detail about biomolecules, include circular dichroism and fluorescence and ultraviolet/visible light absorbance spectroscopy. A preferred method of analysis is x-ray crystallography. Descriptions of this procedure and of NMR spectroscopy are provided below.

X-Ray Crystallography

X-ray crystallography is based on the diffraction of x-radiation of a characteristic wavelength by electron clouds surrounding the atomic nuclei in a crystal of a molecule or molecular complex of interest. The technique uses crystals of purified biological macromolecules or molecular complexes (but these frequently include solvent components, co-factors, substrates, or other ligands) to determine near atomic resolution of the atoms making up the particular biological macromolecule. A prerequisite for solving 3-D structure by x-ray crystallography is a well-ordered crystal that will diffract x-rays strongly. The method directs a beam of x-rays onto a regular, repeating array of many identical molecules so that the x-rays are diffracted from the array in a pattern from which the structure of an individual molecule can be retrieved. Well-ordered crystals of, for example, globular protein molecules are large, spherical or ellipsoidal objects with irregular surfaces. The crystals contain large channels between the individual molecules. These channels, which normally occupy more than one half the volume of the crystal, are filled with disordered solvent molecules, and the protein molecules are in contact with each other at only a few small regions. This is one reason why structures of proteins in crystals are generally the same as those of proteins in solution.

Methods of obtaining the proteins of interest are described below. The formation of crystals is dependent on a number of different parameters, including pH, temperature, the concentration of the biological macromolecule, the nature of the solvent and precipitant, as well as the presence of added ions or ligands of the protein. Many routine crystallization experiments may be needed to screen all these parameters for the combinations that give a crystal suitable for x-ray diffraction analysis. Crystallization robots can automate and speed up work of reproducibly setting up a large number of crystallization experiments (see, e.g., U.S. Pat. No. 5,790,421, the disclosure of which is incorporated herein by reference in its entirety). Polypeptide crystallization occurs in solutions in which the polypeptide concentration exceeds it's solubility maximum (i.e., the polypeptide solution is supersaturated). Such solutions may be restored to equilibrium by reducing the polypeptide concentration, preferably through precipitation of the polypeptide crystals. Often polypeptides may be induced to crystallize from supersaturated solutions by adding agents that alter the polypeptide surface charges or perturb the interaction between the polypeptide and bulk water to promote associations that lead to crystallization.

Crystallizations are generally carried out between 4° C. and 20° C. Substances known as "precipitants" are often used to decrease the solubility of the polypeptide in a concentrated solution by forming an energetically unfavorable precipitating depleted layer around the polypeptide molecules [Weber (1991) *Advances in Protein Chemistry* 41:1-36]. In addition to precipitants, other materials are sometimes added to the polypeptide crystallization solution. These include buffers to adjust the pH of the solution and salts to reduce the solubility of the polypeptide. Various precipitants are known in the art and include the following: ethanol, 3-ethyl-2-4 pentanediol, and many of the polyglycols, such as polyethylene glycol (PEG). The precipitating solutions can include, for example, 13-24% PEG 4000, 5-41% ammonium sulfate, and 1.0-1.5 M sodium chloride, and a pH ranging from 5-7.5. Other additives can include 0.1 M Hepes, 2-4% butanol, 0.1 M or 20 mM sodium acetate, 50-70 mM citric acid, 120-130 mM sodium phosphate, 1 mM ethylene diamine tetraacetic acid (EDTA), and 1 mM dithiothreitol (DTT). These agents are prepared in buffers and are added dropwise in various combinations to the crystallization buffer.

Commonly used polypeptide crystallization methods include the following techniques: batch, hanging drop, seed initiation, and dialysis. In each of these methods, it is important to promote continued crystallization after nucleation by maintaining a supersaturated solution. In the batch method, polypeptide is mixed with precipitants to achieve supersaturation, and the vessel is sealed and set aside until crystals appear. In the dialysis method, polypeptide is retained in a sealed dialysis membrane that is placed into a solution containing precipitant. Equilibration across the membrane increases the polypeptide and precipitant concentrations, thereby causing the polypeptide to reach supersaturation levels.

In the preferred hanging drop technique [McPherson (1976) *J. Biol. Chem.*, 251:6300-6306], an initial polypeptide mixture is created by adding a precipitant to a concentrated polypeptide solution. The concentrations of the polypeptide and precipitants are such that, in this initial form, the polypeptide does not crystallize. A small drop of this mixture is placed on a glass slide that is inverted and suspended over a reservoir of a second solution. The system is then sealed. Typically, the second solution contains a higher concentration of precipitant or other dehydrating agent. The difference in the precipitant concentrations causes the protein solution to have a higher vapor pressure than the second solution. Since the system containing the two solutions is sealed, an equilibrium is established, and water from the polypeptide mixture transfers to the second solution. This equilibrium increases the polypeptide and precipitant concentration in the polypeptide solution. At the critical concentration of polypeptide and precipitant, a crystal of the polypeptide may form.

Another method of crystallization introduces a nucleation site into a concentrated polypeptide solution. Generally, a concentrated polypeptide solution is prepared and a seed crystal of the polypeptide is introduced into this solution. If the concentrations of the polypeptide and any precipitants are correct, the seed crystal will provide a nucleation site around which a larger crystal forms.

Yet another method of crystallization is an electrocrystallization method in which use is made of the dipole moments of protein macromolecules that self-align in the Helmholtz layer adjacent to an electrode (see, e.g., U.S. Pat. No. 5,597,457, the disclosure of which is incorporated herein by reference in its entirety).

Some proteins may be recalcitrant to crystallization. However, several techniques are available to the skilled artisan to induce crystallization. For example, the removal of flexible polypeptide segments at the amino or carboxyl terminal end of the protein may facilitate production of crystalline protein samples. Removal of such segments can be done using molecular biology techniques or treatment of the protein with proteases such as trypsin, chymotrypsin, or subtilisin.

In diffraction experiments, a narrow and parallel beam of x-rays is taken from the x-ray source and directed onto the crystal to produce diffracted beams. The incident primary beams cause damage to both the macromolecule and solvent molecules. The crystal is, therefore, cooled (e.g., to −220° C. to −50° C.) to prolong its lifetime. The primary beam must strike the crystal from many directions to produce all possible diffraction spots, so the crystal is rotated in the beam during the experiment. The diffracted spots are recorded on a film or by an electronic detector. Exposed film has to be digitized and quantified in a scanning device, whereas the electronic detectors feed the signals they detect directly into a computer. Electronic area detectors significantly reduce the time required to collect and measure diffraction data. Each diffraction beam, which is recorded as a spot on film, is defined by three properties: the amplitude, which is measured from the intensity of the spot; the wavelength, which is set by the x-ray source; and the phase, which is lost in x-ray experiments. All three properties are needed for all of the diffracted beams in order to determine the positions of the atoms giving rise to the diffracted beams. One way of determining the phases is called Multiple Isomorphous Replacement (MIR), which requires the introduction of exogenous x-ray scatterers (e.g., heavy atoms such metal atoms) into the unit cell of the crystal. For a more detailed description of MIR, see U.S. Pat. No. 6,093,573 (column 15) the disclosure of which is incorporated herein by reference in its entirety.

Atomic coordinates refer to Cartesian coordinates (x, y, and z positions) derived from mathematical equations involving Fourier synthesis of data derived from patterns obtained via diffraction of a monochromatic beam of x-rays by the atoms (scattering centers) of biological macromolecule of interest in crystal form. Diffraction data are used to calculate electron density maps of repeating units in the crystal (unit cell). Electron density maps are used to establish the positions (atomic coordinates) of individual atoms within a crystal's unit cell. The absolute values of atomic coordinates convey spatial relationships between atoms because the absolute values ascribed to atomic coordinates can be changed by rotational and/or translational movement along x, y, and/or z axes, together or separately, while maintaining the same relative spatial relationships among atoms. Thus, a biological macromolecule (e.g., a protein) whose set of absolute atomic coordinate values can be rotationally or translationally adjusted to coincide with a set of prior determined values from an analysis of another sample is considered to have the same atomic coordinates as those obtained from the other sample.

Further details on x-ray crystallography can be obtained from co-pending U.S. application Ser. No. 10/486,278, U.S. Pat. No. 6,093,573 and International Application Nos. PCT/US99/18441, PCT/US99/11913, and PCT/US00/03745. The disclosures of all these patent documents are incorporated herein by reference in their entirety.

NMR Spectroscopy

While x-ray crystallography requires single crystals of a macromolecule of interest, NMR measurements are carried out in solution under near physiological conditions. However, NMR-derived structures are not as detailed as crystal-derived structures.

While the use of NMR spectroscopy was until relatively recently limited to the elucidation of the 3-D structure of relatively small molecules (e.g., proteins of 100-150 amino acid residues), recent advances including isotopic labeling of the molecule of interest and transverse relaxation-optimized spectroscopy (TROSY) have allowed the methodology to be extended to the analysis of much larger molecules, e.g., proteins with a molecular weight of 110 kDa [Wider (2000) *BioTechniques* 29:1278-1294].

NMR uses radio-frequency radiation to examine the environment of magnetic atomic nuclei in a homogeneous magnetic field pulsed with a specific radio frequency. The pulses perturb the nuclear magnetization of those atoms with nuclei of nonzero spin. Transient time domain signals are detected as the system returns to equilibrium. Fourier transformation of the transient signal into a frequency domain yields a one-dimensional NMR spectrum. Peaks in these spectra represent chemical shifts of the various active nuclei. The chemical shift of an atom is determined by its local electronic environment. Two-dimensional NMR experiments can provide information about the proximity of various atoms in the structure and in three dimensional space. Protein structures can be determined by performing a number of two- (and sometimes 3- or 4-) dimensional NMR experiments and using the resulting information as constraints in a series of protein folding simulations.

More information on NMR spectroscopy including detailed descriptions of how raw data obtained from an NMR experiment can be used to determine the 3-D structure of a macromolecule can be found in: *Protein NMR Spectroscopy, Principles and Practice,* J. Cavanagh et al., Academic Press, San Diego, 1996; Gronenborn et al. (1990) *Anal. Chem.* 62(1):2-15; and Wider (2000), supra., the disclosures of all of which are incorporated herein by reference in their entirety Any available method can be used to construct a 3-D model of a region of MUC1 and/or caspase-8 or DED-containing protein of interest from the x-ray crystallographic and/or NMR data using a computer as described above. Such a model can be constructed from analytical data points inputted into the computer by an input device and by means of a processor using known software packages, e.g., HKL, MOSFILM, XDS, CCP4, SHARP, PHASES, HEAVY, XPLOR, TNT, NMRCOMPASS, NMRPIPE, DIANA, NMRDRAW, FELIX, VNMR, MADIGRAS, QUANTA, BUSTER, SOLVE, O, FRODO, or CHAIN. The model constructed from these data can be visualized via an output device of a computer, using available systems, e.g., Silicon Graphics, Evans and Sutherland, SUN, Hewlett Packard, Apple Macintosh, DEC, IBM, or Compaq.

Compounds

Compounds identified in any of the methods described herein, or any compound with appropriate activity useful in any of the methods described herein can include various chemical classes, though typically small organic molecules having a molecular weight in the range of 50 to 2,500 daltons. These compounds can comprise functional groups necessary for structural interaction with proteins (e.g., hydrogen bonding), and typically include at least an amine, carbonyl, hydroxyl, or carboxyl group, and preferably at least two of the functional chemical groups. These compounds often comprise cyclical carbon or heterocyclic structures and/or aromatic or polyaromatic structures (e.g., purine core) substituted with one or more of the above functional groups.

In alternative embodiments, compounds can also include biomolecules including, but not limited to, peptides, polypeptides, peptidomimetics (e.g., peptoids), amino acids, amino acid analogs, saccharides, fatty acids, steroids, purines, pyrimidines, derivatives or structural analogues thereof, polynucleotides, and polynucleotide analogs.

Candidate compounds can also include nucleic acids, for example, nucleic acids that inhibit the mRNA or protein expression of a protein (e.g., MUC1, caspase-8, or a DED-containing protein), for example, an antisense oligonucleotide that hybridizes to a MUC1 mRNA transcript, or a MUC1-specific small interference RNA (siRNA). Antisense oligonucleotides hybridize to a target transcript (e.g., an mRNA encoding an MUC1 protein) and have the effect in the cell of inhibiting expression of a protein produced from the transcript (e.g., a MUC1 protein). siRNAs homologous to a MUC1, caspase-8, or DED-containing protein coding sequences can be also used to reduce expression of a the corresponding protein in a cell. Exemplary MUC1-specific siRNAs (e.g., useful as positive controls in assays described herein) are set forth in the accompanying Examples.

Candidate compounds also include aptamers, which are relatively short nucleic acid (DNA, RNA or a combination of both) sequences that bind with high avidity to a variety of proteins and modulate the binding to such proteins of ligands, receptors, and other molecules. Aptamers are generally about 25-40 nucleotides in length and have molecular weights in the range of about 18-25 kDa. Aptamers with high specificity and affinity for targets can be obtained by an in vitro evolutionary process termed SELEX (systemic evolution of ligands by exponential enrichment) [see, for example, Zhang et al. (2004) Arch. Immunol. Ther. Exp. 52:307-315, the disclosure of which is incorporated herein by reference in its entirety]. For methods of enhancing the stability (by using nucleotide analogs, for example) and enhancing in vivo bioavailability (e.g., in vivo persistence in a subject's circulatory system) of nucleic acid aptamers see, for example, Zhang et al. (2004) supra and Brody et al. [(2000) Reviews in Molecular Biotechnology 74:5-13], the disclosure of which is incorporated herein by reference in its entirety.

Compounds can be identified from a number of potential sources, including: chemical libraries, natural product libraries, and combinatorial libraries comprised of random peptides, oligonucleotides, or organic molecules. Chemical libraries consist of random chemical structures, some of which are analogs of known compounds or analogs or compounds that have been identified as "hits" or "leads" in other drug discovery screens, while others are derived from natural products, and still others arise from non-directed synthetic organic chemistry. Natural product libraries re collections of microorganisms, animals, plants, or marine organisms which are used to create mixtures for screening by: (1) fermentation and extraction of broths from soil, plant or marine microorganisms, or (2) extraction of plants or marine organisms. Natural product libraries include polypeptides, non-ribosomal peptides, and variants (non-naturally occurring) thereof. For a review, see *Science* 282:63-68 (1998). Combinatorial libraries are composed or large numbers of peptides, oligonucleotides, or organic compounds as a mixture. These libraries are relatively easy to prepare by traditional automated synthesis methods, PCR, cloning, or proprietary synthetic methods. Of particular interest are non-peptide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers (1997) *Curr. Opin. Bioechnol.* 8:701-707.

Identification of test compounds through the use of the various libraries herein permits subsequent modification of the test compound "hit" or "lead" to optimize the capacity of the "hit" or "lead" to modulate the interaction between MUC1 and caspase-8 or MUC1 and a DED-containing protein.

In addition, the modulatory compounds can be antibodies, or antigen-binding antibody fragments, specific for MUC1, caspase-8, or a DED-containing protein. Such antibodies will generally bind to, or close to: (a) the region of MUC1 to which caspase-8 or a DED-containing protein binds; (b) or the region on caspase-8 or a DED-containing protein to which MUC1 binds. However, as indicated above, the compounds can also act allosterically and so they can also bind to the proteins at positions other than, and even remote from, the binding sites for MUC1 (on caspase-8 or a DED-containing protein) and on caspase-8 or a DED-containing protein (for MUC1). As used throughout the present application, the term "antibody" refers to a whole antibody (e.g., IgM, IgG, IgA, IgD, or IgE) molecule that is generated by any one of a variety of methods that are known in the art. The antibody can be made in or derived from any of a variety of species, e.g., mammals such as humans, non-human primates (e.g., monkeys, baboons, or chimpanzees), horses, cattle, pigs, sheep, goats, dogs, cats, rabbits, guinea pigs, gerbils, hamsters, rats, and mice.

The antibody can be a purified or a recombinant antibody. Also useful for the methods described herein are antibody fragments and chimeric antibodies and humanized antibodies made from non-human (e.g., mouse, rat, gerbil, or hamster) antibodies. As used herein, the term "antibody fragment" refers to an antigen-binding fragment, e.g., Fab, F(ab')$_2$, Fv, and single chain Fv (scFv) fragments. An scFv fragment is a single polypeptide chain that includes both the heavy and light chain variable regions of the antibody from which the scFv is derived. In addition, diabodies [Poljak (1994) *Structure* 2(12):1121-1123; Hudson et al. (1999) *J. Immunol. Methods* 23(1-2):177-189, the disclosures of both of which are incorporated herein by reference in their entirety] and intrabodies [Huston et al. (2001) *Hum. Antibodies* 10(3-4): 127-142; Wheeler et al. (2003) *Mol. Ther.* 8(3):355-366; Stocks (2004) *Drug Discov. Today* 9(22): 960-966, the disclosures of all of which are incorporated herein by reference in their entirety] can be used in the methods described herein.

Antibody fragments that contain the binding domain of the molecule can be generated by known techniques. For example: F(ab')$_2$ fragments can be produced by pepsin digestion of antibody molecules; and Fab fragments can be generated by reducing the disulfide bridges of F(ab')$_2$ fragments or by treating antibody molecules with papain and a reducing agent. See, e.g., National Institutes of Health, 1 *Current Protocols In Immunology*, Coligan et al., ed. 2.8, 2.10 (Wiley Interscience, 1991) the disclosure of which is incorporated herein by reference in its entirety. scFv fragments can be produced, for example, as described in U.S. Pat. No. 4,642, 334, the disclosure of which is incorporated herein by reference in its entirety.

Chimeric and humanized monoclonal antibodies can be produced by recombinant DNA techniques known in the art, for example, using methods described in Robinson et al., International Patent Publication PCT/US86/02269; Akira et al., European Patent Application 184,187; Taniguchi, European Patent Application 171,496; Morrison et al., European Patent Application 173,494; Neuberger et al., PCT Application WO 86/01533; Cabilly et al., U.S. Pat. No. 4,816,567; Cabilly et al., European Patent Application 125,023; Better et al. (1988) *Science* 240, 1041-43; Liu et al. (1987) *J. Immunol,*

139, 3521-26; Sun et al. (1987) *PNAS* 84, 214-18; Nishimura et al. (1987) *Canc. Res.* 47, 999-1005; Wood et al. (1985) *Nature* 314, 446-49; Shaw et al. (1988) *J. Natl. Cancer Inst.* 80, 1553-59; Morrison, (1985) *Science* 229, 1202-07; Oi et al. (1986) *BioTechniques* 4, 214; Winter, U.S. Pat. No. 5,225, 539; Jones et al. (1986) *Nature* 321, 552-25; Veroeyan et al. (1988) *Science* 239, 1534; and Beidler et al. (1988) *J. Immunol.* 141, 4053-60. The disclosures of all these articles and patent documents are incorporated herein by reference in their entirety.

The compounds identified above can be synthesized by any chemical or biological method. The compounds identified above can also be pure, or may be in a heterologous composition (e.g., a pharmaceutical composition), and can be prepared in an assay-, physiologic-, or pharmaceutically-acceptable diluent or carrier. This composition can also contain additional compounds or constituents which do not bind to or modulate the interaction between caspase-8 (or a DED-containing protein) and MUC1, but are useful in the application of various methods described herein (e.g., a composition may contain one or more additional therapeutic agents, see below).

Exemplary Compounds

The disclosure also features a peptide (e.g., an isolated peptide) consisting of, or consisting essentially of, an amino acid sequence that is identical, or at least 80% (e.g., 80%, 81%, 82%, 83%, 84%, 85%, 86%, 87%, 88%, 89%, 90%, or 95% or more) identical, to amino acids 1-20 of a MUC1-CD (e.g., amino acids 1-20 of human MUC1-CD having the sequence depicted in SEQ ID NO:2) such the amino acid sequence depicted in SEQ ID NO:3. The disclosure also features a peptide (e.g., an isolated peptide) consisting of, or consisting essentially of, an amino acid sequence that is identical, or at least 80% (e.g., 80%, 81%, 82%, 83%, 84%, 85%, 86%, 87%, 88%, 89%, 90%, or 95% or more) identical, to amino acids 46-72 of a MUC1-CD (e.g., amino acids 46-72 of human MUC1-CD having the sequence depicted in SEQ ID NO:2) such as the amino acid sequence depicted in SEQ ID NO:4. The disclosure also features a peptide (e.g., an isolated peptide) consisting of, or consisting essentially of, an amino acid sequence that is identical, or at least 80% (e.g., 80%, 81%, 82%, 83%, 84%, 85%, 86%, 87%, 88%, 89%, 90%, or 95% or more) identical, to amino acids 270-322 of caspase-8 (e.g., SEQ ID NO:27 or SEQ ID NO:28).

The peptides described herein are often referred to herein using the residue number of the N and C terminal amino acids of the peptides (e.g., amino acids 1-20 of the MUC1-CD or amino acids 270-322 of caspase-8) as the relevant sequences occur in the cytoplasmic domain of MUC1 or in full-length, unprocessed caspase-8. These peptides will frequently have identical sequences to the corresponding segments of the MUC1-CD (SEQ ID NO:2) or caspase-8 (SEQ ID NO:5). It is understood, however, that the fragments of the MUC1-CD (such as amino acids 1-20 or amino acids 46-72) can be peptide fragments of the MUC1-CD of a species other than human and that fragments of caspase-8 (such as amino acids 270-322 of human caspase-8) can be of a species other than human. As will be appreciated by those skilled in the art, the numbers of the N and C terminal amino acids of peptide fragments of such non-human polypeptides are not necessarily the same as those in the corresponding peptide fragments of human polypeptides. Moreover, the lengths and/or amino acids of peptide fragments of non-human polypeptides will not necessarily be the same as those in the corresponding peptide fragments of human polypeptides. Those of skill in the art will know how to establish the N and C terminal amino acids, the lengths, and amino acid sequences of peptides derived from non-human MUC1 or caspase-8 polypeptides. One useful method for doing this is sequence alignment and, in particular, maximum homology sequence alignment. Percent identity between two peptide sequences can be determined using a variety of algorithms and computer programs including, but not limited to, Clustal W (The European Bioinformatics Institute (EMBL-EBI), BLAST-Protein (National Center for Biotechnology Information (NCBI), United States National Institutes of Health), and PSAlign (University of Texas A&M; Sze et al. (2006) *Journal of Computational Biology* 13:309-319).

Also disclosed herein are variants of the human and non-human peptides described above. Variants of the human and non-human peptides described herein can include forms of the peptides having: (i) not more than 4 (e.g., 3, 2, or 1) amino acid substitutions (e.g., conservative or non-conservative substitutions); (ii) terminal or internal deletions; or (iii) terminal or internal additions, all of which are elaborated on herein.

The disclosure also features peptides consisting of, or consisting essentially of, an amino acid sequence of amino acids 1-20 of MUC1-CD (e.g., SEQ ID NO:3); amino acids 46-72 of MUC1-CD (e.g., SEQ ID NO:4); or amino acids 270-322 of caspase-8 (e.g., SEQ ID NO:27 or SEQ ID NO:28), but with not more than four (e.g., not more than three, not more than two, or not more than 1) substitutions. The substitutions can be, e.g., conservative or non-conservative (as described above).

Also featured are peptides comprising: a first amino acid sequence consisting essentially, or consisting, of amino acids 1-20 of MUC1-CD (e.g., SEQ ID NO:3); amino acids 46-72 of MUC1-CD (e.g., SEQ ID NO:4); or amino acids 270-322 of caspase-8 (e.g., SEQ ID NO:27 or SEQ ID NO:28); and a second amino acid sequence that is heterologous to the first amino acid sequence. The first amino acid sequence can have, e.g., not more than four substitutions (conservative or non-conservative substitutions or can be at least about 80%, 81%, 82%, 83%, 84%, 85%, 86%, 87%, 88%, 89%, 90%, or 95% or more) identical to SEQ ID NO:3, SEQ ID NO:4, or SEQ ID NO:27 or SEQ ID NO:28, respectively.

An amino acid sequence that is "heterologous" to a first amino acid sequence, or the term "heterologous amino acid sequence," is any amino acid sequence other than the amino acid sequence(s) flanking the first amino acid sequence as it occurs in nature. For example, two or more (e.g., two, three, four, five, six, seven, eight, nine, 10, 11, 12, 13, 14, 15, 16, 17, 18, 19, or 20 or more) and/or less than 20 (e.g., 19, 18, 17, 16, 15, 14, 13, 12, 11, 10, nine, eight, seven, six, five, four, three, two, or one) carboxy- and/or amino-terminal amino acid(s) immediately flanking SEQ ID NO:3 in a human MUC1-CD are not considered to be heterologous to SEQ ID NO:3. It is understood that a peptide containing a first amino acid sequence that is less than 100% identical to, or contains from one to four conservative substitutions in, an amino acid sequence of SEQ ID NO:3, SEQ ID NO:4, or SEQ ID NO:27 may not occur in nature at all.

In some embodiments, the second amino acid sequence can be a single amino acid. It is understood that an amino acid that is "heterologous" to a first amino acid sequence, or the term "heterologous amino acid," is any amino acid other than the amino acid(s) flanking the first amino acid sequence as it occurs in nature. For example, the two amino acid(s) immediately flanking SEQ ID NO:3 in human MUC1-CD are not considered to be heterologous to SEQ ID NO:3.

A heterologous sequence can be, for example, a sequence used for purification of the recombinant protein (e.g., FLAG, polyhistidine (e.g., hexahistidine), hemagluttanin (HA), glutathione-S-transferase (GST), or maltose-binding protein (MBP)). Heterologous sequences can also be proteins useful as diagnostic or detectable markers, for example, luciferase, green fluorescent protein (GFP), or chloramphenicol acetyl transferase (CAT). In some embodiments, the peptide can contain a signal sequence from another protein such as a KDEL (SEQ ID NO:30) sequence or any other described herein. In some embodiments, the peptides can contain all or part of an immunoglobulin molecule (e.g., all or part of an immunoglobulin heavy chain constant region; see below). In some embodiments, the peptide can contain a therapeutic or immune-stimulating polypeptide (e.g., a T helper epitope (e.g., a PADRE epitope or a Tetanus Toxoid universal T helper cell epitope) or all or part of a cytokine or chemokine) and/or a carrier (e.g., KLH) useful, e.g., in eliciting an immune response (e.g., for antibody generation). In some embodiments, the peptide can contain one or more linker peptide sequences (see below). The peptide can also contain a targeting polypeptide. Heterologous sequences can be of varying length and in some cases can be longer sequences than the first amino acid sequences to which the heterologous amino acid sequences are attached. It is understood that a peptide containing a first amino acid sequence and a second amino acid sequence that is heterologous to the first does not correspond in sequence to a naturally occurring protein.

Targeting polypeptides, as used herein, are polypeptides that target the moiety (or moieties) they are attached to (e.g., the first amino acid sequence) to specific tissues (e.g., to a lymph node) or cells (e.g., to an antigen presenting cell or other immune cell), or where in vitro, specific isolated molecules or molecular complexes. Targeting polypeptides can be, e.g., an antibody (immunoglobulin) or antigen binding fragment thereof or a ligand for a cell surface receptor. An antibody (or antigen-binding fragment thereof) can be, e.g., a monoclonal antibody, a polyclonal antibody, a humanized antibody, a fully human antibody, a single chain antibody, a chimeric antibody, or an Fab fragment, an F(ab')$_2$ fragment, an Fab' fragment, an Fv fragment, or an scFv fragment of an antibody. Antibody fragments that include, or are, Fc regions (with or without antigen-binding regions) can also be used to target the reagents to Fc receptor-expressing cells (e.g., antigen presenting cells such as interdigitating dendritic cells, macrophages, monocytes, or B cells). A ligand for a cell surface receptor can be, e.g., a chemokine, a cytokine (e.g., Interleukins 1, 2, 3, 4, 5, 6, 7, 8, 9, 10, 11, 12, 13, 14, 15, or 16), or a death receptor ligand (e.g., FasL or TNFα).

In some embodiments, the heterologous sequence can be, e.g., a "transportation sequence" that aids in the delivery of the peptide to the cell or to a specific compartment of a cell (e.g., the endoplasmic reticulum or Golgi apparatus). Transportation sequences can include, e.g., membrane translocating sequence, a transportan sequence, an antennapedia sequence, a cyclic integrin-binding peptide, and a Tat-mediated peptide, or modified versions thereof.

A linker peptide can connect the first amino acid sequence to one or more heterologous amino acid sequences. For example, a linker peptide can connect the first amino acid sequence to a second amino acid sequence. The linker peptide can, or contain, e.g., stretches of amino acids where at least four to six amino acids are glycine. (See, e.g., Mancebo et al. (1990) *Mol. Cell. Biol.* 10:2492-2502). A linker can also be, or contain, six or more (e.g., seven, eight, nine, 10, 11, or 12 or more) histidine residues. The linker peptide can contain, or be, at least one (e.g., one, two, three, four, five, six, seven, or eight or more) protease cleavage site(s). The protease sites can be, e.g., a trypsin, a chymotrypsin, or a factor Xa cleavage site. Such protease sites can be useful, e.g., to separate a first amino acid sequence from a heterologous sequence. For example, after expression and purification of a peptide containing a first amino acid sequence joined to a polyhistidine sequence (in this case used for purification) by a trypsin protease cleavage site, the polyhistidine sequence can be removed from first amino acid sequence by contacting the peptide with trypsin.

The first amino acid sequence and the second amino acid sequence can be associated with each other in a variety of ways. As used herein, "associated with" in the context of an interaction between two or more atoms or molecular units, includes any covalent or non-covalent bonding, or physical admixture, of two or more atoms or molecular units (e.g., a first amino acid sequence and a second amino acid sequence). The chemical nature of covalent bonds (two atoms sharing one or more pairs of valence electrons) are known in the art and include, e.g., disulfide bonds or peptide bonds. A non-covalent bond is a chemical bond between atoms or molecules that does not involve the sharing of pairs of valence electrons. For example, non-covalent interactions include, e.g., hydrophobic interactions, hydrogen-bonding interactions, ionic bonding, Van der Waals bonding, or dipole-dipole interactions. Examples of such non-covalent interactions include antibody-antigen complexing or binding pair interactions (interactions of a first and second member of a binding pair such as the interaction between streptavidin and biotin). It is understood that the term "associated with" (e.g., in the context of a first amino acid sequence and a second amino acid sequence) is thus coextensive with the term "comprising."

In some embodiments, a peptide containing a first amino acid sequence and a second amino acid sequence can be a fusion protein. For example, the first amino acid sequence and second amino acid sequence can be encoded by (and expressed as fusion protein from) a single nucleic acid sequence. In some instances, the first amino acid sequence and second amino acid sequence can be encoded by two or more (e.g., three, four, five, or six or more) different nucleic acid sequences. For example, the first amino acid sequence can be encoded by a first nucleic acid sequence and the second amino acid sequence can be encoded by a second nucleic acid sequence (see below under "Nucleic Acids and Methods for Producing the Peptides").

When expressed or produced separately, a first amino acid sequence and a second amino acid sequence can be cross-linked together using any of a number of known chemical cross linkers. Examples of such chemical cross-linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable chemical cross-linker, 4-succinimidyloxycarbonyl-α-methyl-α(2-pyridyldithio)toluene (SMPT), forms such a linkage between the two amino acid sequences utilizing a terminal lysine on one of the amino acid sequences and a terminal cysteine on the other. Heterobifunctional reagents which cross-link by a different coupling moiety on each amino acid sequence. In this way, the resulting "dimers" will be heterodimers (peptides containing the first and second amino acid sequences) rather than either homodimers (e.g., two first amino acid sequences or two second amino acid sequences) or a mixture of homodimers and heterodimers. Thus, the coupling moiety on a first amino acid sequence could be a cysteine residue and on the other a lysine residue. Other useful cross-linkers include, without limitation, chemicals that link two amino groups (e.g., N-5-Azido-2-nitrobenzoyloxysuccinimide), two sulfhydryl groups (e.g., 1,4-Bis-maleimidobutane) an amino group and a sulfhydryl group (e.g., m-Maleimidobenzoyl-N-hydroxysuccinimide ester), an amino group and a carboxyl group (e.g., 4-[p-Azidosalicylamido]butylamine), and an amino group and a guanadium group that is present in the side chain of arginine (e.g., p-Azidophenyl glyoxal monohydrate).

The coupling moieties will preferably be at the termini (C or N) of each amino acid sequence. They can be, as indicated above, a cysteine residue on each amino acid sequence, or a cysteine on one and a lysine on the other. Where they are two cysteine residues, cross-linking can be effected by, for example, exposing amino acid sequences to oxidizing conditions.

A peptide can contain a first amino acid sequence and a second amino acid sequence or the peptide can contain more than one (e.g., two, three, four, five, six, seven, or eight or more) additional heterologous amino acid sequences. The additional heterologous amino acid sequences can flank, or be joined to, the amino terminus and/or the carboxy-terminus of the first amino acid sequence.

Where more than two amino acid sequences are to be joined, at least one of the amino acid sequences can have more than one cross-linking moiety. For example, a first amino acid sequence can have a cross-linking moiety at the amino-terminus and carboxy-terminus. Such multimers can be constructed "sequentially." Thus, each amino acid sequence is joined to the next such that the terminal amino acid sequences in the chain only have one residue involved in an inter-domain (or inter-agent) bond while the "internal" amino acid sequence(s) each have two moieties involved in inter-domain bonds. Alternatively, one amino acid sequence (such as the first amino acid sequence) could be linked to multiple (e.g., 2, 3, 4, or 5) other amino acid sequences.

Also featured are peptide compositions comprising: a first component and a second component, wherein the first component consists of, or consists essentially of, an amino acid sequence of amino acids 1-20 of MUC1-CD (e.g., SEQ ID NO:3); amino acids 46-72 of MUC1-CD (e.g., SEQ ID NO:4); or amino acids 270-322 of caspase-8 (e.g., SEQ ID NO:27 or SEQ ID NO:28). The second component can be, e.g., a heterologous amino acid sequence (as described above), a detectable label (see below), a therapeutic agent, a diagnostic agent, or a prophylactic agent (see below). For example, a peptide composition can contain an amino acid sequence consisting of, or consisting essentially of, amino acids 1-20 of MUC1-CD (e.g., SEQ ID NO:3), amino acids 46-72 of MUC1-CD (e.g., SEQ ID NO:4), or amino acids 270-322 of caspase-8 (e.g., SEQ ID NO:27 or SEQ ID NO:28); and a detectable label such as a radionuclide.

It is understood that in some embodiments, a peptide of amino acids 1-20 of MUC1-CD (e.g., SEQ ID NO:3); amino acids 46-72 of MUC1-CD (e.g., SEQ ID NO:4); or amino acids 270-322 of caspase-8 (SEQ ID NO:27) can have at the amino-terminal end and/or carboxy-terminal end up to 200 (e.g., one, two, three, four, five, six, seven, eight, nine, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, or 200) amino acids that are heterologous or are present in the native protein.

Nucleic Acids and Methods for Producing Peptides.

The disclosure also features nucleic acid sequences (as well as nucleic acid vectors containing nucleic acid sequences) encoding, and methods for producing, one or more (e.g., one, two, three, four, five, six, seven, eight, nine, 10, 11, 12, 13, or 14) of any of the peptides described above.

Such methods can include the steps of: optionally, providing a cell (or group of cells) comprising a nucleic acid vector containing a nucleic acid sequence encoding one of more of any of the peptides described herein, the nucleic acid sequence being operably linked to an expression control sequence, and culturing the cell under conditions that permit the expression of the peptides. The methods can also include the step of isolating the one or more peptides from the cell, or from the medium in which the cell was cultured.

Suitable methods for constructing nucleic acid sequences and vectors (e.g., expression vectors) for recombinant expression of one or more of the peptides described herein are well known to those skilled in the art and described in, e.g., Sambrook et al., *Molecular Cloning: A Laboratory Manual* Second Edition vol. 1, 2 and 3. Cold Spring Harbor Laboratory Press: Cold Spring Harbor, N.Y., USA, November 1989, the disclosure of which is incorporated by reference in its entirety. The nucleic acids and vectors can be used, e.g., to express the peptides in a wide variety of host cells including, e.g., a bacterial, a yeast, or a mammalian cell. The nucleic acids and vectors can also be used in, e.g., in vivo and ex vivo methods as described below.

The peptide-coding sequences can be operably-linked to promoter and/or enhancer elements that direct the expression of the peptides encoded by the nucleic acids. Enhancers provide expression specificity in terms of time, location, and level. Unlike a promoter, an enhancer can function when located at variable distances from the transcription initiation site, provided a promoter is present. An enhancer can also be located downstream of the transcription initiation site or in an exon of the relevant gene. To bring a coding sequence under the control of a promoter, it is necessary to position the translation initiation site of the translational reading frame of the peptide between one and about fifty nucleotides downstream (3') of the promoter. Promoters of interest include, but are not limited to, the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3 phosphoglycerate kinase, the promoters of acid phosphatase, and the promoters of the yeast a mating factors, the adenoviral E1b minimal promoter, or the thymidine kinase minimal promoter. The DF3 enhancer can be particularly useful for expression of a compound in cells that naturally express MUC1 (and/or caspase-8 or a DED-containing protein), for example, normal epithelial cells or malignant epithelial cells (carcinoma cells), e.g., breast cancer cells (sec U.S. Pat. Nos. 5,565,334 and 5,874,415, the disclosures of which are incorporated herein by reference in their entirety). The coding sequence of the expression vector is operatively linked to a transcription terminating region.

The peptide-coding sequences, or vectors containing the peptide-coding sequences, can contain a leader sequence that encodes a signal peptide. The leader sequence can be at the 5' end of the sequence encoding one or more of the peptides described herein. The signal peptide can be immediately N-terminal of a given peptides or can be separated from it by one or more (e.g., 2, 3, 4, 6, 8, 10, 15 or 20) amino acids, provided that the leader sequence is in frame with the nucleic acid sequence encoding the peptides. The signal peptide, which is generally cleaved from the peptide prior to secretion (unless of course the signal peptide directs the insertion of a transmembrane protein), directs the peptide to which it is attached into the lumen of the host cell endoplasmic reticulum (ER) during translation and the peptides are then secreted, via secretory vesicles, into the environment of the host cell. Useful signal peptides include, e.g., native leader sequences of cytokines or growth factors, KDEL (SEQ ID NO:30), or any signal sequences described in, e.g., U.S. Pat. No. 5,827,516, the disclosure of which is incorporated herein by reference in its entirety.

In some embodiments, the 5' end of a peptide-coding sequence can include a non-native ATG "start sequence." That is, e.g., an ATG sequence can be added to a nucleic acid encoding a peptide to ensure that the peptide is properly transcribed and translated. Although a leader sequence generally includes an ATG start sequence, in embodiments where it does not, the ATG sequence can be added at the 5' end of a nucleic acid encoding the leader sequence.

Suitable methods for constructing peptide-coding sequences and expression vectors are well known to those skilled in the art and described in, e.g., Sambrook et al., *Molecular Cloning: A Laboratory Manual* Second Edition vol. 1, 2 and 3. Cold Spring Harbor Laboratory Press: Cold Spring Harbor, N.Y., USA, November 1989; the disclosure of which is incorporated herein by reference in its entirety.

A recombinant vector can be introduced into a cell using a variety of methods, which methods can depend, at least in part, on the type of cell into which the nucleic acid is introduced. For example, bacterial cells can be transformed using methods such as electroporation or heat shock. Methods for transfecting yeast cells include, e.g., the spheroplast technique or the whole-cell lithium chloride yeast transformation method (see, e.g., U.S. Pat. No. 4,929,555; Hinnen et al. (1978) *Proc. Nat. Acad. Sci. USA* 75:1929; Ito et al. (1983) *J. Bacteriol.* 153:163; U.S. Pat. No. 4,879,231; and Sreckrishna et al. (1987) *Gene* 59:115, the disclosures of each of which are incorporated herein by reference in their entirety). Transfection of animal cells can feature, for example, the introduction of a vector to the cells using calcium phosphate, electroporation, heat shock, liposomes, or transfection reagents such as FUGENE® or LIPOFECTAMINE®, or by contacting naked nucleic acid vectors with the cells in solution (see, e.g., Sambrook et al., supra).

Expression systems that can be used for small or large scale production of the peptides described herein include, but are not limited to, microorganisms such as bacteria (for example, *E. coli* and *B. subtilis*) transformed with recombinant bacteriophage DNA, plasmid DNA, or cosmid DNA expression vectors; fungus (e.g., yeast (for example, *Saccharomyces* and *Pichia*)) transformed with recombinant yeast expression vectors; insect cell systems infected with recombinant virus expression vectors (for example, baculovirus); plant cell systems infected with recombinant virus expression vectors (for example, cauliflower mosaic virus (CaMV) and tobacco mosaic virus (TMV)) or transformed with recombinant plasmid expression vectors (for example, Ti plasmid); or mammalian cell systems (for example, COS, CHO, BHK, 293, VERO, HeLa, MDCK, W138, and NIH 3T3 cells) harboring recombinant expression constructs containing promoters derived from the genome of mammalian cells (for example, the metallothionein promoter) or from mammalian viruses (for example, the adenovirus late promoter, a CMV promoter, an SV40 promoter, or the vaccinia virus 7.5K promoter). Also useful as host cells are primary or secondary cells obtained directly from a mammal, transfected with a plasmid vector or infected with a viral vector (e.g., viral vectors such as herpes viruses, retroviruses, vaccinia viruses, attenuated vaccinia viruses, canary pox viruses, adenoviruses and adeno-associated viruses, among others).

As described above, following the expression of any of the peptides described herein, the peptides can be isolated from the cultured cells, or from the media in which the cells were cultured, using standard techniques (see Sambrook et al., supra). Methods of isolating proteins are known in the art and include, e.g., liquid chromatography (e.g., HPLC), affinity chromatography (e.g., metal chelation or immunoaffinity chromatography), ion-exchange chromatography, hydrophobic-interaction chromatography, precipitation, or differential solubilization.

Smaller peptides (e.g., peptides having less than 200 (e.g., less than 175, less than 150, less than 125, less than 100, less than 90, less than 80, less than 70, or less than 60) amino acids) can be chemically synthesized by standard chemical means such as FMOC solid-phase synthesis.

The peptides described herein can, but need not, be isolated. The term "isolated," as applied to any of the peptides described herein, refers to a peptide, a fragment thereof, (or for compositions, a macromolecular complex), that has been separated or purified from components (e.g., proteins or other naturally-occurring biological or organic molecules) which naturally accompany it. It is understood that recombinant molecules (e.g., recombinant peptides) will always be "isolated." Typically, a peptide (or fragment or macromolecular complex) is isolated when it constitutes at least 60%, by weight, of the total molecules of the same type in a preparation, e.g., 60% of the total molecules of the same type in a sample. For example, a peptide described herein is considered isolated when it constitutes at least 60%, by weight, of the total protein in a preparation or sample. In some embodiments, a molecule in the preparation consists of at least 75%, at least 90%, or at least 99%, by weight, of the total molecules of the same type in a preparation.

Similarly, the peptide-coding sequences or vectors containing the peptide-coding sequences described herein can also be isolated. The term "isolated," as applied to any of the peptide-coding sequences or vectors described herein, refers to a peptide-coding sequence or vector, a fragment thereof that has been separated or purified from components (e.g., nucleic acids, proteins, or other naturally-occurring biological or organic molecules) which naturally accompany it. It is understood that recombinant molecules (e.g., recombinant vectors or peptide-coding sequences) will always be "isolated." Typically, a peptide-coding sequence or vector (or fragment thereof) is isolated when it constitutes at least 60%, by weight, of the total molecules of the same type in a preparation, e.g., 60% of the total molecules of the same type in a sample. For example, a peptide-coding sequence or vector described herein is considered isolated when it constitutes at least 60%, by weight, of the total nucleic acid in a preparation or sample. In some embodiments, a molecule in the preparation consists of at least 75%, at least 90%, or at least 99%, by weight, of the total molecules of the same type in a preparation.

In some embodiments, the isolated peptides, peptide-coding sequences, or vectors can be frozen, lyophilized, or immobilized and stored under appropriate conditions, which allow the molecules to retain activity such as the ability to inhibit an interaction between MUC1 and caspase-8 or MUC1 and a DED-containing protein.

Additional Processing of Peptides. Following the expression or synthesis of any of the peptides described herein, the peptides can be further processed. The further processing can include chemical or enzymatic modifications to peptides or, in cases where the peptides are modified, the processing can include enzymatic or chemical alterations of existing modifications, or both. The additional processing of the peptides can include the addition (covalent or non-covalent joining) of a heterologous amino acid sequence such as, but not limited to, any of the heterologous amino acid sequences described above. Enzymatic treatment can involve contacting a peptide with, e.g., one or more proteases, phosphatases, or kinases under conditions that allow the peptide to be modified. Enzymatic treatment can involve contacting a peptide with one or more enzymes (e.g., an oligosaccharyltransferase or a mannosidase) capable of glycosylating, or modifying the glycosylation of, the peptide.

The processing can include the addition of, e.g., a detectable label to a peptide. For example, a peptide can be detectably labeled with an enzyme (e.g., horseradish peroxidase, alkaline phosphatase, β-galactosidase, or acetylcholinesterase), a fluorescent material (e.g., umbelliferone, fluorescein, fluorescein isothiocyanate, rhodamine, dichlorotriazinylamine, fluorescein, dansyl chloride, allophycocyanin (APC), or phycoerythrin), a luminescent material (e.g., a lanthanide or chelate thereof), a bioluminescent material (e.g., luciferase, luciferin, or aequorin), or a radionuclide (e.g., $^3$H, $^{32}$P, $^{33}$P, $^{125}$I, or $^{35}$S).

The processing can also involve the coupling of the peptide to a polymer (e.g., a polyalkylene glycol moiety such as a polyethylene glycol moiety). In some embodiments, the polymer is coupled to the polypeptide at a site on the peptide that is an N terminus. In some embodiments, a peptide can contain one or more internal amino acid insertions that provide an internal polymer conjugation site to which a polymer can be conjugated.

Pharmaceutical Compositions and Methods of Treatment

The present disclosure also provides for pharmaceutical compositions comprising a therapeutically effective amount of a compound, or a pharmaceutically acceptable salt thereof together with a pharmaceutically acceptable carrier, diluent, or excipient therefor. A compound that has been screened by a method described herein and/or determined, for example, to (a) modulate an interaction between MUC1 and caspase-8 or modulate an interaction between MUC1 and a DED-containing protein, or modulate apoptosis in a cell can be considered a compound. Compounds can be optionally optimized and/or derivatized, and formulated with physiologically acceptable excipients to form pharmaceutical compositions.

Any of the compounds described herein can be incorporated into pharmaceutical compositions. Such compositions typically include the compound and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. A compound of described herein can be formulated as a pharmaceutical composition in the form of a syrup, an elixir, a suspension, a powder, a granule, a tablet, a capsule, a lozenge, a troche, an aqueous solution, a cream, an ointment, a lotion, a gel, an emulsion, etc. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. A parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contamination by microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of infections by microorganisms can be achieved by various antibacterial and antifungal agents, for example, parabens, chlorobutanol, phenol, ascorbic acid, thimerosal, and the like. In many cases, it will be desirable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the methods of preparation can include vacuum drying or freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The powders and tablets contain from 1% to 95% (w/w) of the active compound. In certain embodiments, the active compound ranges from 5% to 70% (w/w). Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, the disclosure of which is incorporated herein by reference in its entirety.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. Dosage units can also be accompanied by instructions for use.

The dose administered to a subject, in the context of the present disclosure, should be sufficient to affect a beneficial therapeutic response in the subject over time. Examples of subjects include, without limitation, humans or primates (e.g., chimpanzees, baboons, or monkeys), mice, rats, rabbits, guinea pigs, gerbils, hamsters, horses, livestock (e.g., cows, pigs, sheep, or goats), dogs, cats, or whales. In certain embodiments, the "subject" is a human (e.g., a human patient).

The dose will be determined by the efficacy of the particular compound employed and the condition of the subject, as well as the body weight or surface area of the subject to be treated. The size of the dose also will be determined by the existence, nature, and extent of any adverse side effects that accompany the administration of a particular compound in a particular subject. In determining the effective amount of the compound to be administered in the treatment or prophylaxis of the disease being treated, the physician can evaluate factors such as the circulating plasma levels of the compound, compound toxicities, and/or the progression of the disease, etc. In general, the dose equivalent of a compound is from about 1 μg/kg to 100 mg/kg for a typical subject. Many different administration methods are known to those of skill in the art.

For administration, compounds of the present disclosure can be administered at a rate determined by factors that can include, but are not limited to, the pharmacokinetic profile of the compound, contraindicated drugs, and the side effects of the compound at various concentrations, as applied to the mass and overall health of the subject. Administration can be accomplished via single or divided doses.

Toxicity and therapeutic efficacy of such compounds can be determined by known pharmaceutical procedures in cell cultures or experimental animals (animal models of cancer, inflammatory disorders, ischemic disorders, or neurodegenerative disorders). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue and to minimize potential damage to normal cells and, thereby, reduce side effects.

The data obtained from the cell culture assays and animal studies can be used in formulating a range of dosage for use in humans. The dosage of such compounds lies generally within a range of circulating concentrations that include the $ED_{50}$ with little or no toxicity. The dosage may vary within this range depending upon the dosage form employed and the route of administration utilized. For a compound used as described herein (e.g., for treating cancer, neurodegenerative disorder, ischemic disorder, or inflammatory condition in a subject), the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of a compound (i.e., an effective dosage) includes milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a compound depend upon the potency of the compound with respect to, e.g., inhibition of cell growth (e.g., inhibition of the growth of a cancer cell) or enhancement of cell viability (e.g., enhancement of the viability of a neuron affected by a neurodegenerative disorder). When one or more of these compounds is to be administered to an animal (e.g., a human) to treat an infection or a cancer, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated. One in the art will also appreciate that certain additional factors may influence the dosage and timing required to effectively treat a subject, including but not limited to the severity of the disease or disorder, previous treatments, and other diseases present. Moreover, treatment of a subject with a therapeutically effective amount of a compound (e.g., a protein, polypeptide, antibody, or nucleic acid) can include a single treatment or can include a series of treatments.

The pharmaceutical compositions can be included in a container, pack, or dispenser together with instructions for administration.

Methods for Modulating an Interaction

The disclosure features a variety of in vitro, in vivo, and ex vivo methods of modulating (e.g., inhibiting or enhancing) an interaction between MUC1 and caspase-8 or between MUC1 and a DED-containing protein. The findings described herein demonstrate, inter alia, that MUC1 blocks activation of caspase-8 and apoptosis in cancer cells exposed to tumor necrosis factor alpha (TNFα), TRAIL, and Fas ligand (FasL) and that MUC1 (i) interacts with caspase-8 and DED domain of Fas-associated death domain (FADD) in vivo and in vitro; (ii) competes with caspase-8 for binding to FADD; and (iii) inhibits the recruitment of caspase-8 to the death-inducing signaling complex (DISC). Thus, inhibition of these interactions can have general applicability in inhibiting the growth or viability of a cancer or an inflammatory cell. Inhibition of cell growth can be a reversible inhibition of cell growth, or more preferably can be an irreversible inhibition of cell growth (i.e., causing the death of the cell). In other embodiments, enhancement of the interactions can have general applicability in increasing the viability of a cell or cell population (e.g., a cell population in a brain tissue, a spinal cord tissue, or a heart tissue).

Where the methods of modulation are in vivo or ex vivo, such methods can also be useful in the treatment of conditions characterized by decreased levels of apoptosis (e.g., cancers, inflammatory conditions, viral infections, or certain developmental disorders) or conditions characterized by elevated levels of apoptosis (e.g., ischemic events or neurodegenerative disorders), which include any of those described herein.

As used herein, "inhibition of MUC1" or "inhibiting MUC1" is (a) inhibition of the expression of MUC1, (b) inhibition of the binding of MUC1 to another polypeptide; or (c) inhibition of MUC1 activity. As used herein, "inhibition of caspase-8" or "inhibiting caspase-8" is (a) inhibition of the protease activity of caspase-8; (b) inhibition of the activation of caspase-8 (i.e., the processing of pro-caspase-8 to an active form of caspase-8); (c) inhibition of the expression of caspase-8; or (d) inhibition of the binding of caspase-8 to one or more protein binding partners (e.g., MUC1 or FADD). As used herein, "inhibition of a DED-containing protein" or "inhibiting a DED-containing protein" is (a) inhibition of the pro- or anti-apoptotic activity of a DED-containing protein; (b) inhibition of the expression of a DED-containing protein; or (c) inhibition of the binding of a DED-containing protein to one or more protein binding partners (e.g., MUC1 or caspase-8). Inhibition of expression includes inhibition of mRNA expression and/or protein expression. Inhibition of expression also includes increased degradation of mRNA or protein.

As used herein, "activation of caspase-8" or "activating caspase-8" is: (i) increasing the expression of caspase-8 (mRNA or protein expression): (ii) increasing the processing of caspase-8 to an active form of caspase-8; or (iii) increasing the protease activity of an active form of a caspase-8. Active forms (or processed forms) of caspase-8 are described in, e.g., Blanchard et al. (Structure (1999) 7(9):1125-33); Cohen (Biochem J (1997) 326(Pt.1):1-16); and Chen et al. (Apoptosis (2002) 7(4):313-9). Methods of activating caspase-8 are known in the art, described herein, and exemplified in the working Examples. For example, caspase-8 can be activated by contacting a cell with a death receptor ligand such as FasL, TRAIL, or TNFα (see, e.g., the working examples). Caspase-8 can be activated by contacting the caspase with another active caspase such as active caspase-3. In yet another example, caspase-8 can be activated by increasing the expression or activity of an agent that activates caspase-8, e.g., FADD or a death receptor.

Where the methods are in vitro cell-based methods or in vivo methods, the methods of modulating an interaction between MUC1 and caspase-8 and/or MUC1 and a DED-containing protein can optionally include a step of identifying a cell as one expressing one or more of MUC1, caspase-8, and/or a DED-containing protein. In in vivo methods, the cell can be, e.g., one from the subject's cancer, inflammatory condition, or neurodegenerative condition, if present. Such identification can include, for example, identifying whether a cell expresses the appropriate mRNA or protein (e.g., an mRNA encoding MUC1, caspase-8, or a DED-containing protein or a MUC1, caspase-8, or a DED-containing protein polypeptide). Suitable methods of identifying the expression of protein or mRNA are well known to those of skill in the art, and are described herein. These methods can include, for example, sodium dodecyl sulfate-polyacrylamide gel electrophoresis (SDS-PAGE)/western blotting techniques using antibodies specific for detection of protein, or RT-PCR or northern blotting techniques for detection of mRNA expression. The cell can be any cell that expresses the relevant proteins, e.g., a cell that expresses an endogenous or a recombinant or exogenous polypeptide or an mRNA encoding a MUC1, caspase-8, or DED-containing protein polypeptide.

Compounds useful in the methods of modulating an interaction between MUC1 and caspase-8 or between MUC1 and a DED-containing protein can include any of the compounds described herein, or any other compounds with the appropriate inhibitory activity. Suitable compounds can include compounds, antibodies, an antibody fragments, polypeptides, or a peptidomimetics (see above). Compounds can also include nucleic acids, for example, nucleic acids that inhibit the mRNA or protein expression of MUC1, caspase-8, or a DED-containing protein (e.g., siRNA). Other exemplary compounds for use in the methods include MUC1, caspase-8, or DED-containing protein polypeptides or their functional fragments. Examples of potential functional fragments of MUC1 include, for example, the MUC1-CD (SEQ ID NO:2) or fragments of the MUC1-CD containing amino acids 1-20 (e.g., SEQ ID NO:4) or amino acids 46-72 (e.g., SEQ ID NO:4). Functional fragments of caspase-8 include, e.g., the p18 subunit of caspase-8 such as the human caspase-8 p18 unit having the amino acid sequence depicted in SEQ ID NO:6 or amino acids 270-322 of caspase-8 (e.g., SEQ ID NO:27 or SEQ ID NO:28). Functional fragments of a DED-containing protein include, e.g., the DED of FADD (e.g., SEQ ID NO:8).

In Vitro Methods.

Provided herein are in vitro methods of modulating (e.g., inhibiting or enhancing) an interaction between a MUC1 reagent and a caspase-8 reagent and for modulating an interaction between a MUC1 reagent and a DED-containing protein reagent. The methods can be useful, for example, in scientific studies to investigate the role of MUC1 in death receptor-mediated apoptosis, or any other scientific studies in which modulating the interaction between MUC1 and caspase-8 and/or between MUC1 and a DED-containing protein can be beneficial (e.g., cancer studies). Where the method is a cell-based method, it can also be useful as a further screening step, in e.g., a drug screening cascade, following the biochemical (e.g., a cell-free method of identifying a compound that inhibits the binding of MUC1 to caspase-8 or MUC1 to a DED-containing protein, as described above) identification of a compound that inhibits the binding of caspase-8 or a DED-containing protein to MUC1. Moreover, it can also serve as a "positive control" in assays to identify compounds with the same activity.

Some of the methods can include the steps of contacting (i) a MUC1 reagent; (ii) an caspase-8 reagent; or (iii) a molecular complex comprising (i) and (ii) with a compound that modulates (e.g., inhibits or enhances) the interaction between MUC1 and caspase-8. Alternatively, the methods can include the steps of contacting (i) a MUC1 reagent; (ii) a DED-containing protein reagent; or (iii) a molecular complex comprising (i) and (ii) with a compound that modulates (e.g., inhibits or enhances) the interaction between MUC1 and a DED-containing protein.

Cell-based methods for inhibiting an interaction can include, e.g., identifying a cell as one expressing one or both of MUC1 and caspase-8; and culturing the cell with an effective amount of a compound that inhibits: (i) MUC1 and/or caspase-8 or (ii) an interaction between MUC1 and caspase-8.

Cell-based methods for inhibiting an interaction can include, e.g., identifying a cell as one expressing one or both of MUC1 and a DED-containing protein; and culturing the cell with an effective amount of a compound that inhibits: (i) MUC1 and/or the DED-containing protein or (ii) an interaction between MUC1 and a DED-containing protein.

Methods for identifying or detecting a cell as expressing mRNA or protein expression are well known to those in the art, are described herein, and are exemplified in the working examples. Suitable concentrations of the inhibitory compound can be elucidated through routine experimentation and such optimization is well known to one of skill in the art. The cell may be co-cultured with one or more additional therapeutic agents (e.g., one or more chemotherapeutic agents or anti-inflammatory agents such as NSAIDS).

It should be understood that where the cell is identified as one expressing a MUC1, the expressed MUC1 can be the MUC1 reagent of the method. For example, a cell identified as one expressing a full-length, wild-type, mature MUC1 protein would thus have at least one MUC1 reagent that is full-length, wild-type, mature MUC1 protein. Likewise, where the cell is identified as one expressing a caspase-8 or a DED-containing protein, the expressed caspase-8 or DED-containing protein can be the caspase-8 reagent or the DED-containing protein reagent (respectively) of the method.

Methods of determining or detecting a modulation of an interaction between a MUC1 reagent and a caspase-8 (or between MUC1 and a DED-containing protein reagent) are known in the art, and include, for example, in vitro and in situ methods. One method of determining whether modulation of the interaction between MUC1 and caspase-8 (or between MUC1 and a DED-containing protein) is an immunoprecipitation method and is exemplified in the working Examples below. Briefly, cells cultured in the presence of a compound can be washed and harvested from the culture vessel. The cells can then be lysed using non-denaturing buffers that preserve protein-protein interactions, for example, buffers containing Nonidet-40 (NP-40) or Triton X-100 detergents. The lysates can then be clarified using, for example, centrifugation to remove insoluble debris. Clarified lysates can then be subjected to immunoprecipitation by adding to the lysate an antibody specific for either MUC1 (or caspase-8 or a DED-containing protein, depending on the interaction being interrogated) for a time sufficient to allow for the binding of the antibody to its cognate antigen. Antibody-protein complexes are isolated from the lysate solution by coupling the complexes to solid support matrices. Examples of such solid support matrices include insoluble beads conjugated to anti-IgG antibodies or other antibody-binding reagents, for example, bacterial Protein-A or Protein-G. Isolated immuno-complexes can then be solubilized in Laemmli buffer (optionally containing reducing agent) and subjected to SDS-polyacrylamide gel electrophoresis (SDS-PAGE). Immunoblotting of the samples using antibodies specific for one or both of MUC1 and caspase-8 (or a DED-containing protein) can then be used to determine whether a compound has modulated (e.g., inhibited or enhanced) the interaction between MUC1 and caspase-8 (or between MUC1 and a DED-containing protein). For example, a reduced amount of caspase-8 protein in anti-MUC1 antibody immunoprecipitates from cells treated with a compound as compared to the amount of caspase-8 in MUC1 immunoprecipitates from cells not treated with the compound indicates that the compound has inhibited the interaction of the two proteins. Similarly, a reduced amount of MUC1 protein in anti-caspase-8 antibody immunoprecipitates from cells treated with a compound as compared to the amount of MUC1 in caspase-8 immunoprecipitates from cells not treated with the compound indicates that the compound has inhibited the interaction of the two proteins. (It is understood that the same principle applies for monitoring interactions between MUC1 and a DED-containing protein).

Another method of determining modulation (e.g., inhibition or enhancement) of an interaction between MUC1 and caspase-8 (or a DED-containing protein) is an in situ staining method. Immunostaining methods are well known to those of skill in the art and include embodiments where the cells are still viable (e.g., confocal microscopy of live cells) or are fixed cells (e.g., immunohistochemistry). In the case of an interaction between MUC1 and caspase-8, e.g., antibodies specific for MUC1 and caspase-8 polypeptides are applied (e.g., administered, delivered, contacted) to cells. The antibodies are independently labeled with a different detectable label (e.g., a different colored fluorophore (e.g., rhodamine, texas red, FITC, Green fluorescent protein, Cy3, Cy5) such that they can be readily and easily distinguished from one another. Use of an appropriate microscope (e.g., a confocal microscope) with the appropriate optical filters can identify the position of the labeled antibodies in a given cell. When each of the positions of the two proteins are determined (i.e., the location of their respective detectable label within the cell as determined by antibody binding), if they are found to occupy the same space, the two proteins are said to co-localize. Thus, when two proteins co-localize in the absence of a compound but do not co-localize in the presence of a compound, this can indicate that the compound has inhibited the interaction between the two proteins. In contrast, when two proteins do not co-localize, or co-localize to a small degree, in the absence of a compound but are found to co-localize (or co-localize to a greater degree) in the presence of a compound, this can indicate that the compound has enhanced the interaction between the two proteins. Optionally the cells can be fixed, for example, using paraformaldehyde or formaldehyde, and permeabilized using a detergent (e.g., Triton-X100).

It is understood that co-localization of two proteins (e.g., MUC1 and caspase-8 or MUC1 and a DED-containing protein) can be due to a direct, physical interaction of two proteins or it can be due to the localization of two proteins to a given, defined site in a cell (e.g., the cell membrane), not necessarily involving a physical association between the two proteins. For example, MUC1 and caspase-8 can co-localize at the cell membrane of a cell, but in the absence of an interaction (e.g., in the presence of an inhibitor of their interaction) between them they can relocalize to distinct regions (e.g., the cytoplasm). In this regard, to define the particular localizations or organelles where localization occurs, it can be useful to use antibodies or other dyes that specifically detect the particular organelles or cellular regions of interest.

As MUC1 has been shown to inhibit death receptor-mediated apoptosis in cells, inhibition or enhancement of MUC1-caspase-8 or MUC1-DED-containing protein interaction could be detected as a change in the amount of apoptosis of a cell. A variety of suitable methods for detecting apoptosis are known in the art and exemplified in the working examples. For example, cells can plated on solid support matrix (e.g., a plastic tissue culture plate, or a multiwell (96 or 386-well) tissue culture plate) and grown in appropriate medium. Cells are then co-cultured in the absence or presence of an appropriate inhibitory compound and after a predetermined amount of time (e.g., 6 hours, 12 hours, 16 hours, 18 hours, 24 hours, 36 hours, 48 hours, or 72 hours) evaluated for the extent of apoptosis. In some embodiments, the cell can be exposed to sub-lethal levels of an apoptosis inducer (e.g., heat shock, a chemotherapeutic agent, or a death ligand such as FasL, TRAIL, or TNFα) to sensitize cells to apoptosis. Often, a control compound (e.g., a known inhibitor of known concentration) is also added to a sample of cells as an internal standard. In addition, a sample of cells is grown in the presence of a carrier, buffer, or solvent, in which the compound is delivered. Methods of detecting (e.g., determining or measuring) apoptosis (e.g., an increase or decrease in apoptosis) are myriad and well known to those of ordinary skill in the art. These methods can include, for example, counting the number of viable cells remaining in the well after the period of treatment with the compound. In this method, cells can be trypsinized from the plate, washed, stained with a dye (e.g., typan blue), and counted using a microscope or mechanical cell counter (Beckman-Coulter Z1™ Series COULTER COUNTER® Cell and Particle Counter). Since dyes such as trypan blue are only taken up by dead or dying cells, this method allows for discrimination (i.e., blue or white cell) between non-viable and viable cells in a population. Another method for determining cell growth inhibition in the presence of an inhibitory compound (e.g., any one of the compositions described herein) following treatment is a metabolic assay, for example, an MTT-metabolic assay (Invitrogen, USA). MTT Diphenyltetrazolium Bromide, is a tetrazolium salt (yellowish) that is cleaved to formazan crystals by the succinate dehydrogenase system which belongs to the mitochondrial respiratory chain, and is only active in viable cells. The mitochondrial succinate dehydrogenase reduces the MTT crystals into purple formazan in the presence of an electron coupling reagent. Following the treatment of the cells with a compound, the cells are exposed to the MTT reagent and the more viable cells are present in a well, the more formazan dye is produced. Extent of formazan dye can be measured, for example, using a spectrophotometer. Other commonly used methods of detecting cell growth inhibition include the monitoring of DNA synthesis. Cells grown, for example, in the presence or absence of compound are also treated with a nucleotide analog that can incorporate into the DNA of the cell upon cell division. Examples of such nucleotide analogs include, for example, BrdU or $^3$H-thymidine. In each case, the amount of label incorporated into the cells (grown in the presence and absence of a given inhibitory agent) is quantified, and the amount of label incorporation is directly proportional to the amount of cell growth in the population of cells. In this context, cell proliferation (e.g., cancer cell proliferation) can be decreased by at least 10% (e.g., at least 15%, at least 20%, at least 25%, at least 30%, at least 35%, at least 40%, at least 50%, at least 55%, at least 60%, at least 65%, at least 70%, or at least 75% or more) relative to the cell proliferation in the absence of the inhibitor. It is understood that the methods described above can be used for detecting or measuring both cell proliferation and viability.

In some instances, the cells can be co-cultured in the presence of sub-toxic amounts of a apoptosis-inducing compound (e.g., a chemotherapeutic agent, genotoxic agent, or an apoptosis-inducing ligand such as FasL or TNFα) to sensitize cells to cell death. For example, cells could be cultured with a chemotherapeutic agent (e.g., carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide, podophyllotoxin, taxol, satraplatinum, 5-flurouracil, vincristin, vinblastin, methotrexate, ara-C, taxotere, gencitabine, cisplatinum, adriamycin, or an analog of any of the aforementioned) and a compound that, e.g., modulates an interaction between MUC1 and either caspase-8 or a DED-containing protein or inhibits MUC1, caspase-8, or a DED-containing protein.

Comparisons of apoptosis between cells cultured with and without compound can be accomplished by measuring a host of indicators, for example, DNA fragmentation, caspase activity, loss of mitochondrial membrane potential, increased production of reactive oxygen species (ROS), intracellular acidification, chromatin condensation, phosphatidyl serine levels at the cell surface, or an increased cell permeability.

DNA fragmentation can be measured, e.g., by with the TUNEL assay (terminal deoxynucleotide transferase dUTP nick end labeling). Commercial versions of the assay are widely available, for example, APO-BrdU™ TUNEL Assay Kit (Invitrogen), APO-DIRECT™ Kit (BD-Biosciences-Pharmingen) and ApoAlert™ DNA fragmentation Assay Kit (Clontech).

Caspase activity can be measured via fluorogenic, chromogenic, and luminescent substrates specific for a given caspase (e.g., Caspase 3 or Caspase 9). Commercial kits are available for a variety of caspases such as caspase 3, caspase 7, caspase 8, and caspase 9 (see BD-Pharmingen or Invitrogen).

Loss of mitochondrial membrane potential can be measured with fluorescent dyes that selectively accumulate in various compartments of the mitochondria based on their integrity and functionality. One non-limiting example of such a dye is Mitotracker Red (Invitrogen).

Production of reactive oxygen species can be monitored with fluorescent dyes such as H2DCFDA.

Chromatin condensation can be measured with dyes such as Hoechst 33342 or propidium iodide.

Phosphotidyl serine (PS) levels can be measured at the cell surface. For example, Annexin V having a high affinity for PS, can be used to as a probe for PS on a cell surface. Numerous commercially available assay kits are suitable for such measurements (see BD-Biosciences Pharmingen).

As described above, any of the in vitro methods for detecting modulation of an interaction between MUC1 and caspase-8 or between MUC1 and a DED-containing protein can be performed in any format that allows for rapid preparation, processing, and analysis of multiple reactions.

In Vivo Methods.

The disclosure also features an in vivo method of modulating (e.g., inhibiting or enhancing) an interaction between MUC1 and caspase-8 or between MUC1 and a DED-containing protein. The methods generally include the step of delivering to a subject an effective amount of a compound that modulates an interaction between MUC1 and caspase-8 or between MUC1 and a DED-containing protein.

The subject can be any mammal, e.g., a human (e.g., a human patient) or a non-human primate (e.g., chimpanzee, baboon, or monkey), mouse, rat, rabbit, guinea pig, gerbil, hamster, horse, a type of livestock (e.g., cow, pig, sheep, or goat), a dog, cat, or a whale. The subject can be one having, suspected of having, or at risk for developing a pathological condition characterized by an elevated or a decreased level of apoptosis. Pathological conditions characterized by an elevated level of apoptosis include, e.g., neurodegenerative disorders and ischemic events. The neurodegenerative disorder can be, e.g., Alzheimer's disease, Parkinson's disease, Huntingdon's disease, multiple sclerosis, amyotrophic lateral sclerosis (ALS), spinobulbar atrophy, denervation atrophy, spinal muscular dystrophy (SMA), pigmentary degeneration of the retina and glaucoma, cerebellar degeneration and neonatal jaundice, otosclerosis, stroke, dementia, successive delayed neuronal death (DND), or any other neurodegenerative disorder known in the art. The ischemic disorder can be, e.g., a stroke, ischemic acute renal failure, intestinal ischemia, myocardial infarction, myocardial ischemia and disorder after reperfusion, liver ischemia, brain ischemia, ischemia retinae, or any other ischemic disorder known in the art, the pathological condition characterized by a decreased level of apoptosis is a cancer, an inflammatory disorder, a developmental disorder (e.g., a morphogenic disorder), or a microbial infection. The microbial infection can be, e.g., any infection by a microorganism (e.g., a virus, a bacterium, a fungus (e.g., a yeast), or a protozoan) encoding a protein that inhibits apoptosis in a cell. For example, proteins encoded by viruses such as, but not limited to, adenoviruses, Epstein Barr virus, pox viruses, retroviruses (e.g., HIV), and herpes viruses. A morphogenic disorder can be, e.g., syndactyly. Examples of cancers and inflammatory conditions are known in the art and are described herein.

As noted throughout, DED-containing proteins can be pro-apoptotic or anti-apoptotic. As such, it is understood that modulation of an interaction between MUC1 and a pro-apoptotic DED-containing protein will have different cellular and physiological effects than modulation of an interaction between MUC1 and an anti-apoptotic DED-containing protein. For example, a compound that inhibits an interaction between MUC1 and a pro-apoptotic DED-containing protein can be administered to a subject having, suspected of having, or at risk for developing a pathological condition characterized by a decreased level of apoptosis (e.g., a cancer or an inflammatory condition). On the other hand, a compound that enhances an interaction between MUC1 and a pro-apoptotic DED-containing protein can be administered to a subject having, suspected of having, or at risk for developing a pathological condition characterized by an elevated level of apoptosis. Similarly, a compound that inhibits an interaction between MUC1 and an anti-apoptotic DED-containing protein can be administered to a subject having, suspected of having, or at risk for developing a pathological condition characterized by a elevated level of apoptosis and a compound that enhances an interaction between MUC1 and an anti-apoptotic DED-containing protein can be administered to a subject having, suspected of having, or at risk for developing a pathological condition characterized by a decreased level of apoptosis.

In some embodiments, the methods can be used for enhancing or reducing cell viability. For example, the methods can include delivering to a cell population an effective amount of a compound that enhances an interaction between MUC1 and a pro-apoptotic DED-containing protein to thereby enhance the viability of the cell population, wherein a plurality of cells of the cell population expresses one or both of MUC1 and the pro-apoptotic DED-containing protein. The methods can also include, e.g., (i) delivering to a cell population an effective amount of a compound that inhibits an interaction between MUC1 and an anti-apoptotic DED-containing protein to thereby enhance the viability of the cell population, wherein a plurality of cells of the cell population expresses one or both of MUC1 and the anti-apoptotic DED-containing protein and/or (ii) delivering to a cell population an effective amount of a compound that enhances an interaction between MUC1 and caspase-8 to thereby enhance the viability of the cell population, wherein a plurality of cells of the cell population expresses one or both of MUC1 and caspase-8.

A "plurality of cells," as used herein, is more than one (1) cell. A "plurality of cells" of a specified type can be, e.g., greater than (or at least) 5 (e.g., 6, 7, 8, 9, 10, 15, 20, 25, 30, 35, 40, 45, 50, 55, 60, 65, 70, 75, 80, 85, 90, or 95 or greater) % of the specified cells in a population of cells. The cell population can be in a tissue or organ (e.g., any tissue or any organ). For example, the cell population can be in a neuronal tissue or a muscle tissue. The cell population can be in heart tissue, brain tissue, or spinal cord tissue. The cell population can be in a subject such as any of the subjects described herein.

The term "effective amount," "therapeutically effective amount," or "therapeutically effective dose" is intended to mean that amount of a compound that will elicit the desired biological or medical response. For example, a "therapeutically effective amount" of a compound can be one that ameliorates one or more symptoms of a subject's pathological condition such as any of those described herein. A therapeutically effective amount of a compound (e.g., a compound that modulates an interaction between MUC1 and caspase-8 or between MUC1 and a DED-containing protein) includes milligram, microgram, nanogram, or picogram amounts of the reagent per kilogram of subject or sample weight (e.g., about 1 nanogram per kilogram to about 500 micrograms per kilogram, about 1 microgram per kilogram to about 500 milligrams per kilogram, about 100 micrograms per kilogram to about 5 milligrams per kilogram, or about 1 microgram per kilogram to about 50 micrograms per kilogram).

Any of the methods described herein can optionally include the steps of (a) determining if the one or more cancer cells of the subject express one or more of MUC1, caspase-8, and/or a DED-containing protein and/or (b) determining whether modulation of an interaction between MUC1 and caspasc-8 or between MUC1 and a DED-containing protein has occurred.

Generally, the compounds will be suspended in a pharmaceutically-acceptable carrier (e.g., physiological saline) and administered orally, rectally, or parenterally, e.g., injected intravenously, subcutaneously, intramuscularly, intrathecally, intraperitoneally, intrarectally, intravaginally, intranasally, intragastrically, intratracheally, or intrapulmonarily. The dosage required depends on the choice of the route of administration; the nature of the formulation; the nature of the subject's condition; the subject's size, weight, surface area, age, and sex; other drugs being administered; and the judgment of the attending physician. Suitable dosages are in the range of 0.0001 mg/kg-100 mg/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 4-, 6-, 8-, 10-, 20-, 50-, 100-, 150-, or more fold). Encapsulation of the compound in a suitable delivery vehicle (e.g., polymeric microparticles or implantable devices) may increase the efficiency of delivery, particularly for oral delivery.

Alternatively, where a compound is a polypeptide, a polynucleotide containing a nucleic acid sequence encoding the polypeptide can be delivered to appropriate cells in a subject. Expression of the coding sequence can be directed to any cell in the body of the subject. However, expression will preferably be directed to cells local to, or mediating, the condition. For example, expression can be directed to: (i) tumor cells (or to normal cells surrounding a tumor), (ii) immune cells mediating an inflammatory condition, or (iii) neuronal cells affected by a neurodegenerative disorder. This can be achieved by, for example, the use of polymeric, biodegradable microparticle or microcapsule delivery devices known in the art for direct, targeted delivery to cells.

Another way to achieve uptake of the nucleic acid is using liposomes, prepared by standard methods. The vectors can be incorporated alone into these delivery vehicles or co-incorporated with tissue-specific or tumor-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano et al. (1995), J. Mol. Med. 73:479, the disclosure of which is incorporated herein by reference in its entirety). Alternatively, tissue specific targeting can be achieved by the use of tissue-specific transcriptional regulatory elements (TRE) which are known in the art. Delivery of "naked DNA" (i.e., without a delivery vehicle) to an intramuscular, intradermal, or subcutaneous site is another means to achieve in vivo expression.

In the relevant polynucleotides (e.g., expression vectors), the nucleic acid sequence encoding the polypeptide of interest with an initiator methionine and optionally a targeting sequence is operatively linked to a promoter or enhancer-promoter combination. Short amino acid sequences can act as signals to direct proteins to specific intracellular compartments. Such signal sequences are described in detail in U.S. Pat. No. 5,827,516, the disclosure of which is incorporated herein by reference in its entirety.

Enhancers and promoters are discussed above. Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. Pharmaceutically acceptable carriers are biologically compatible vehicles that are suitable for administration to a human, e.g., physiological saline or liposomes. A therapeutically effective amount is an amount of the polynucleotide that is capable of producing a medically desirable result (e.g., decreased proliferation of cancer cells) in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to approximately $10^{12}$ copies of the polynucleotide molecule. This dose can be repeatedly administered, as needed. Schedules and co-administration can be any of those described herein (see, for example, "Pharmaceutical compositions and Methods of Treatment"). Routes of administration can be any of those listed above.

In some embodiments, the in vivo methods can include the step of determining whether a subject has a pathological condition. Where the subject has (or is determined to have) a cancer or an inflammatory disorder, the methods can include the step of determining if one or more cells of the subject's cancer or one or more immune cells mediating the subject's inflammatory condition express MUC1, caspase-8, or a DED-containing protein. Methods for determining expression are described above.

Any of the compounds can also, in some instances, be co-administered with one or more additional therapies or therapeutic agents such as chemotherapeutic agents. Methods for co-administration and exemplary additional therapies and therapeutic agents that can be co-administered with any of the compounds described herein are detailed below.

A compound or pharmaceutical composition thereof described herein can be administered to a subject as a combination therapy with another treatment, e.g., a treatment for a pathological condition characterized by a decreased level of apoptosis (e.g., a cancer or an inflammatory disorder) or an increased level of apoptosis (e.g., a neurodegenerative disorder or an ischemic event). For example, the combination therapy can include administering to the subject (e.g., a human patient) one or more additional agents that provide a therapeutic benefit to the subject who has, or is at risk of developing, (or suspected of having) a pathological condition. Thus, the compound or pharmaceutical composition and the one or more additional agents can be administered at the same time. Alternatively, the compound can be administered first in time and the one or more additional agents administered second in time. The one or more additional agents can be administered first in time and the compound administered second in time. The compound can replace or augment a previously or currently administered therapy. For example, upon treating a subject with a compound, administration of the one or more additional agents can cease or diminish, e.g., be administered at lower levels. Administration of the previous therapy can also be maintained. In some instances, a previous therapy can be maintained until the level of the compound (e.g., the dosage or schedule) reaches a level sufficient to provide a therapeutic effect. The two therapies can be administered in combination.

It will be appreciated that in instances where a previous therapy is particularly toxic, administration of a compound can be used to offset and/or lessen the amount of the previously therapy to a level sufficient to give the same or improved therapeutic benefit, but without the same level of toxicity.

In some instances, when the subject is administered a compound or pharmaceutical composition thereof the first therapy is halted. The subject can be monitored for a first pre-selected result, e.g., an improvement in one or more symptoms of a pathological condition characterized by elevated or decreased level of apoptosis, such as any of those described herein (e.g., see above). In some cases, where the first pre-selected result is observed, treatment with the compound is decreased or halted. The subject can then be monitored for a second pre-selected result after treatment with the compound is halted, e.g., a worsening of a symptom of any of the pathological conditions described herein. When the second pre-selected result is observed, administration of the compound to the subject can be reinstated or increased, or administration of the first therapy is reinstated, or the subject is administered both a compound and first therapy, or an increased amount of the compound and the first therapeutic regimen.

Suitable additional therapies will, of course, depend on a subject's particular pathological condition. For example, where the subject suffers from a cancer, the one or more additional therapies can include, e.g., one or more chemotherapeutic agents, one or more forms of ionizing radiation, one or more immunotherapy agents, or one or more hyperthermotherapy agents. The one or more forms of ionizing radiation can be, e.g., gamma-irradiation, X-irradiation, or beta-irradiation. The one or more chemotherapeutic agents can be, e.g., cisplatin, carboplatin, procarbazine, mechlorethamine, cyclophosphamide, camptothecin, adriamycin, ifosfamide, melphalan, chlorambucil, bisulfan, nitrosurea, dactinomycin, daunorubicin, doxorubicin, bleomycin, plicomycin, mitomycin, etoposide, verampil, podophyllotoxin, tamoxifen, taxol, transplatinum, 5-flurouracil, vincristin, vinblastin, methotrexate, or an analog of any of the aforementioned.

In some embodiments, e.g., in embodiments where the subject has, is at risk of developing, or is suspected of having, an inflammatory disorders, the one or more therapeutic agents can be a non-steroidal anti-inflammatory drug (NSAID), a disease-modifying anti-rheumatic drug (DMARD), a biological response modifier, or a corticosteroid. The biological response modifier can be an anti-TNF agent. The anti-TNF agent can be, or contain, a soluble TNFα receptor or an antibody specific for TNFα. The antibody specific for TNFα can be, e.g., adulimumab, infliximab, or etanercept.

Ex Vivo Methods.

An ex vivo strategy can involve transfecting or transducing cells obtained from the subject to be treated (or another subject) with a polynucleotide encoding a polypeptide that modulates (e.g., inhibits or enhances) an interaction between MUC1 and caspase-8 or between MUC1 and a DED-containing protein. The transfected or transduced cells are then administered to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, neurons, or muscle cells. In some embodiments, the cells can be stem cells (e.g., where the subject to be treated has a neurodegenerative disorder or suffers from an ischemic event). The transfected or transduced cells can act as a source of the modulatory polypeptide for as long as they survive in the subject. Alternatively, tumor cells or inflammatory cells (e.g., immune cells), preferably obtained from the subject (autologous) but potentially from a subject of the same species other than the subject (allogeneic), can be transfected or transformed by a vector encoding the inhibitory polypeptide. The tumor cells, preferably treated with an agent (e.g., ionizing irradiation) that ablates their proliferative capacity, are then introduced into the subject, where they secrete the polypeptide.

The ex vivo methods can include the steps of harvesting cells from a subject, culturing the cells, transducing them with an expression vector, and maintaining the cells under conditions suitable for expression of the polypeptide that modulates (e.g., inhibits or enhances) an interaction between MUC1 and caspase-8 or between MUC1 and a DED-containing protein. These methods are known in the art of molecular biology. The transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced can be selected, for example, for expression of the coding sequence or of a drug resistance gene. The cells may then be lethally irradiated (if desired) and injected or implanted into the same or another subject.

The following examples are intended to illustrate, not limit, the invention.

EXAMPLES

Example 1

Materials and Methods

Cell Culture.

Human HCT116 colon cancer cells transfected with a vector containing a MUC1 coding sequence (or a vector without the MUC1 coding sequence) (Ren et al. (2004) *Cancer Cell* 5:163-175, the disclosure of which is incorporated herein by reference in its entirety) and human MCF-7 breast cancer cells were cultured in Dulbecco's Modified Eagle Medium (DMEM) (Mediatech, Herndon, Va.) containing 10% heat-inactivated fetal bovine serum (FBS; Mediatech), 100 units/ml penicillin, 100 µg/ml streptomycin, and 2 mM L-glutamine (ATCC, Manasses, Va.). Human BC-1 lymphoma and U-937 leukemia cells were grown in RPMI-640 medium containing 10% FBS, antibiotics and L-glutamine. Human MCF-10A breast epithelial cells were grown in mammary epithelial cell growth media (MEGM; Lonza, Walkersville, Md.). The cultured cells described herein were treated with one or more of the following reagents: TRAIL (Calbiochem, San Diego, Calif.), Flag-tagged TRAIL (Axxora, San Diego, Calif.), TNFα (Sigma, St. Louis, Mo.), and FasL (CH11; Upstate Biotechnology Inc., Lake Placid, N.Y.).

Silencing of MUC1 and FADD Expression.

The BLOCK-iT Target Screening System (Invitrogen, Carlsbad, Calif.) was used to generate two MUC1-specific siRNA molecules (Sequence #1: AAGGTACCATCAATGTCCACG (SEQ ID NO:31); or Sequence #2: AAGTTCAGTGCCCAGCTCTAC (SEQ ID NO:32)) and a control siRNA sequence (CGCTTACCGATTCAGAATGG; SEQ ID NO:33). The RNAi cassettes (nucleic acids encoding the siRNA molecules) were inserted into pLenti4/BLOCK-iT-DEST by LR recombination for the generation of lentiviral vectors. BC-1 cells were infected with the lentiviruses at a multiplicity of infection of 5 in the presence of 8 µg/ml polybrene. Cell clones were selected in methylcellulose semi-solid medium containing 200 µg/ml Zeocin and assayed for downregulation of MUC1 by immunoblotting. Transient transfection of MCF-10A cells with control, MUC1 siRNA, or FADD siRNA pools (Dharmacon, Lafayette, Colo.) was performed using the Lipofectamine 2000 reagent (Invitrogen).

Stable Expression of MUC1-C in U-937 Cells.

PT67 cells, a packaging cell line derived from mouse embryonic fibroblasts (NIH-3T3), were transfected with the retroviral vector pLXIN or the vector containing a nucleic acid encoding the MUC1 cytoplasmic domain (pLXIN-MUC1-C). Cells stably expressing the vectors were selected for using the antibiotic G418. After selection, cell supernatants were filtered, assayed for retroviral titers using NIH3T3 cells, and used for infection of U-937 cells. 24 hours post-infection, the U-937 cells were seeded into methylcellulose medium (Stem Cell Technologies, Vancouver, BC, Canada) and single cell clones were selected for again using G418.

Immunoprecipitation, DISC Isolation, and Immunoblot Analysis.

Cells were lysed by sonication in the presence of 10 mM Tris-HCl, pH 7.5, 150 mM NaCl, 5 mM EDTA, 0.5% NP-40, 100 µg/ml phenylmethylsulphonyl fluoride (PMSF), and standard protease inhibitors. Soluble proteins were incubated with antibodies specific for caspase-8 (Axxora; BD Biosciences, San Jose, Calif.) for 2 hours at 4° C., followed by precipitation with protein A/G beads (Pierce Biotechnologies, Rockford, Ill.). In certain experiments, cells were first incubated with the complex of Flag-tagged TRAIL and anti-Flag (M2; Sigma), and then lysates were immunoprecipitated with protein-G-sepharose to isolate DISC complexes as previously described (Bodmer et al. (2000) *Nat. Cell. Biol.* 2:241-243, the disclosure of which is incorporated herein by reference in its entirety). Immune complexes and lysates were subjected to immunoblot analysis with anti-MUC1-C (Lab-Vision, Fremont, Calif.), anti-caspase-8, anti-β-actin (Sigma, St. Louis, Mo.), anti-His (Invitrogen), anti-GST (EMD Biosciences, LaJolla, Calif.), mouse anti-FADD (Upstate Cell Signaling Solutions, Charlottesville, Va.) and rabbit anti-FADD (Santa Cruz Biotechnology, Santa Cruz, Calif.). Reactivity was detected with horseradish peroxidase-conjugated secondary antibodies and chemiluminescence (GE Healthcare Biosciences, Piscataway, N.J.).

In Vitro Caspase-8 Activity Assay.

Caspase-8 activity was assayed using the Becton Dickinson (BD) ApoAlert™ Caspase-8 Colorimetric Assay Kit and TETD-pNA (p-nitroaniline) as substrate (BD Bioscience). Caspase-8 activity as a function of cleavage of the substrate was determined by measuring the fluorescence emission at 405 nm using a spectrophotometer.

In Vitro Binding Assays.

Purified GST, GST-MUC1-CD(1-72), GST-MUC1-CD deletion mutants, GST-caspase-8, GST-caspase-8 deletion mutants, GST-FADD, GST-N-FADD and GST-C-FADD protein (36) were purified from *E. coli* (BL21 DE3) and immobilized on glutathione-agarose beads (Pierce). His-MUC1-CD(1-72) and His-caspase-8 deletion mutant proteins were purified on Ni-NTA beads (Qiagen, Valencia, Calif.). GST and GST fusion proteins bound to glutathione beads were incubated with purified soluble proteins for 2 hours at 4° C., and washed. Adsorbates bound to the beads were analyzed by solubilizing the protein/bead mixture in Laemli buffer following by sodium dodecyl sulfate polyacrylamide gel electrophoresis (SDS-PAGE) and immunoblotting. For competition studies, GST-caspase-8 DED protein bound to FADD was incubated with increasing amounts of MUC1-CD protein. Precipitated proteins were subjected to SDS-PAGE and immunoblot analysis. In certain studies, binding was performed in the presence of a synthetic peptide (CQCR-RKNYGQLDIFPARDTY) (SEQ ID NO:3) derived from amino acids 1-20 from MUC1-CD (Molecular Biology Core Facility, Dana-Farber Cancer Institute).

Apoptosis Assays.

Cells were fixed in 70% ethanol and incubated in PBS containing 50 µg/ml RNase and 2.5 µg/ml propidium iodide. DNA content was analyzed by flow cytometry. The percentage of cells with sub-G1 DNA was determined by the MOD-FIT LT Program (Verity Software, Topsham, Me.). Cells were also suspended in Annexin-V-FLOUS containing propidium iodide (Roche) and analyzed by flow cytometry.

Example 2

MUC1 Attenuates Death Receptor-Induced Activation of Caspase-8

Figure 1A:
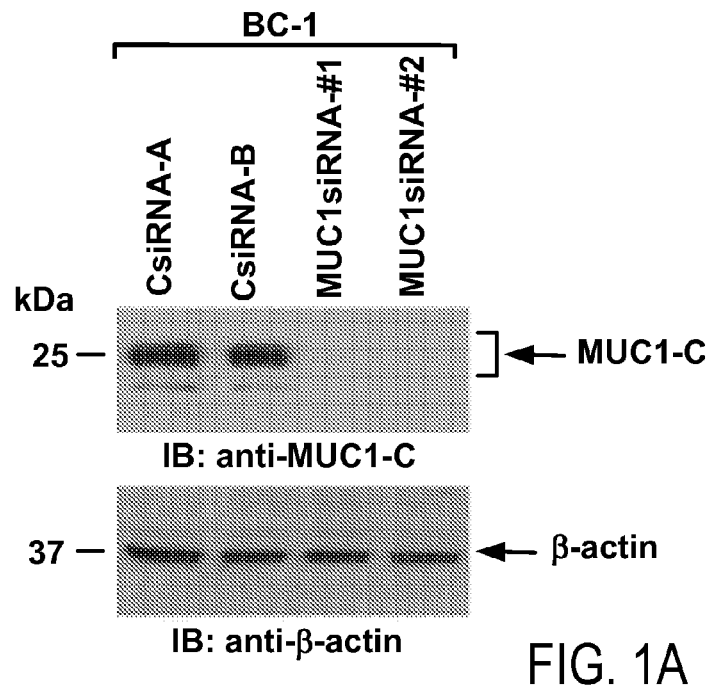
FIGS. 1A-1D are a pair of photographs of a series of western blots (FIGS. 1A and 1B), a series of one-dimensional fluorescence flow cytometry histograms (FIG. 1C), and a bar graph (FIG. 1D).
Figure 1B:
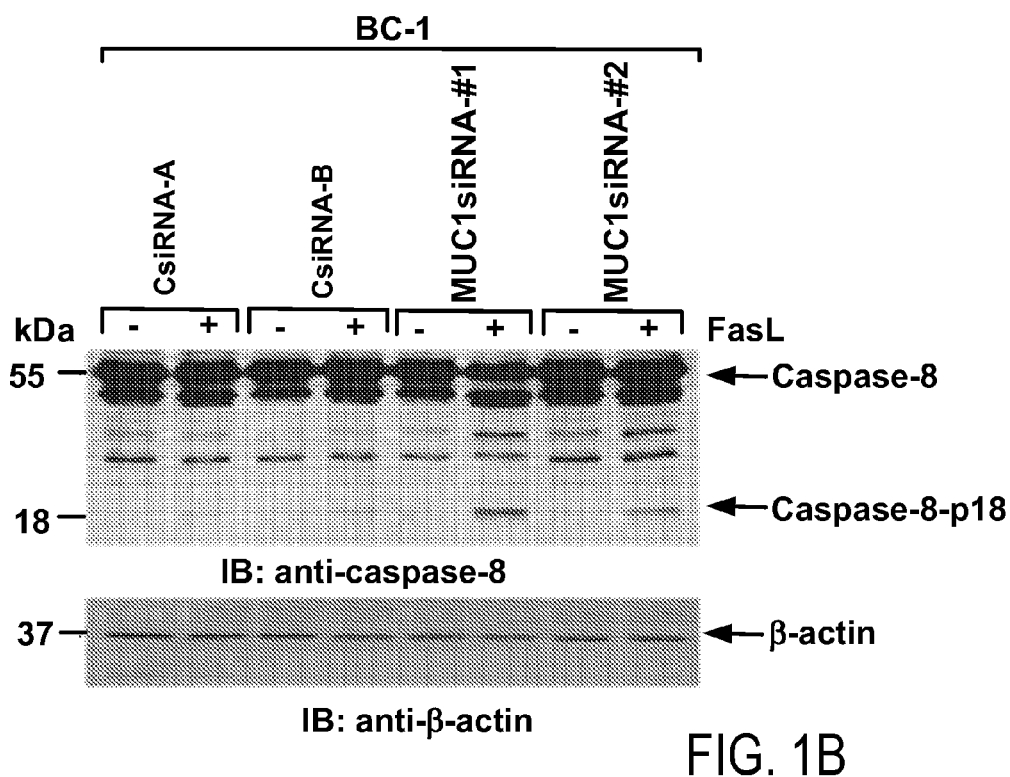

To determine whether MUC1 regulates death receptor signaling, BC-1 cells were infected with a lentivirus expressing an siRNA specific for the MUC1 sequence 5'AAGGTAC-CATCAATGTCCACG-3' (SEQ ID NO:31), which encodes amino acids in MUC1-C (MUC1siRNA#1). These cells are referred to hereinafter as "BC1/MUC1siRNA cells." As compared to BC-1 cells infected with a lentivirus expressing a control siRNA (CsiRNA) (these cells are referred to hereinafter as "BC1/CsiRNA cells"), MUC1-C expression was stably downregulated in cells expressing the MUC1-specific siRNA (MUC1siRNA#1) (FIG. 1A). To rule out potential off-target effects, BC-1 cells were also infected with a lentivirus expressing an siRNA that was specific to a different MUC1 sequence encoding amino acids in MUC1-N, 5' AAGTTCAGTGCCCAGCTCTAC-3' (SEQ ID NO:32); (MUC1siRNA#2). Downregulation of MUC1-C expression was similar with the two MUC1siRNAs (FIG. 1A). Treatment of the BC-1/CsiRNA cells with FasL had little effect on activation of caspase-8 (FIG. 1B). By contrast, FasL treatment of BC-1 cells in which MUC1 expression was silenced was associated with cleavage of caspase-8 to the p18 fragment (FIG. 1B).

Figure 1C:
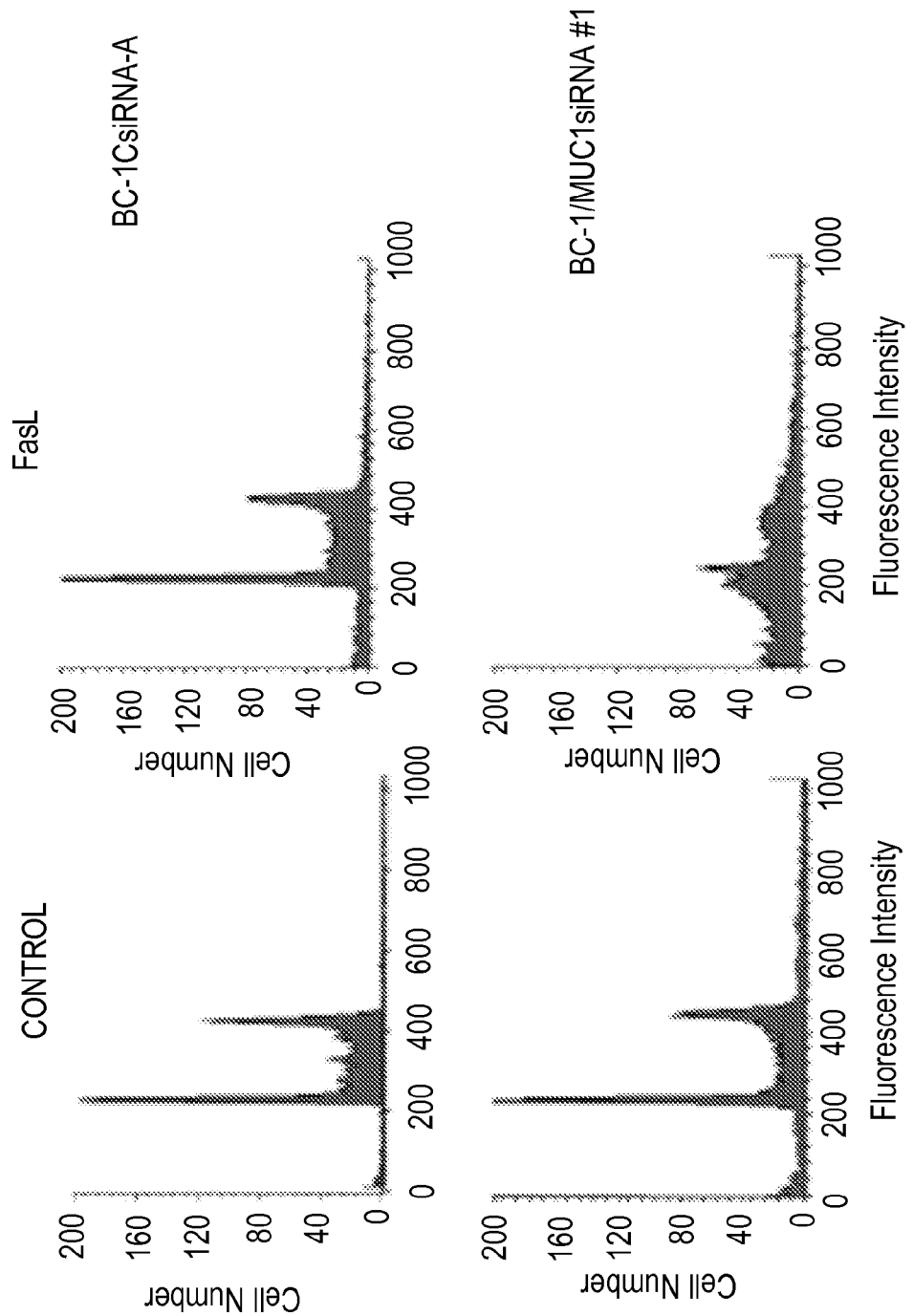
Figure 1D:
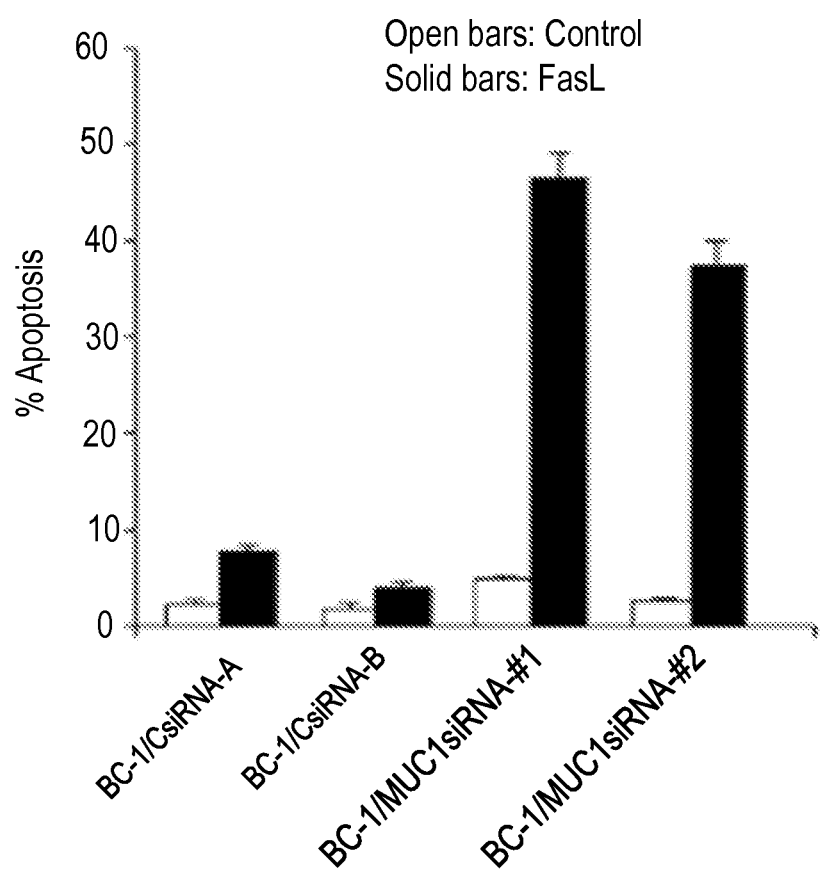
Figure 2:
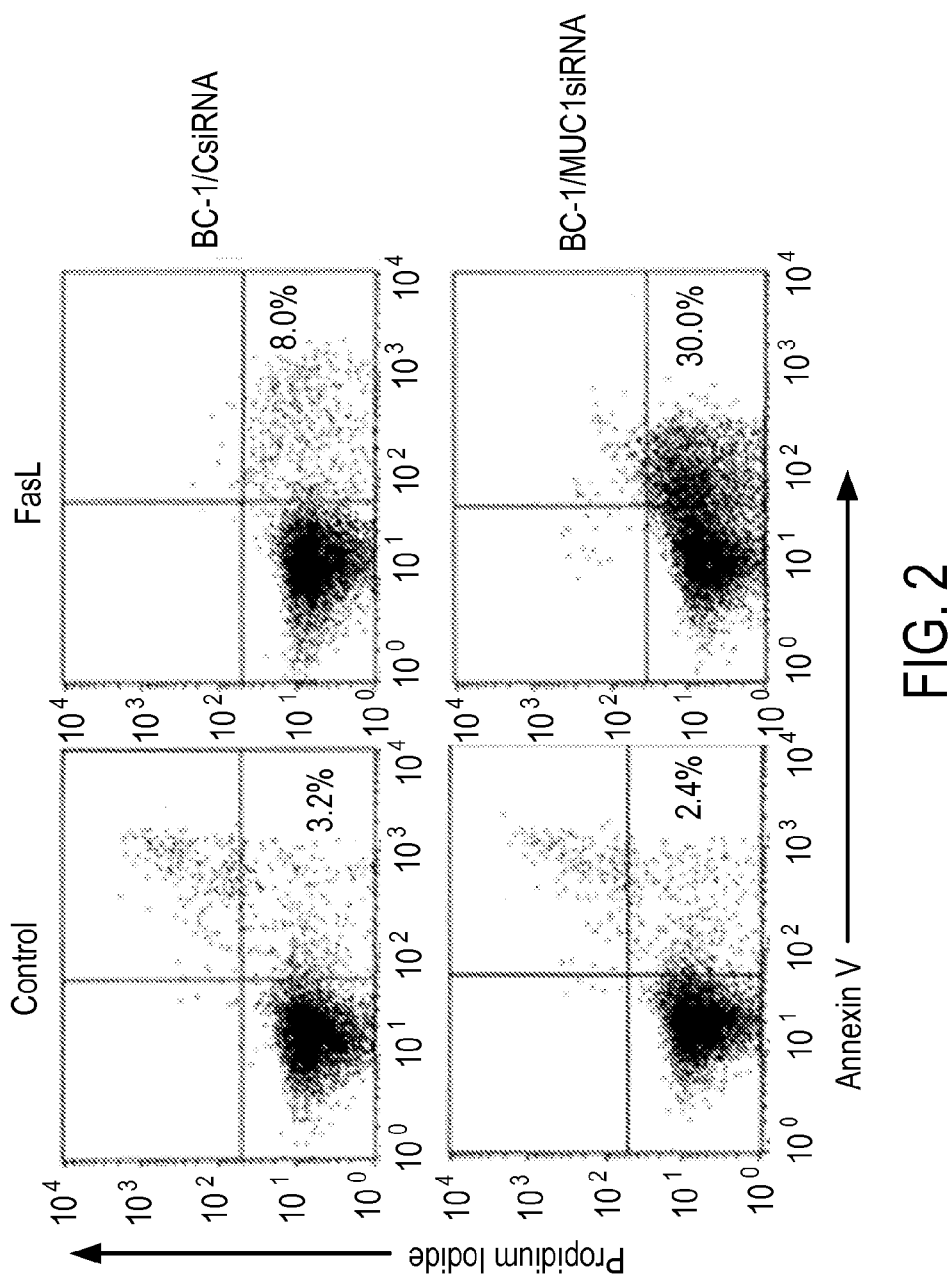
FIG. 2 is a series of two-dimensional fluorescence flow cytometry histograms depicting MUC1 inhibition of FasL-induced apoptosis of BC-1 cells. The indicated BC-1 cell populations were treated with 50 ng/ml FasL for 24 hours, stained with Annexin V and propidium iodide (PI) and then analyzed by flow cytometry. The results are representative of three separate experiments.
Figure 3:
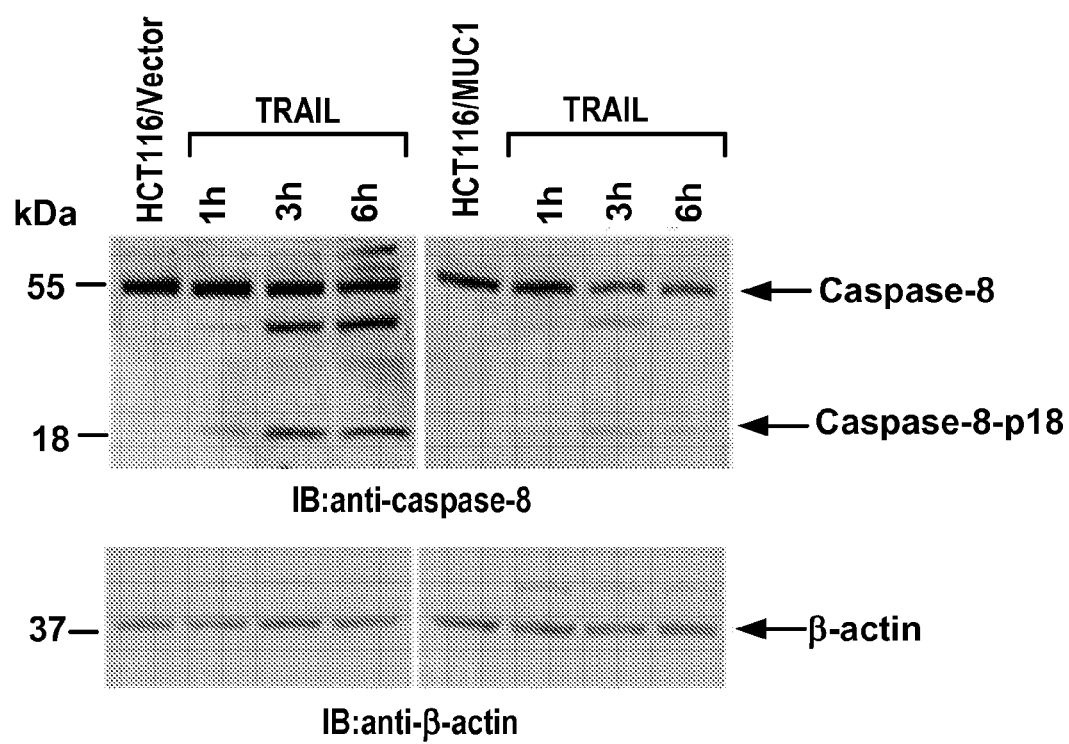
FIG. 3 is a series of photographs of western blots depicting MUC1 inhibition of TRAIL-induced activation of caspase-8 in HCT116 cells. HCT116/vector and HCT116/MUC1 cells were treated with 100 ng/ml TRAIL for the indicated times. Lysates were immunoblotted with anti-caspase-8 and anti-β-actin antibodies as indicated to the right of the photographs. The molecular weights of each of the proteins (in kilodaltons (kDa)) are indicated to the left of each of the photographs.

To determine if silencing MUC1 expression affects death receptor-induced apoptosis, BC-1/CsiRNA and BC-1/MUC1siRNA cells were treated with FasL and then monitored for sub-G1 DNA content. In concert with the inhibitory effects of MUC1 on caspase-8 activation, silencing MUC1 expression sensitized BC-1 cells to FasL-induced apoptosis (FIG. 1C). The inhibitory effect of MUC1 on the apoptotic response to FasL was confirmed in repeated experiments with BC-1 cells expressing MUC1siRNA#1 and MUC1 siRNA#2 (FIG. 1D) and in cells stained with Annexin-V and propidium iodide (FIG. 2). Consistent with the results obtained using BC-1 cells, TRAIL-induced activation of caspase-8 in HCT116 cells was inhibited by a MUC1-dependent mechanism (FIG. 3; MUC1 siRNA potentiates TRAIL-induced apoptosis). These findings indicate that MUC1 attenuates death receptor-induced activation of caspase-8 and apoptosis.

Example 3

MUC1-C is Sufficient to Block Death Receptor-Induced Signaling

Figure 4A:
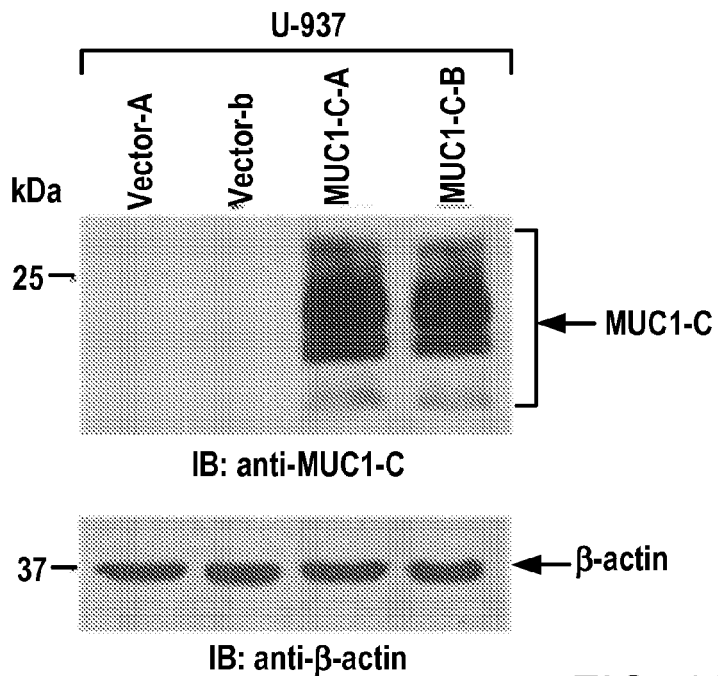
FIGS. 4A-4D are a pair of photographs of a series of western blots (FIGS. 4A and 4B), a series of one-dimensional fluorescence flow cytometry histograms (FIG. 4C), and a bar graph (FIG. 4D).
Figure 4B:
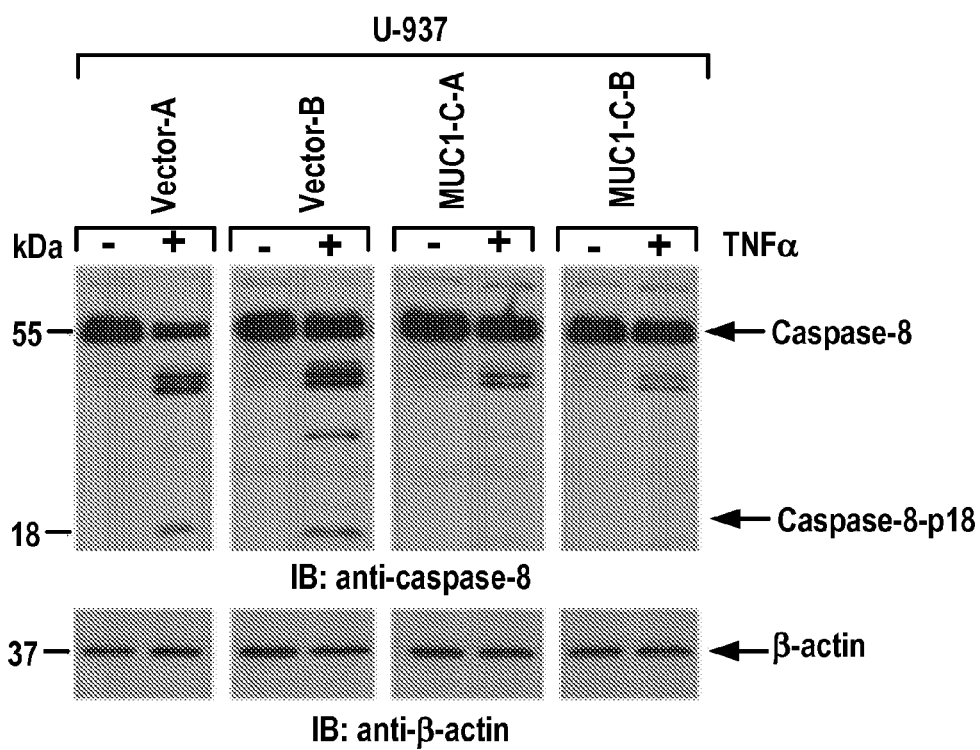
Figure 4C:
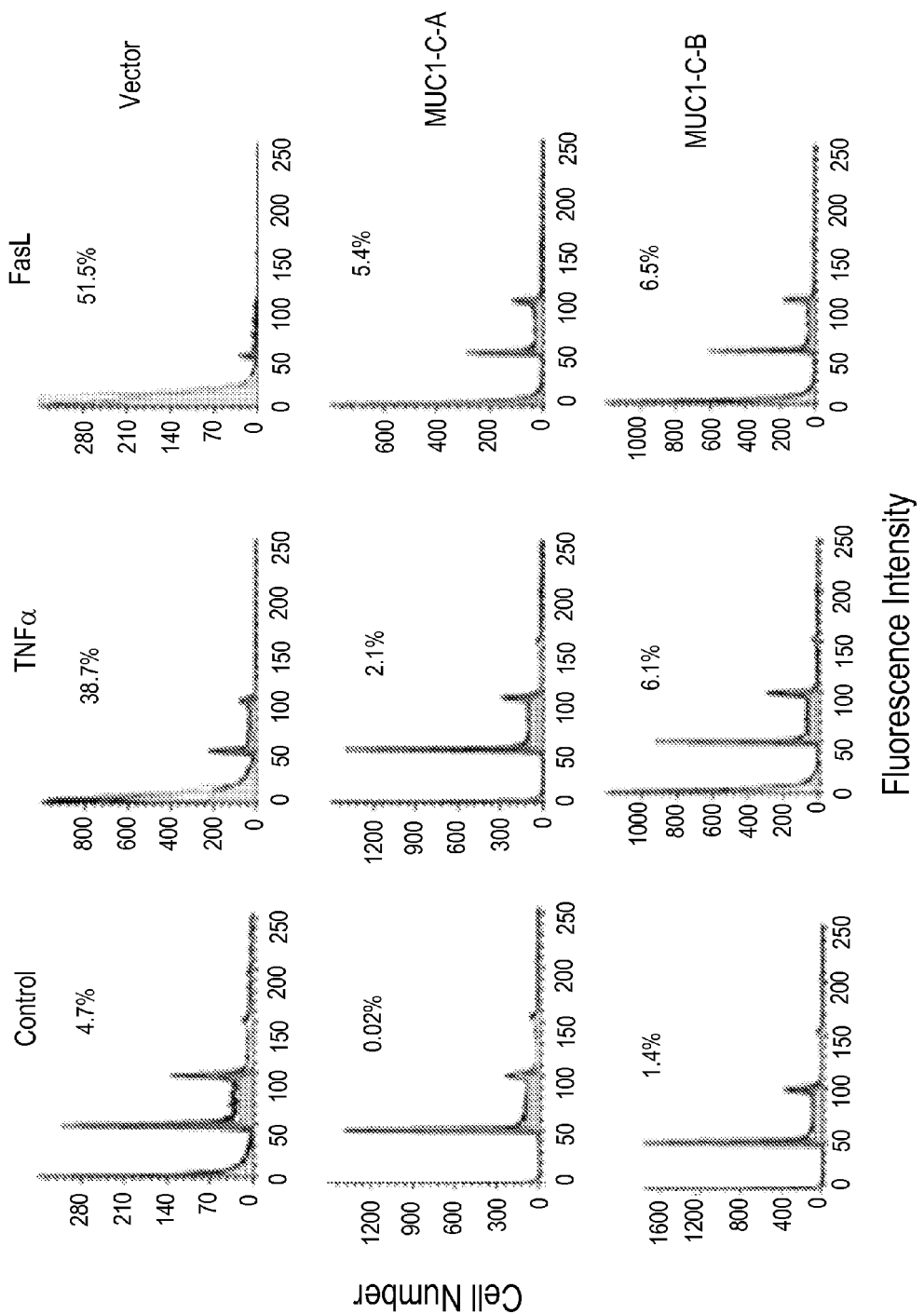
Figure 4D:
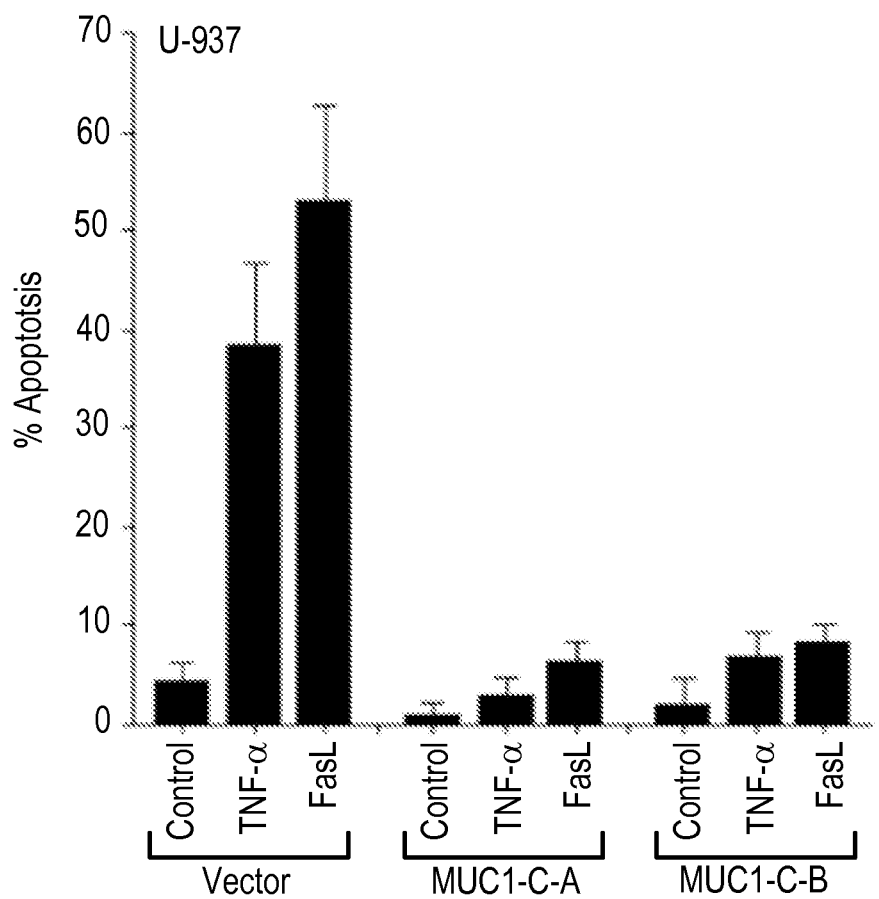
Figure 5:
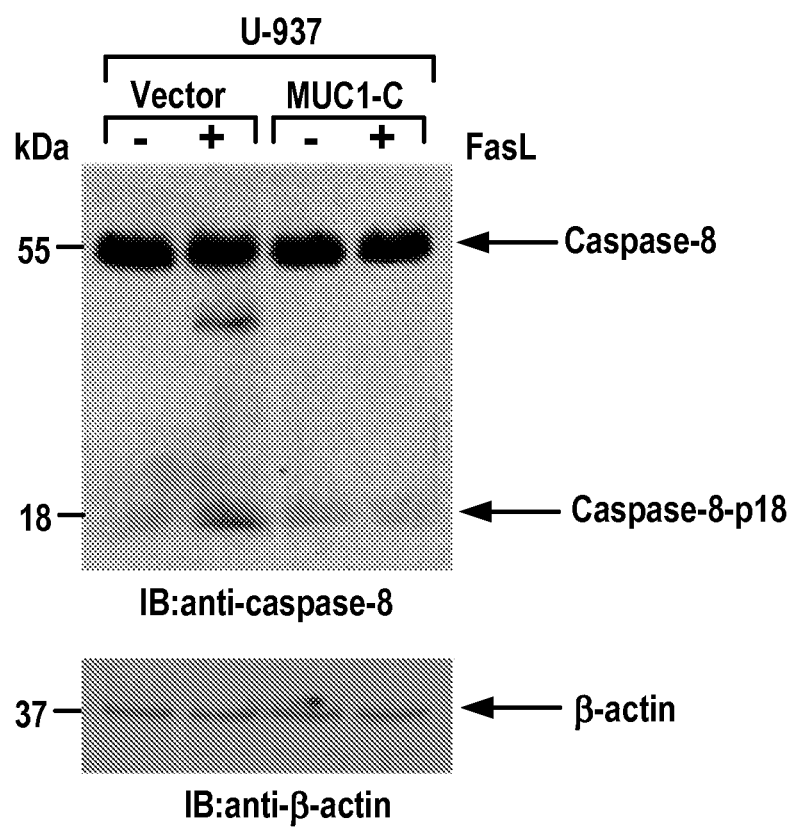
FIG. 5 is a pair of photographs of western blots demonstrating that MUC1-C is sufficient for inhibition of FasL-induced caspase-8 activation. Lysates from the indicated U-937 cell populations treated with 50 ng/ml FasL were immunoblotted with anti-caspase-8 or anti-β-actin antibodies as indicated to the right of the photographs. The molecular weights of each of the proteins (in kilodaltons (kDa)) are indicated to the left of each of the photographs.
Figure 6:
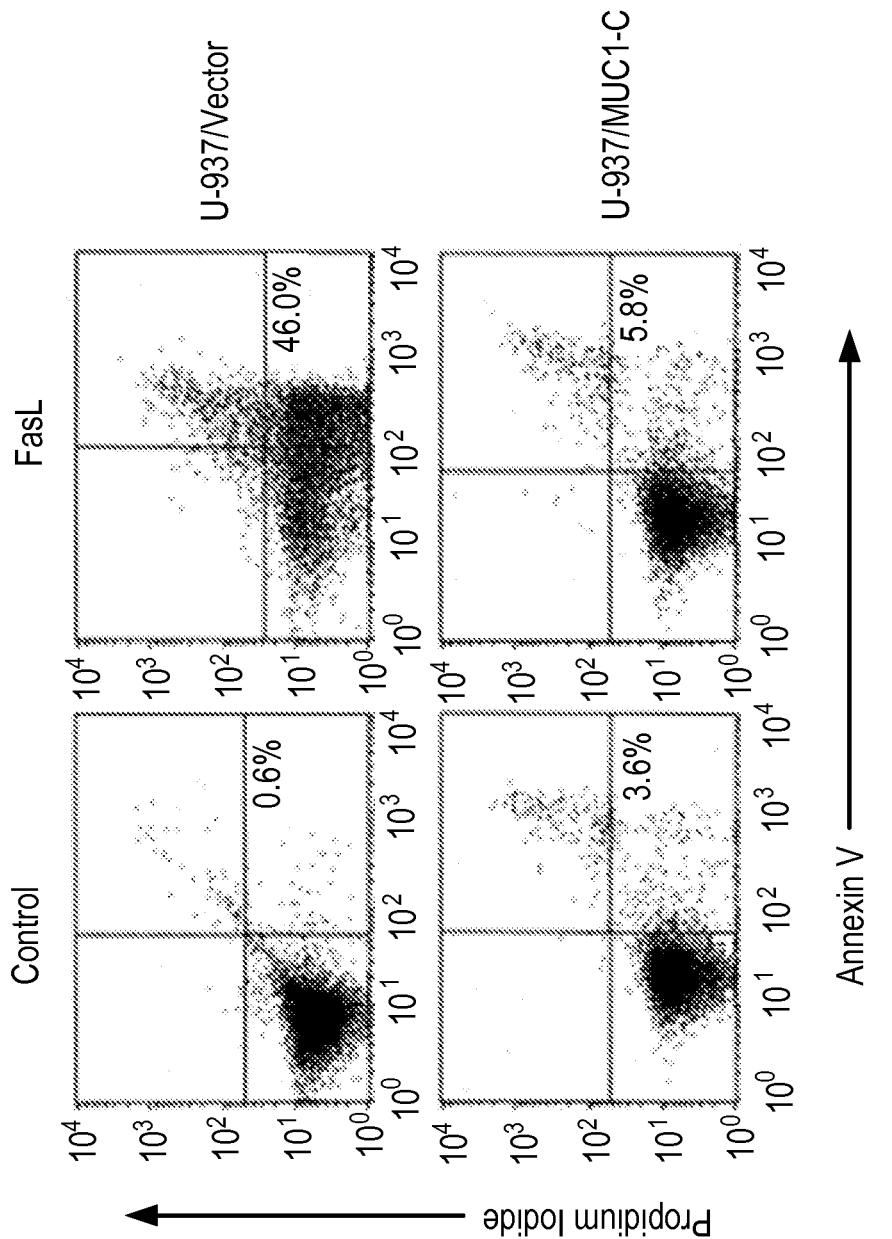
FIG. 6 is a series of two-dimensional fluorescence flow cytometry histograms depicting MUC1-C inhibition of FasL-induced apoptosis of U-937 cells. The indicated U-937 cell populations were treated with 50 ng/ml FasL for 24 hours, stained with Annexin V/PI, and then analyzed by fluorescence flow cytometry. The results are representative of three separate experiments.

To determine if the MUC1-C subunit is sufficient to block activation of caspase-8, MUC1-negative U-937 cells were stably transfected with an empty vector or MUC1-C (FIG. 4A). Treatment of the U-937/vector cells with TNFα was associated with activation of caspase-8 (FIG. 4B). By contrast, this response to TNFα was attenuated in U-937/MUC1-C cells (FIG. 4B). Similar results were obtained when the U-937/vector and U-937/MUC1-C cells were stimulated with FasL (FIG. 5). Moreover, expression of MUC1-C in these cells abrogated sensitivity of the cells to TNFα- and FasL-induced apoptosis (FIG. 4C). These responses were confirmed with both U-937/MUC1-C clones and in repeated experiments (FIG. 4D), and using other apoptotic detection methods such as Annexin-V and propidium iodide (FIG. 6). These findings indicate that MUC1-C is sufficient to block death receptor-induced activation of caspase-8 and apoptosis.

Example 4

Figure 7A:
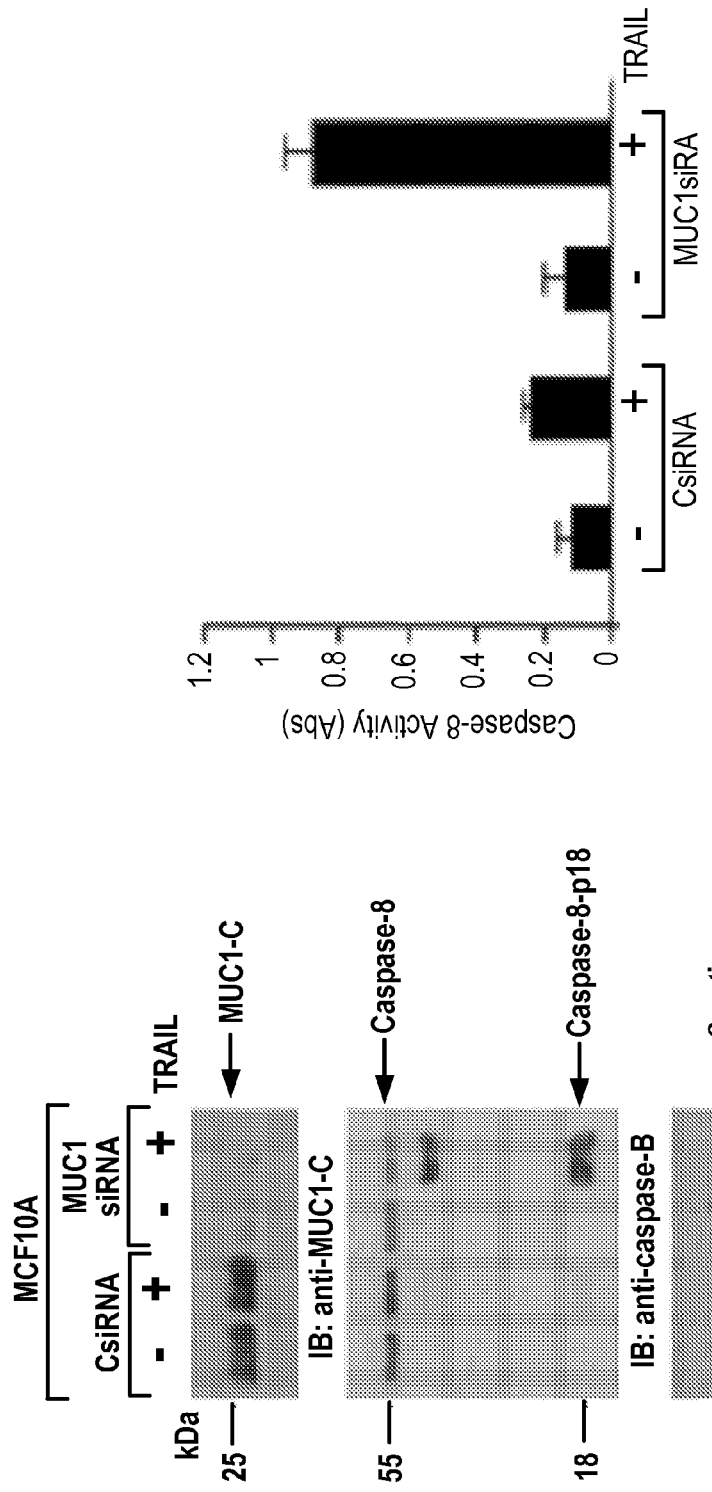

MUC1-C Inhibits Caspase-8 in the Response of Nontransformed MCF-10A Cells to Death Ligand Stimulation Inhibition of caspase-8 by MUC1-C could represent a response in nontransformed cells that is constitutively activated by overexpression of MUC1 in malignant cells. To address this possibility, studies were performed on the nontransformed MCF-10A cells (Soule et al. (1990) *Cancer Res.* 50: 6075-6086; and Muthuswamy et al. (2001) *Nat. Cell. Biol.* 3:785-792, the disclosures of which are incorporated herein by reference in their entirety), which express endogenous MUC1 but at lower levels than that found in carcinoma cells (Ahmed et al. (2007) *Nat. Cell. Biol.* 9:1419-1427, the disclosure of which is incorporated herein by reference in its entirety). Treatment of MCF-10A cells with TRAIL had little if any effect on the activation of caspase-8 (FIG. 7A, left). To assess the effects of MUC1 in the MCF-10A cells, MUC1 expression was silenced in the cells using a pool of MUC1-specific siRNAs, which for transient silencing was determined to be more effective than with the lentiviruses. TRAIL treatment of the MCF-10A cells with MUC1siRNA pool resulted in cleavage of caspase-8 to the p18 fragment (FIG. 7A, left). The apoptotic effects of MUC1 silencing were confirmed by direct measurement of caspase-8 activity (FIG. 7A, right). Silencing of MUC1 expression in MCF-10A cells was also associated with activation of caspase-8 in response to TNFα (FIG. 7B) and FasL (FIG. 7C) stimulation. Notably, the results from coimmunoprecipitation experiments demonstrated that MUC1-C and caspase-8 associate at a low level constitutively, and that this interaction is enhanced by death receptor stimulation (FIG. 7D). In addition, binding of MUC1-C and caspase-8 was detectable constitutively in BC-1, U-937 and HCT116 cells (FIGS. 8A-8C), which indicated that this interaction is found in diverse cell types. These findings indicated that MUC1 associates with caspase-8 and contributes to the physiologic regulation of caspase-8 activation.

Example 5

MUC1-CD Binds Directly to Caspase-8

Figure 7B:
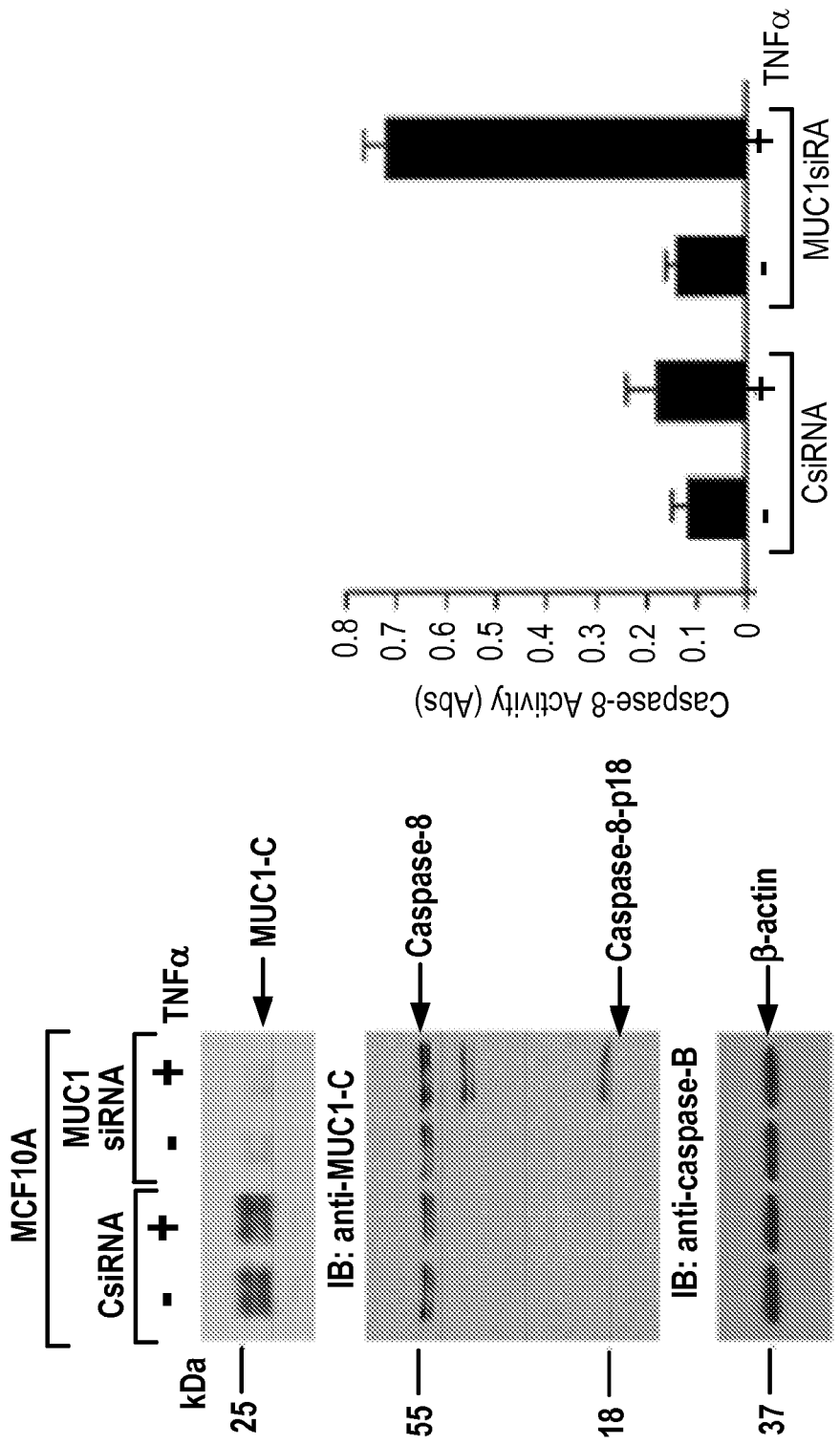
Figures 8A, 8B, 8C:
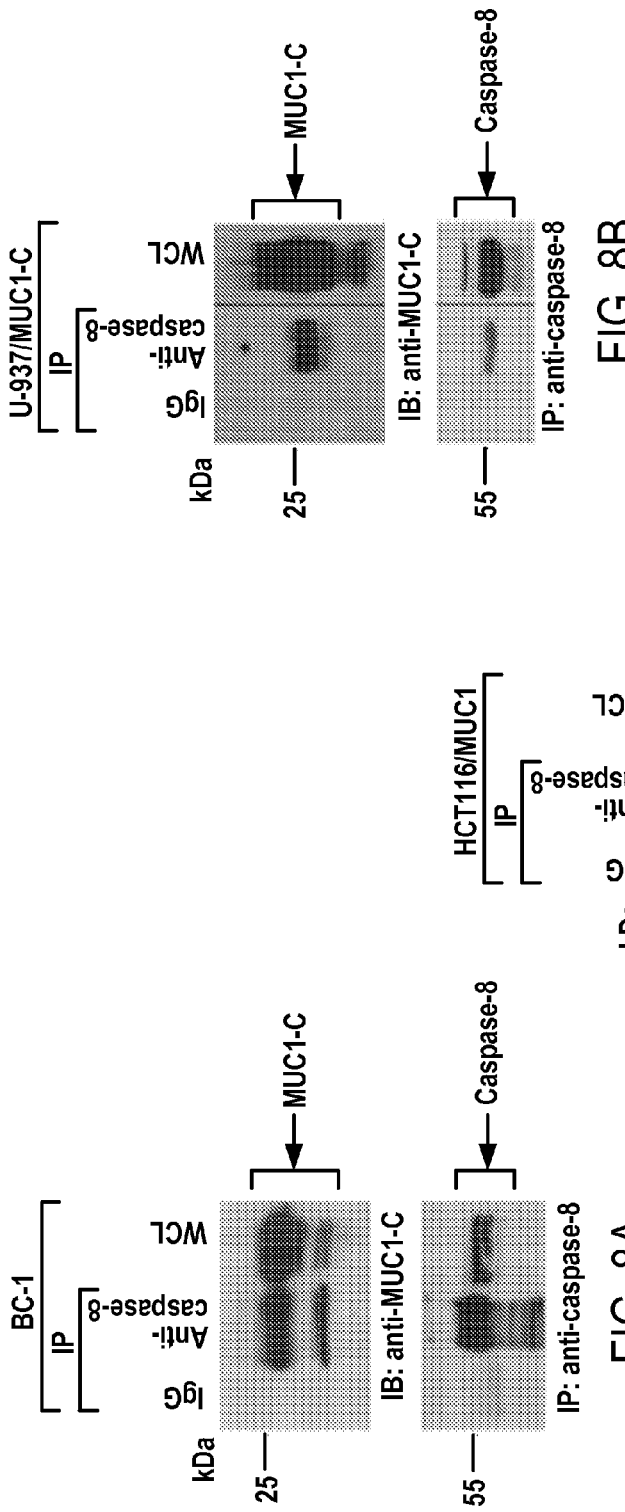
FIGS. 8A-8C are a series of photographs of western blots. Lysates from BC-1 (FIG. 8A), U-937/MUC1-C (FIG. 8B), and HCT116/MUC1 (FIG. 8C) cells were immunoprecipitated with a control IgG reagent or anti-caspase-8 antibody. The precipitates and lysates not subjected to precipitation were immunoblotted with anti-caspase-8, anti-MUC1, or anti-β-actin antibodies as indicated to the right of the photographs. The molecular weights of each of the proteins (in kilodaltons (kDa)) are indicated to the left of each of the photographs.
Figure 9A:
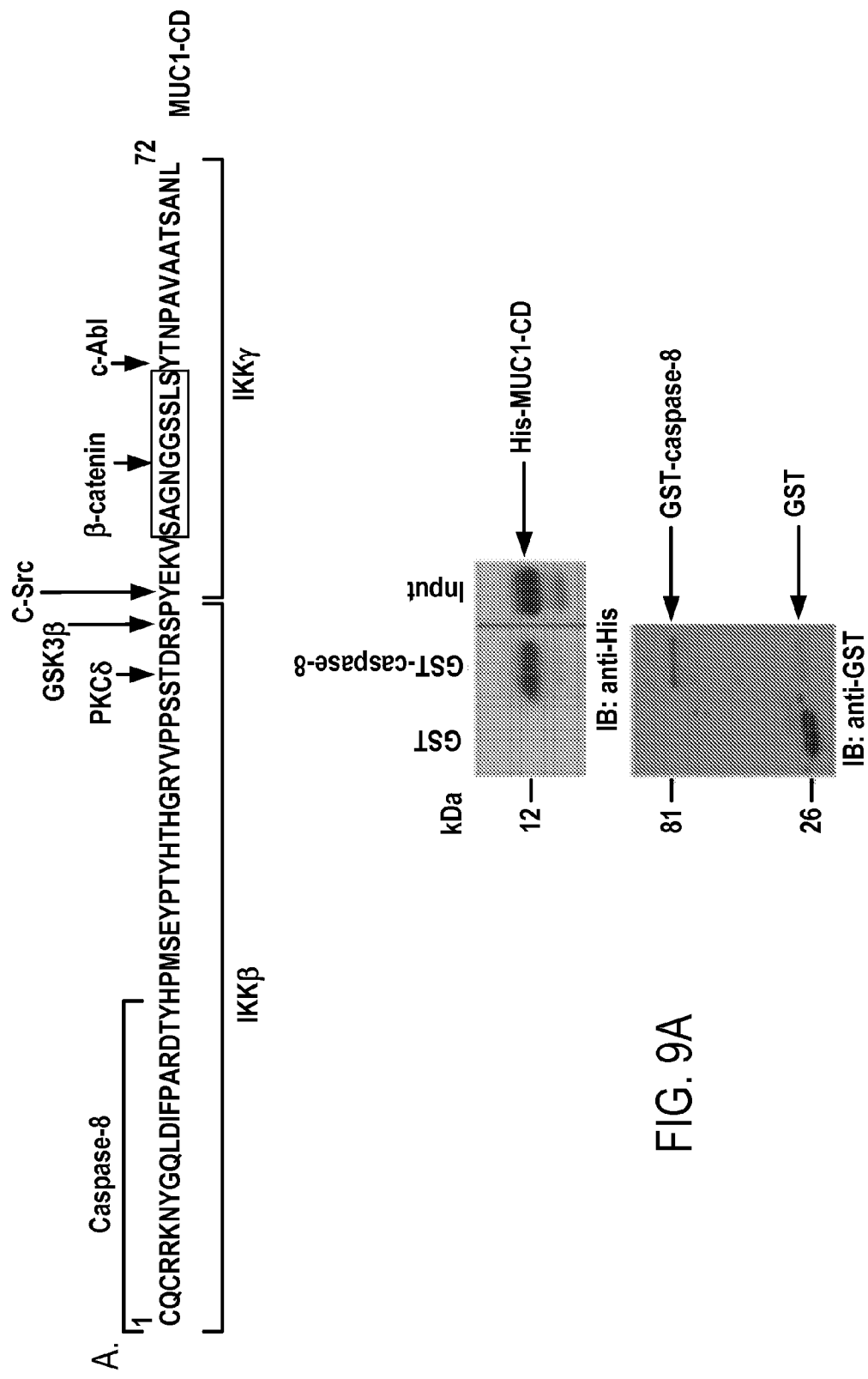
Figure 9D:
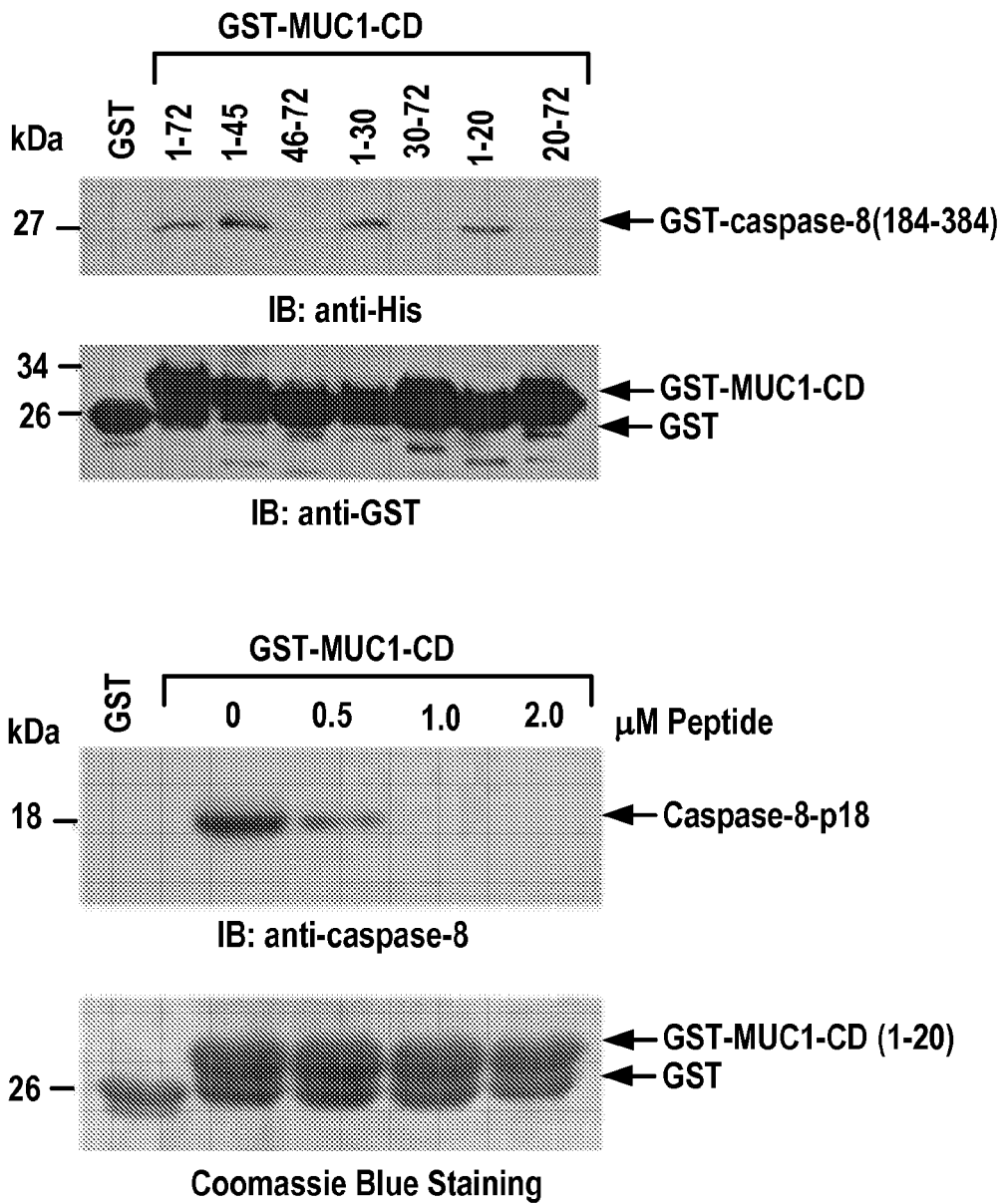
Figures 10, 11A, 11B:
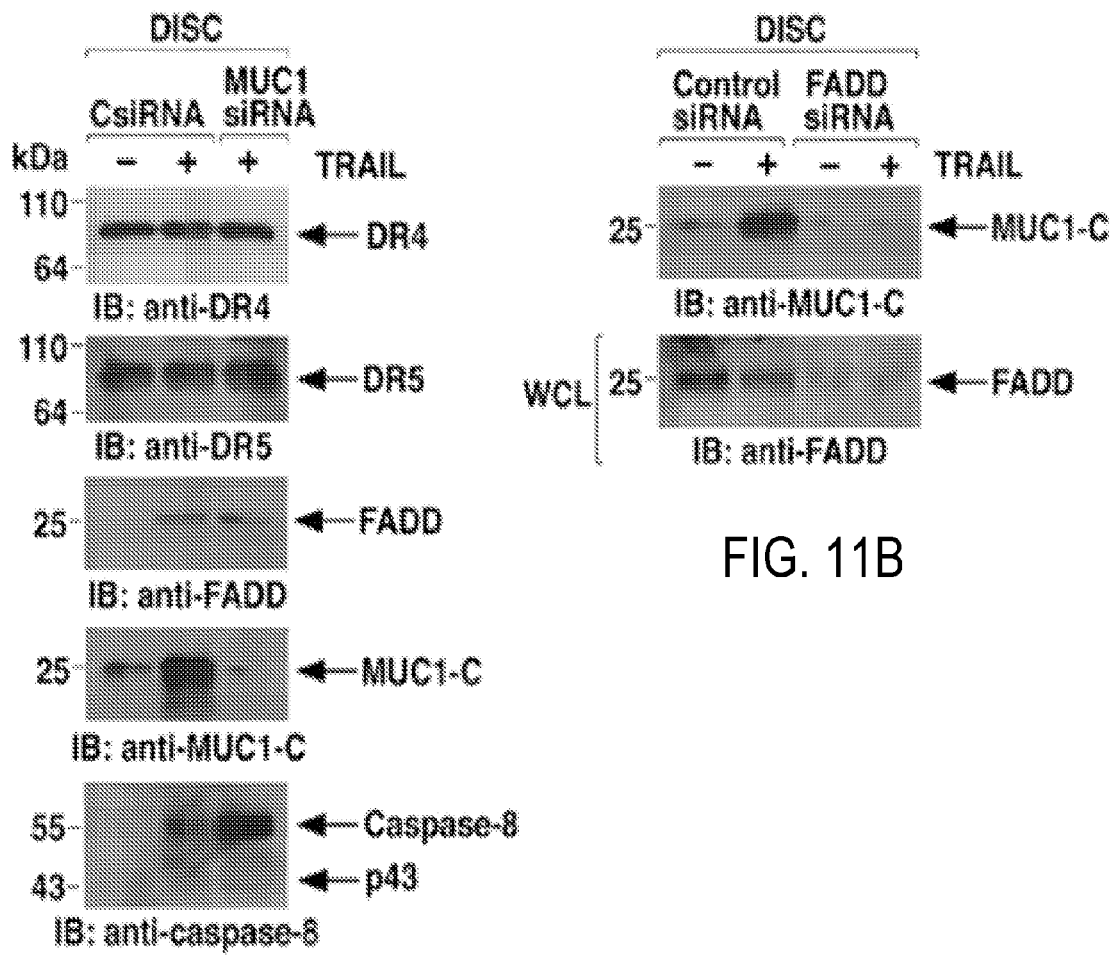
FIG. 10 depicts the amino acid sequence of a fragment of human caspase-8 (270-322) (SEQ ID NO:27).
FIGS. 11A-11D are a series of photographs of western blots depicting MUC1-C recruitment to the DISC and inhibition of recruitment of caspase-8 to the DISC.

MUC1-C includes a 72 amino acid cytoplasmic domain (CD) of MUC1 that interacts with β-catenin, IKKs and multiple kinases (FIG. 9A, upper panel). To determine whether MUC1-CD interacts directly with caspase-8, purified His-tagged MUC1-CD protein was incubated with GST or GST-caspase-8 immobilized on glutathione coated beads. Immunoblot analysis of adsorbates with anti-His tag antibodies showed that MUC1-CD binds to caspase-8 (FIG. 9A, lower panels). Caspase-8 contains an N-terminal region with two DEDs (amino acids 1-183), and the p18 (amino acids 217-374) and p10 (amino acids 385-480) cleavage products (FIG. 9B, upper panel). To define the region of caspase-8 that interacts with MUC1-CD, we incubated GST fusion proteins of caspase-8 fragments bound to glutathione-coated beads with His-MUC1-CD protein. Analysis of the adsorbates to the beads demonstrated that MUC1-CD binds to the region (amino acids 184-384) that includes caspase-8-p18 (FIG. 7B, lower panels). To further define the sequences in caspase-8-p18 that are responsible for the interaction, His-tagged protein fragments designated A (amino acids 184-269), B (amino acids 270-322), C (amino acids 323-384), and AB (amino acids 184-322) were generated (FIG. 9C, upper panel). Incubation of the His-caspase-8-p18 fragments with GST-MUC1-CD bound to glutathione coated beads demonstrated that MUC1-CD binds to caspase-8-p18-B (amino acids 270-322) (FIG. 9C, lower panels and FIG. 10). Additional binding studies using His-caspase-8(184-384) and GST-MUC1-CD fragments demonstrated that a fragment of MUC1-CD containing just amino acids 1-20 was able to interact with caspase-8 (FIG. 9D, upper). Moreover, the binding of MUC1-CD(1-20) to caspase-8-p18 was inhibited in the presence of a synthetic MUC1-CD(1-20) peptide (FIG. 9D, lower). These findings demonstrate that MUC1-CD interacts directly WITH caspase-8-p18 in vitro and that a fragment (amino acids 1-20) of the MUC1-CD is capable of inhibiting the interaction.

Example 6

MUC1-C Blocks Recruitment of Caspase-8 to the DISC

Binding of TRAIL to DR4/5 results in recruitment of FADD to the DISC and, in turn, FADD recruits caspase-8 (Falschlehner et al. (2007) *Int. J. Biochem. Cell Biol.* 39:1462-1475, the disclosure of which is incorporated herein by reference in its entirety). To determine if MUC1-C affects DISC function, MCF-10A cells were treated with a complex of Flag-tagged TRAIL, and the DISC complex was immunoprecipitated using an anti-Flag tag antibody. Silencing MUC1 expression using MUC1-specific siRNA had no effect on DR4/5 levels in the DISC (FIG. 11A). Silencing MUC1 expression also had little effect on TRAIL-induced recruitment of FADD (FIG. 11A). Notably, however, TRAIL treatment enhanced the recruitment of MUC1-C to the DISC (FIG. 11A). MUC1 was also found to inhibit recruitment of caspase-8 to the DISC (FIG. 11A). These results indicated that MUC1-C is recruited to the DISC by a mechanism independent of its interaction with caspase-8.

Figure 11C:
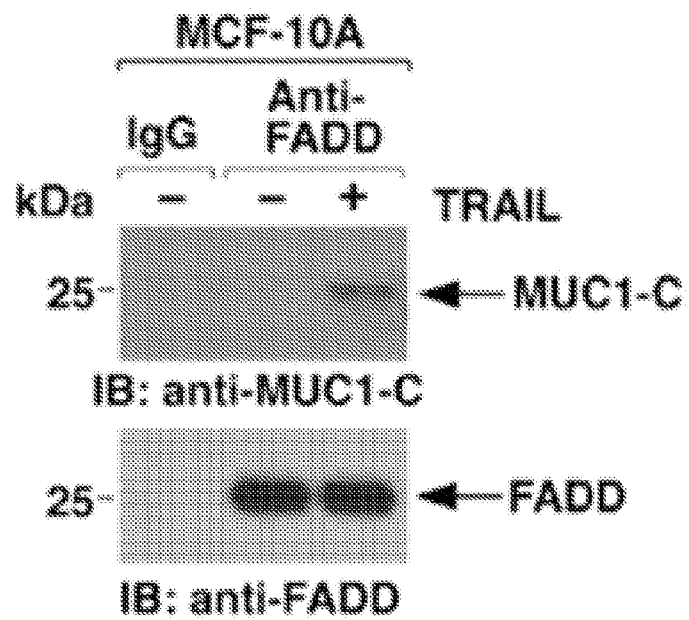
Figure 11D:
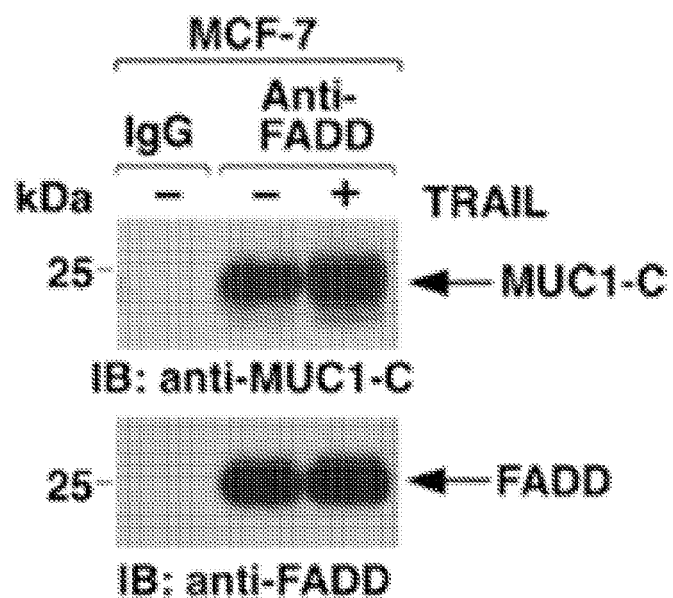

To determine whether the recruitment of MUC1-C is dependent on FADD, MCF-10A cells were treated with FADD-specific siRNA to silence FADD expression and then treated with TRAIL. Recruitment of MUC1-C to the DISC was inhibited when FADD expression was silenced (FIG. 11B). The results of coimmunoprecipitation studies further demonstrated that TRAIL induces the formation of MUC1-C-FADD complexes (FIG. 11C). Moreover, in MCF-7 cancer cells, MUC1-C constitutively associates with FADD at high levels and this interaction is increased following treatment of cells with TRAIL (FIG. 11D). These findings indicated that MUC1-C interacts with FADD.

Example 7

MUC1-CD Binds Directly to the FADD DED

To determine whether MUC1-C directly binds to FADD, GST-MUC1-CD or GST-MUC1-CD deletion mutant proteins bound to glutathione coated beads were incubated with purified FADD protein. Analysis of the adsorbates to the beads demonstrated that MUC1-CD and FADD interact directly (FIG. 12A). MUC1-CD(46-72), but not MUC1-CD (1-45), was found to bind to FADD (FIG. 12A). FADD contains a death domain (DD) that binds to DR4/5 and a DED that recruits caspase-8 to the DISC (FIG. 12B, upper panel). To define the region of FADD that confers the interaction, GST-FADD or GST-FADD deletion mutant proteins bound to glutathione beads (FIG. 12B, upper panel) were incubated with purified MUC1-CD protein. These binding studies confirmed the direct interaction between MUC1-CD and FADD and further demonstrated that, like caspase-8, MUC1-CD interacts with the FADD DED and not the DD (FIG. 12B, lower panel). Importantly, in competition experiments, incubation of GSTcaspase-8(1-183) with FADD protein, and then increasing amounts of MUC1-CD protein, was associated with a progressive decrease in the interaction between FADD and caspase-8 (1-183) (FIG. 12C), indicating that caspase-8 and MUC1-CD compete for binding to FADD. These findings indicate that FADD forms mutually exclusive complexes with MUC1-CD and caspase-8.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the present invention.

What is claimed is:

1. A method of identifying a compound that modulates the binding of MUC1 to caspase-8, the method comprising:
   contacting a MUC1 reagent with a caspase-8 reagent or a DED-containing protein reagent in the presence of a candidate compound; and
   determining whether the candidate compound modulates binding of the MUC1 reagent to the caspase-8 reagent.

2. The method of claim 1, wherein the DED-containing protein reagent comprises FADD or a DED-containing fragment thereof.

3. The method of claim 1, wherein the caspase-8 reagent comprises a full-length, unprocessed caspase-8.

4. The method of claim 3, wherein the full-length unprocessed caspase-8 comprises SEQ ID NO:5.

5. The method of claim 1, wherein the MUC1 reagent comprises the cytoplasmic domain of MUC1.

6. The method of claim 5, wherein the cytoplasmic domain of MUC1 comprises SEQ ID NO: 2.

7. The method of claim 1, wherein the MUC1 reagent comprises SEQ ID NO:3.

8. The method of claim 1, wherein the modulation is inhibition.

9. The method of claim 1, wherein the modulation is enhancement.

10. The method of claim 1, wherein the contacting occurs in a cell.

* * * * *

SEQUENCE LISTING

```
<160> NUMBER OF SEQ ID NOS: 35

<210> SEQ ID NO 1
<211> LENGTH: 203
<212> TYPE: PRT
<213> ORGANISM: Homo sapiens

<400> SEQUENCE: 1

Met Thr Pro Gly Thr Gln Ser Pro Phe Phe Leu Leu Leu Leu Leu Thr
 1               5                  10                  15

Val Leu Thr Val Val Thr Gly Ser Gly His Ala Ser Ser Thr Pro Gly
                20                  25                  30

Gly Glu Lys Glu Thr Ser Ala Thr Gln Arg Ser Ser Val Pro Ser Ser
            35                  40                  45

Thr Glu Lys Asn Ala Ile Pro Ala Pro Thr Thr Thr Lys Ser Cys Arg
        50                  55                  60

Glu Thr Phe Leu Lys Cys Phe Cys Arg Phe Ile Asn Lys Gly Val Phe
    65                  70                  75                  80

Trp Ala Ser Pro Ile Leu Ser Ser Val Ser Asp Val Pro Phe Pro Phe
                    85                  90                  95

Ser Ala Gln Ser Gly Ala Gly Val Pro Gly Trp Gly Ile Ala Leu Leu
                100                 105                 110

Val Leu Val Cys Val Leu Val Ala Leu Ala Ile Val Tyr Leu Ile Ala
            115                 120                 125

Leu Ala Val Cys Gln Cys Arg Arg Lys Asn Tyr Gly Gln Leu Asp Ile
        130                 135                 140

Phe Pro Ala Arg Asp Thr Tyr His Pro Met Ser Glu Tyr Pro Thr Tyr
145                 150                 155                 160

His Thr His Gly Arg Tyr Val Pro Pro Ser Ser Thr Asp Arg Ser Pro
                165                 170                 175

Tyr Glu Lys Val Ser Ala Gly Asn Gly Gly Ser Ser Leu Ser Tyr Thr
            180                 185                 190

Asn Pro Ala Val Ala Ala Thr Ser Ala Asn Leu
        195                 200

<210> SEQ ID NO 2
<211> LENGTH: 72
<212> TYPE: PRT
<213> ORGANISM: Homo sapiens
```

<400> SEQUENCE: 2

Cys Gln Cys Arg Arg Lys Asn Tyr Gly Gln Leu Asp Ile Phe Pro Ala
1               5                   10                  15

Arg Asp Thr Tyr His Pro Met Ser Glu Tyr Pro Thr Tyr His Thr His
            20                  25                  30

Gly Arg Tyr Val Pro Pro Ser Ser Thr Asp Arg Ser Pro Tyr Glu Lys
        35                  40                  45

Val Ser Ala Gly Asn Gly Gly Ser Ser Leu Ser Tyr Thr Asn Pro Ala
50                  55                  60

Val Ala Ala Thr Ser Ala Asn Leu
65              70

<210> SEQ ID NO 3
<211> LENGTH: 20
<212> TYPE: PRT
<213> ORGANISM: Homo sapiens

<400> SEQUENCE: 3

Cys Gln Cys Arg Arg Lys Asn Tyr Gly Gln Leu Asp Ile Phe Pro Ala
1               5                   10                  15

Arg Asp Thr Tyr
            20

<210> SEQ ID NO 4
<211> LENGTH: 27
<212> TYPE: PRT
<213> ORGANISM: Homo sapiens

<400> SEQUENCE: 4

Tyr Glu Lys Val Ser Ala Gly Asn Gly Gly Ser Ser Leu Ser Tyr Thr
1               5                   10                  15

Asn Pro Ala Val Ala Ala Thr Ser Ala Asn Leu
            20                  25

<210> SEQ ID NO 5
<211> LENGTH: 479
<212> TYPE: PRT
<213> ORGANISM: Homo sapiens

<400> SEQUENCE: 5

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
        115                 120                 125

Ser Lys Cys Lys Leu Asp Asp Asp Met Asn Leu Leu Asp Ile Phe Ile

```
                130                 135                 140
Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Glu Arg Ser Ser Leu Glu Gly Ser
                180                 185                 190

Pro Asp Glu Phe Ser Asn Gly Glu Glu Leu Cys Gly Val Met Thr Ile
                195                 200                 205

Ser Asp Ser Pro Arg Glu Gln Asp Ser Glu Ser Gln Thr Leu Asp Lys
                210                 215                 220

Val Tyr Gln Met Lys Ser Lys Pro Arg Gly Tyr Cys Leu Ile Ile Asn
225                 230                 235                 240

Asn His Asn Phe Ala Lys Ala Arg Glu Lys Val Pro Lys Leu His Ser
                245                 250                 255

Ile Arg Asp Arg Asn Gly Thr His Leu Asp Ala Gly Ala Leu Thr Thr
                260                 265                 270

Thr Phe Glu Glu Leu His Phe Glu Ile Lys Pro His Asp Asp Cys Thr
                275                 280                 285

Val Glu Gln Ile Tyr Glu Ile Leu Lys Ile Tyr Gln Leu Met Asp His
                290                 295                 300

Ser Asn Met Asp Cys Phe Ile Cys Cys Ile Leu Ser His Gly Asp Lys
305                 310                 315                 320

Gly Ile Ile Tyr Gly Thr Asp Gly Gln Glu Ala Pro Ile Tyr Glu Leu
                325                 330                 335

Thr Ser Gln Phe Thr Gly Leu Lys Cys Pro Ser Leu Ala Gly Lys Pro
                340                 345                 350

Lys Val Phe Phe Ile Gln Ala Cys Gln Gly Asp Asn Tyr Gln Lys Gly
                355                 360                 365

Ile Pro Val Glu Thr Asp Ser Glu Glu Gln Pro Tyr Leu Glu Met Asp
                370                 375                 380

Leu Ser Ser Pro Gln Thr Arg Tyr Ile Pro Asp Glu Ala Asp Phe Leu
385                 390                 395                 400

Leu Gly Met Ala Thr Val Asn Asn Cys Val Ser Tyr Arg Asn Pro Ala
                405                 410                 415

Glu Gly Thr Trp Tyr Ile Gln Ser Leu Cys Gln Ser Leu Arg Glu Arg
                420                 425                 430

Cys Pro Arg Gly Asp Asp Ile Leu Thr Ile Leu Thr Glu Val Asn Tyr
                435                 440                 445

Glu Val Ser Asn Lys Asp Asp Lys Lys Asn Met Gly Lys Gln Met Pro
450                 455                 460

Gln Pro Thr Phe Thr Leu Arg Lys Lys Leu Val Phe Pro Ser Asp
465                 470                 475

<210> SEQ ID NO 6
<211> LENGTH: 158
<212> TYPE: PRT
<213> ORGANISM: Homo sapiens

<400> SEQUENCE: 6

Ser Glu Ser Gln Thr Leu Asp Lys Val Tyr Gln Met Lys Ser Lys Pro
1               5                   10                  15

Arg Gly Tyr Cys Leu Ile Ile Asn Asn His Asn Phe Ala Lys Ala Arg
                20                  25                  30
```

Glu Lys Val Pro Lys Leu His Ser Ile Arg Asp Arg Asn Gly Thr His
         35                   40                  45

Leu Asp Ala Gly Ala Leu Thr Thr Thr Phe Glu Glu Leu His Phe Glu
 50                      55                  60

Ile Lys Pro His Asp Asp Cys Thr Val Glu Gln Ile Tyr Glu Ile Leu
 65                  70                  75                  80

Lys Ile Tyr Gln Leu Met Asp His Ser Asn Met Asp Cys Phe Ile Cys
                 85                  90                  95

Cys Ile Leu Ser His Gly Asp Lys Gly Ile Ile Tyr Gly Thr Asp Gly
             100                 105                 110

Gln Glu Ala Pro Ile Tyr Glu Leu Thr Ser Gln Phe Thr Gly Leu Lys
         115                 120                 125

Cys Pro Ser Leu Ala Gly Lys Pro Lys Val Phe Phe Ile Gln Ala Cys
130                 135                 140

Gln Gly Asp Asn Tyr Gln Lys Gly Ile Pro Val Glu Thr Asp
145                 150                 155

<210> SEQ ID NO 7
<211> LENGTH: 208
<212> TYPE: PRT
<213> ORGANISM: Homo sapiens

<400> SEQUENCE: 7

Met Asp Pro Phe Leu Val Leu Leu His Ser Val Ser Ser Ser Leu Ser
 1               5                  10                  15

Ser Ser Glu Leu Thr Glu Leu Lys Phe Leu Cys Leu Gly Arg Val Gly
             20                  25                  30

Lys Arg Lys Leu Glu Arg Val Gln Ser Gly Leu Asp Leu Phe Ser Met
         35                  40                  45

Leu Leu Glu Gln Asn Asp Leu Glu Pro Gly His Thr Glu Leu Leu Arg
 50                  55                  60

Glu Leu Leu Ala Ser Leu Arg Arg His Asp Leu Leu Arg Arg Val Asp
 65                  70                  75                  80

Asp Phe Glu Ala Gly Ala Ala Ala Gly Ala Ala Pro Gly Glu Glu Asp
                 85                  90                  95

Leu Cys Ala Ala Phe Asn Val Ile Cys Asp Asn Val Gly Lys Asp Trp
             100                 105                 110

Arg Arg Leu Ala Arg Gln Leu Lys Val Ser Asp Thr Lys Ile Asp Ser
         115                 120                 125

Ile Glu Asp Arg Tyr Pro Arg Asn Leu Thr Glu Arg Val Arg Glu Ser
130                 135                 140

Leu Arg Ile Trp Lys Asn Thr Glu Lys Glu Asn Ala Thr Val Ala His
145                 150                 155                 160

Leu Val Gly Ala Leu Arg Ser Cys Gln Met Asn Leu Val Ala Asp Leu
                 165                 170                 175

Val Gln Glu Val Gln Gln Ala Arg Asp Leu Gln Asn Arg Ser Gly Ala
             180                 185                 190

Met Ser Pro Met Ser Trp Asn Ser Asp Ala Ser Thr Ser Glu Ala Ser
         195                 200                 205

<210> SEQ ID NO 8
<211> LENGTH: 79
<212> TYPE: PRT
<213> ORGANISM: Homo sapiens

<400> SEQUENCE: 8

```
Pro Phe Leu Val Leu Leu His Ser Val Ser Ser Leu Ser Ser Ser
1               5                   10                  15

Glu Leu Thr Glu Leu Lys Phe Leu Cys Leu Gly Arg Val Gly Lys Arg
            20                  25                  30

Lys Leu Glu Arg Val Gln Ser Gly Leu Asp Leu Phe Ser Met Leu Leu
        35                  40                  45

Glu Gln Asn Asp Leu Glu Pro Gly His Thr Glu Leu Leu Arg Glu Leu
    50                  55                  60

Leu Ala Ser Leu Arg Arg His Asp Leu Leu Arg Arg Val Asp Asp
65              70                  75
```

<210> SEQ ID NO 9
<211> LENGTH: 521
<212> TYPE: PRT
<213> ORGANISM: Homo sapiens

<400> SEQUENCE: 9

```
Met Lys Ser Gln Gly Gln His Trp Tyr Ser Ser Asp Lys Asn Cys
1               5                   10                  15

Lys Val Ser Phe Arg Glu Lys Leu Leu Ile Ile Asp Ser Asn Leu Gly
            20                  25                  30

Val Gln Asp Val Glu Asn Leu Lys Phe Leu Cys Ile Gly Leu Val Pro
        35                  40                  45

Asn Lys Lys Leu Glu Lys Ser Ser Ser Ala Ser Asp Val Phe Glu His
    50                  55                  60

Leu Leu Ala Glu Asp Leu Leu Ser Glu Glu Asp Pro Phe Phe Leu Ala
65              70                  75                  80

Glu Leu Leu Tyr Ile Ile Arg Gln Lys Lys Leu Leu Gln His Leu Asn
                85                  90                  95

Cys Thr Lys Glu Glu Val Glu Arg Leu Leu Pro Thr Gln Arg Gln Val
            100                 105                 110

Ser Leu Phe Arg Asn Leu Leu Tyr Glu Leu Ser Glu Gly Ile Asp Ser
        115                 120                 125

Glu Asn Leu Lys Asp Met Ile Phe Leu Leu Lys Asp Ser Leu Pro Lys
    130                 135                 140

Thr Glu Met Thr Ser Leu Ser Phe Leu Ala Phe Leu Glu Lys Gln Gly
145             150                 155                 160

Lys Ile Asp Glu Asp Asn Leu Thr Cys Leu Glu Asp Leu Cys Lys Thr
                165                 170                 175

Val Val Pro Lys Leu Leu Arg Asn Ile Glu Lys Tyr Lys Arg Glu Lys
            180                 185                 190

Ala Ile Gln Ile Val Thr Pro Pro Val Asp Lys Glu Ala Glu Ser Tyr
        195                 200                 205

Gln Gly Glu Glu Glu Leu Val Ser Gln Thr Asp Val Lys Thr Phe Leu
    210                 215                 220

Glu Ala Leu Pro Gln Glu Ser Trp Gln Asn Lys His Ala Gly Ser Asn
225             230                 235                 240

Gly Asn Arg Ala Thr Asn Gly Ala Pro Ser Leu Val Ser Arg Gly Met
                245                 250                 255

Gln Gly Ala Ser Ala Asn Thr Leu Asn Ser Glu Thr Ser Thr Lys Arg
            260                 265                 270

Ala Ala Val Tyr Arg Met Asn Arg Asn His Arg Gly Leu Cys Val Ile
        275                 280                 285

Val Asn Asn His Ser Phe Thr Ser Leu Lys Asp Arg Gln Gly Thr His
    290                 295                 300
```

```
Lys Asp Ala Glu Ile Leu Ser His Val Phe Gln Trp Leu Gly Phe Thr
305                 310                 315                 320

Val His Ile His Asn Asn Val Thr Lys Val Glu Met Glu Met Val Leu
                325                 330                 335

Gln Lys Gln Lys Cys Asn Pro Ala His Ala Asp Gly Asp Cys Phe Val
            340                 345                 350

Phe Cys Ile Leu Thr His Gly Arg Phe Gly Ala Val Tyr Ser Ser Asp
        355                 360                 365

Glu Ala Leu Ile Pro Ile Arg Glu Ile Met Ser His Phe Thr Ala Leu
    370                 375                 380

Gln Cys Pro Arg Leu Ala Glu Lys Pro Lys Leu Phe Phe Ile Gln Ala
385                 390                 395                 400

Cys Gln Gly Glu Glu Ile Gln Pro Ser Val Ser Ile Glu Ala Asp Ala
                405                 410                 415

Leu Asn Pro Glu Gln Ala Pro Thr Ser Leu Gln Asp Ser Ile Pro Ala
            420                 425                 430

Glu Ala Asp Phe Leu Leu Gly Leu Ala Thr Val Pro Gly Tyr Val Ser
        435                 440                 445

Phe Arg His Val Glu Glu Gly Ser Trp Tyr Ile Gln Ser Leu Cys Asn
    450                 455                 460

His Leu Lys Lys Leu Val Pro Arg Met Leu Lys Phe Leu Glu Lys Thr
465                 470                 475                 480

Met Glu Ile Arg Gly Arg Lys Arg Thr Val Trp Gly Ala Lys Gln Ile
                485                 490                 495

Ser Ala Thr Ser Leu Pro Thr Ala Ile Ser Ala Gln Thr Pro Arg Pro
            500                 505                 510

Pro Met Arg Arg Trp Ser Ser Val Ser
            515                 520

<210> SEQ ID NO 10
<211> LENGTH: 79
<212> TYPE: PRT
<213> ORGANISM: Homo sapiens

<400> SEQUENCE: 10

Val Ser Phe Arg Glu Lys Leu Leu Ile Ile Asp Ser Asn Leu Gly Val
1               5                   10                  15

Gln Asp Val Glu Asn Leu Lys Phe Leu Cys Ile Gly Leu Val Pro Asn
            20                  25                  30

Lys Lys Leu Glu Lys Ser Ser Ala Ser Asp Val Phe Glu His Leu
        35                  40                  45

Leu Ala Glu Asp Leu Leu Ser Glu Glu Asp Pro Phe Phe Leu Ala Glu
    50                  55                  60

Leu Leu Tyr Ile Ile Arg Gln Lys Lys Leu Leu Gln His Leu Asn
65                  70                  75

<210> SEQ ID NO 11
<211> LENGTH: 318
<212> TYPE: PRT
<213> ORGANISM: Homo sapiens

<400> SEQUENCE: 11

Met Ala Gly Leu Lys Arg Arg Ala Ser Gln Val Trp Pro Glu Glu His
1               5                   10                  15

Gly Glu Gln Glu His Gly Leu Tyr Ser Leu His Arg Met Phe Asp Ile
            20                  25                  30
```

Val Gly Thr His Leu Thr His Arg Asp Val Arg Val Leu Ser Phe Leu
            35                  40                  45

Phe Val Asp Val Ile Asp Asp His Glu Arg Gly Leu Ile Arg Asn Gly
 50                  55                  60

Arg Asp Phe Leu Leu Ala Leu Glu Arg Gln Gly Arg Cys Asp Glu Ser
 65                  70                  75                  80

Asn Phe Arg Gln Val Leu Gln Leu Leu Arg Ile Ile Thr Arg His Asp
                 85                  90                  95

Leu Leu Pro Tyr Val Thr Leu Lys Arg Arg Ala Val Cys Pro Asp
             100                 105                 110

Leu Val Asp Lys Tyr Leu Glu Thr Ser Ile Arg Tyr Val Thr Pro
             115                 120                 125

Arg Ala Leu Ser Asp Pro Glu Pro Arg Pro Gln Pro Ser Lys Thr
 130                 135                 140

Val Pro Pro His Tyr Pro Val Val Cys Cys Pro Thr Ser Gly Pro Gln
145                 150                 155                 160

Met Cys Ser Lys Arg Pro Ala Arg Gly Arg Ala Thr Leu Gly Ser Gln
                165                 170                 175

Arg Lys Arg Arg Lys Ser Val Thr Pro Asp Pro Lys Glu Lys Gln Thr
            180                 185                 190

Cys Asp Ile Arg Leu Arg Val Arg Ala Glu Tyr Cys Gln His Glu Thr
            195                 200                 205

Ala Leu Gln Gly Asn Val Phe Ser Asn Lys Gln Asp Pro Leu Glu Arg
 210                 215                 220

Gln Phe Glu Arg Phe Asn Gln Ala Asn Thr Ile Leu Lys Ser Arg Asp
225                 230                 235                 240

Leu Gly Ser Ile Ile Cys Asp Ile Lys Phe Ser Glu Leu Thr Tyr Leu
                245                 250                 255

Asp Ala Phe Trp Arg Asp Tyr Ile Asn Gly Ser Leu Leu Glu Ala Leu
            260                 265                 270

Lys Gly Val Phe Ile Thr Asp Ser Leu Lys Gln Ala Val Gly His Glu
            275                 280                 285

Ala Ile Lys Leu Leu Val Asn Val Asp Glu Glu Asp Tyr Glu Leu Gly
 290                 295                 300

Arg Gln Lys Leu Leu Arg Asn Leu Met Leu Gln Ala Leu Pro
305                 310                 315

<210> SEQ ID NO 12
<211> LENGTH: 79
<212> TYPE: PRT
<213> ORGANISM: Homo sapiens

<400> SEQUENCE: 12

Ser Leu His Arg Met Phe Asp Ile Val Gly Thr His Leu Thr His Arg
 1               5                  10                  15

Asp Val Arg Val Leu Ser Phe Leu Phe Val Asp Val Ile Asp Asp His
                20                  25                  30

Glu Arg Gly Leu Ile Arg Asn Gly Arg Asp Phe Leu Leu Ala Leu Glu
            35                  40                  45

Arg Gln Gly Arg Cys Asp Glu Ser Asn Phe Arg Gln Val Leu Gln Leu
 50                  55                  60

Leu Arg Ile Ile Thr Arg His Asp Leu Leu Pro Tyr Val Thr Leu
 65                  70                  75

<210> SEQ ID NO 13
<211> LENGTH: 449
<212> TYPE: PRT
<213> ORGANISM: Homo sapiens

<400> SEQUENCE: 13

```
Met Glu Glu Pro Gln Lys Ser Tyr Val Asn Thr Met Asp Leu Glu Arg
 1               5                  10                  15

Asp Glu Pro Leu Lys Ser Thr Gly Pro Gln Ile Ser Val Ser Glu Phe
            20                  25                  30

Ser Cys His Cys Cys Tyr Asp Ile Leu Val Asn Pro Thr Thr Leu Asn
        35                  40                  45

Cys Gly His Ser Phe Cys Arg His Cys Leu Ala Leu Trp Trp Ala Ser
    50                  55                  60

Ser Lys Lys Thr Glu Cys Pro Glu Cys Arg Glu Lys Trp Glu Gly Phe
65                  70                  75                  80

Pro Lys Val Ser Ile Leu Leu Arg Asp Ala Ile Glu Lys Leu Phe Pro
                85                  90                  95

Asp Ala Ile Arg Leu Arg Phe Glu Asp Ile Gln Gln Asn Asn Asp Ile
            100                 105                 110

Val Gln Ser Leu Ala Ala Phe Gln Lys Tyr Gly Asn Asp Gln Ile Pro
        115                 120                 125

Leu Ala Pro Asn Thr Gly Arg Ala Asn Gln Gln Met Gly Gly Gly Phe
    130                 135                 140

Phe Ser Gly Val Leu Thr Ala Leu Thr Gly Val Ala Val Val Leu Leu
145                 150                 155                 160

Val Tyr His Trp Ser Ser Arg Glu Ser Glu His Asp Leu Leu Val His
                165                 170                 175

Lys Ala Val Ala Lys Trp Thr Ala Glu Val Val Leu Trp Leu Glu
            180                 185                 190

Gln Leu Gly Pro Trp Ala Ser Leu Tyr Arg Glu Arg Phe Leu Ser Glu
        195                 200                 205

Arg Val Asn Gly Arg Leu Leu Leu Thr Leu Thr Glu Glu Glu Phe Ser
    210                 215                 220

Lys Thr Pro Tyr Thr Ile Glu Asn Ser Ser His Arg Arg Ala Ile Leu
225                 230                 235                 240

Met Glu Leu Glu Arg Val Lys Ala Leu Gly Val Lys Pro Pro Gln Asn
                245                 250                 255

Leu Trp Glu Tyr Lys Ala Val Asn Pro Gly Arg Ser Leu Phe Leu Leu
            260                 265                 270

Tyr Ala Leu Lys Ser Ser Pro Arg Leu Ser Leu Leu Tyr Leu Tyr Leu
        275                 280                 285

Phe Asp Tyr Thr Asp Thr Phe Leu Pro Phe Ile His Thr Ile Cys Pro
    290                 295                 300

Leu Gln Glu Asp Ser Ser Gly Glu Asp Ile Val Thr Lys Leu Leu Asp
305                 310                 315                 320

Leu Lys Glu Pro Thr Trp Lys Gln Trp Arg Glu Phe Leu Val Lys Tyr
                325                 330                 335

Ser Phe Leu Pro Tyr Gln Leu Ile Ala Glu Phe Ala Trp Asp Trp Leu
            340                 345                 350

Glu Val His Tyr Trp Thr Ser Arg Phe Leu Ile Ile Asn Ala Met Leu
        355                 360                 365

Leu Ser Val Leu Glu Leu Phe Ser Phe Trp Arg Ile Trp Ser Arg Ser
    370                 375                 380
```

Glu Leu Lys Thr Val Pro Gln Arg Met Trp Ser His Phe Trp Lys Val
385                 390                 395                 400

Ser Thr Gln Gly Leu Phe Val Ala Met Phe Trp Pro Leu Ile Pro Gln
            405                 410                 415

Phe Val Cys Asn Cys Leu Phe Tyr Trp Ala Leu Tyr Phe Asn Pro Ile
        420                 425                 430

Ile Asn Ile Asp Leu Val Val Lys Glu Leu Arg Arg Leu Glu Thr Gln
        435                 440                 445

Val

<210> SEQ ID NO 14
<211> LENGTH: 72
<212> TYPE: PRT
<213> ORGANISM: Homo sapiens

<400> SEQUENCE: 14

Ala Leu Lys Ser Ser Pro Arg Leu Ser Leu Leu Tyr Leu Tyr Leu Phe
1               5                   10                  15

Asp Tyr Thr Asp Thr Phe Leu Pro Phe Ile His Thr Ile Cys Pro Leu
            20                  25                  30

Gln Glu Asp Ser Ser Gly Glu Asp Ile Val Thr Lys Leu Leu Asp Leu
        35                  40                  45

Lys Glu Pro Thr Trp Lys Gln Trp Arg Glu Phe Leu Val Lys Tyr Ser
50                  55                  60

Phe Leu Pro Tyr Gln Leu Ile Ala
65                  70

<210> SEQ ID NO 15
<211> LENGTH: 326
<212> TYPE: PRT
<213> ORGANISM: Homo sapiens

<400> SEQUENCE: 15

Met Ala Leu Ser Gly Ser Thr Pro Ala Pro Cys Trp Glu Glu Asp Glu
1               5                   10                  15

Cys Leu Asp Tyr Tyr Gly Met Leu Ser Leu His Arg Met Phe Glu Val
            20                  25                  30

Val Gly Gly Gln Leu Thr Glu Cys Glu Leu Glu Leu Leu Ala Phe Leu
        35                  40                  45

Leu Asp Glu Ala Pro Gly Ala Ala Gly Gly Leu Ala Arg Ala Arg Ser
50                  55                  60

Gly Leu Glu Leu Leu Leu Glu Leu Glu Arg Arg Gly Gln Cys Asp Glu
65                  70                  75                  80

Ser Asn Leu Arg Leu Leu Gly Gln Leu Leu Arg Val Leu Ala Arg His
            85                  90                  95

Asp Leu Leu Pro His Leu Ala Arg Lys Arg Arg Arg Pro Val Ser Pro
        100                 105                 110

Glu Arg Tyr Ser Tyr Gly Thr Ser Ser Ser Lys Thr Glu Gly
        115                 120                 125         Gly

Ser Cys Arg Arg Arg Arg Gln Ser Ser Ser Ala Asn Ser Gln Gln
130                 135                 140

Gly Gln Trp Glu Thr Gly Ser Pro Thr Lys Arg Gln Arg Arg Ser
145                 150                 155                 160

Arg Gly Arg Pro Ser Gly Gly Ala Arg Arg Arg Gly Ala Pro
            165                 170                 175

Ala Ala Pro Gln Gln Gln Ser Glu Pro Ala Arg Pro Ser Ser Glu Gly

```
                    180                 185                 190
Lys Val Thr Cys Asp Ile Arg Leu Arg Val Arg Ala Glu Tyr Cys Glu
                195                 200                 205

His Gly Pro Ala Leu Glu Gln Gly Val Ala Ser Arg Pro Gln Ala
            210                 215                 220

Leu Ala Arg Gln Leu Asp Val Phe Gly Gln Ala Thr Ala Val Leu Arg
225                 230                 235                 240

Ser Arg Asp Leu Gly Ser Val Val Cys Asp Ile Lys Phe Ser Glu Leu
                245                 250                 255

Ser Tyr Leu Asp Ala Phe Trp Gly Asp Tyr Leu Ser Gly Ala Leu Leu
            260                 265                 270

Gln Ala Leu Arg Gly Val Phe Leu Thr Glu Ala Leu Arg Glu Ala Val
            275                 280                 285

Gly Arg Glu Ala Val Arg Leu Leu Val Ser Val Asp Glu Ala Asp Tyr
            290                 295                 300

Glu Ala Gly Arg Arg Leu Leu Leu Met Glu Glu Glu Gly Gly Arg
305                 310                 315                 320

Arg Pro Thr Glu Ala Ser
                325

<210> SEQ ID NO 16
<211> LENGTH: 80
<212> TYPE: PRT
<213> ORGANISM: Homo sapiens

<400> SEQUENCE: 16

Ser Leu His Arg Met Phe Glu Val Val Gly Gly Gln Leu Thr Glu Cys
  1               5                  10                  15

Glu Leu Glu Leu Leu Ala Phe Leu Leu Asp Glu Ala Pro Gly Ala Ala
                 20                  25                  30

Gly Gly Leu Ala Arg Ala Arg Ser Gly Leu Glu Leu Leu Glu Leu
             35                  40                  45

Glu Arg Arg Gly Gln Cys Asp Glu Ser Asn Leu Arg Leu Leu Gly Gln
         50                  55                  60

Leu Leu Arg Val Leu Ala Arg His Asp Leu Leu Pro His Leu Ala Arg
65                  70                  75                  80

<210> SEQ ID NO 17
<211> LENGTH: 1030
<212> TYPE: PRT
<213> ORGANISM: Homo sapiens

<400> SEQUENCE: 17

Met Lys Gln Val Pro Asn Pro Leu Pro Lys Val Leu Ser Arg Arg Gly
  1               5                  10                  15

Val Gly Ala Gly Leu Glu Ala Ala Glu Arg Glu Ser Phe Glu Arg Thr
                 20                  25                  30

Gln Thr Val Ser Ile Asn Lys Ala Ile Asn Thr Gln Glu Val Ala Val
             35                  40                  45

Lys Glu Lys His Ala Arg Thr Cys Ile Leu Gly Thr His His Glu Lys
         50                  55                  60

Gly Ala Gln Thr Phe Trp Ser Val Val Asn Arg Leu Pro Leu Ser Ser
65                  70                  75                  80

Asn Ala Val Leu Cys Trp Lys Phe Cys His Val Phe His Lys Leu Leu
                 85                  90                  95

Arg Asp Gly His Pro Asn Val Leu Lys Asp Ser Leu Arg Tyr Arg Asn
```

```
            100                 105                 110
Glu Leu Ser Asp Met Ser Arg Met Trp Gly His Leu Ser Glu Gly Tyr
            115                 120                 125

Gly Gln Leu Cys Ser Ile Tyr Leu Lys Leu Leu Arg Thr Lys Met Glu
130                 135                 140

Tyr His Thr Lys Asn Pro Arg Phe Pro Gly Asn Leu Gln Met Ser Asp
145                 150                 155                 160

Arg Gln Leu Asp Glu Ala Gly Glu Ser Asp Val Asn Asn Phe Phe Gln
                165                 170                 175

Leu Thr Val Glu Met Phe Asp Tyr Leu Glu Cys Glu Leu Asn Leu Phe
            180                 185                 190

Gln Thr Val Phe Asn Ser Leu Asp Met Ser Arg Ser Val Ser Val Thr
        195                 200                 205

Ala Ala Gly Gln Cys Arg Leu Ala Pro Leu Ile Gln Val Ile Leu Asp
210                 215                 220

Cys Ser His Leu Tyr Asp Tyr Thr Val Lys Leu Leu Phe Lys Leu His
225                 230                 235                 240

Ser Cys Leu Pro Ala Asp Thr Leu Gln Gly His Arg Asp Arg Phe Met
                245                 250                 255

Glu Gln Phe Thr Lys Leu Lys Asp Leu Phe Tyr Arg Ser Ser Asn Leu
            260                 265                 270

Gln Tyr Phe Lys Arg Leu Ile Gln Ile Pro Gln Leu Pro Glu Asn Pro
        275                 280                 285

Pro Asn Phe Leu Arg Ala Ser Ala Leu Ser Glu His Ile Ser Pro Val
290                 295                 300

Val Val Ile Pro Ala Glu Ala Ser Ser Pro Asp Ser Glu Pro Val Leu
305                 310                 315                 320

Glu Lys Asp Asp Leu Met Asp Met Asp Ala Ser Gln Gln Asn Leu Phe
                325                 330                 335

Asp Asn Lys Phe Asp Asp Ile Phe Gly Ser Ser Phe Ser Ser Asp Pro
            340                 345                 350

Phe Asn Phe Asn Ser Gln Asn Gly Val Asn Lys Asp Glu Lys Asp His
        355                 360                 365

Leu Ile Glu Arg Leu Tyr Arg Glu Ile Ser Gly Leu Lys Ala Gln Leu
370                 375                 380

Glu Asn Met Lys Thr Glu Ser Gln Arg Val Val Leu Gln Leu Lys Gly
385                 390                 395                 400

His Val Ser Glu Leu Glu Ala Asp Leu Ala Glu Gln Gln His Leu Arg
                405                 410                 415

Gln Gln Ala Ala Asp Asp Cys Glu Phe Leu Arg Ala Glu Leu Asp Glu
            420                 425                 430

Leu Arg Arg Gln Arg Glu Asp Thr Glu Lys Ala Gln Arg Ser Leu Ser
        435                 440                 445

Glu Ile Glu Arg Lys Ala Gln Ala Asn Glu Gln Arg Tyr Ser Lys Leu
450                 455                 460

Lys Glu Lys Tyr Ser Glu Leu Val Gln Asn His Ala Asp Leu Leu Arg
465                 470                 475                 480

Lys Asn Ala Glu Val Thr Lys Gln Val Ser Met Ala Arg Gln Ala Gln
                485                 490                 495

Val Asp Leu Glu Arg Glu Lys Lys Glu Leu Glu Asp Ser Leu Glu Arg
            500                 505                 510

Ile Ser Asp Gln Gly Gln Arg Lys Thr Gln Glu Gln Leu Glu Val Leu
        515                 520                 525
```

-continued

Glu Ser Leu Lys Gln Glu Leu Ala Thr Ser Gln Arg Glu Leu Gln Val
    530                 535                 540

Leu Gln Gly Ser Leu Glu Thr Ser Ala Gln Ser Glu Ala Asn Trp Ala
545                 550                 555                 560

Ala Glu Phe Ala Glu Leu Glu Lys Glu Arg Asp Ser Leu Val Ser Gly
                565                 570                 575

Ala Ala His Arg Glu Glu Glu Leu Ser Ala Leu Arg Lys Glu Leu Gln
            580                 585                 590

Asp Thr Gln Leu Lys Leu Ala Ser Thr Glu Glu Ser Met Cys Gln Leu
        595                 600                 605

Ala Lys Asp Gln Arg Lys Met Leu Leu Val Gly Ser Arg Lys Ala Ala
610                 615                 620

Glu Gln Val Ile Gln Asp Ala Leu Asn Gln Leu Glu Glu Pro Pro Leu
625                 630                 635                 640

Ile Ser Cys Ala Gly Ser Ala Asp His Leu Leu Ser Thr Val Thr Ser
                645                 650                 655

Ile Ser Ser Cys Ile Glu Gln Leu Glu Lys Ser Trp Ser Gln Tyr Leu
            660                 665                 670

Ala Cys Pro Glu Asp Ile Ser Gly Leu Leu His Ser Ile Thr Leu Leu
        675                 680                 685

Ala His Leu Thr Ser Asp Ala Ile Ala His Gly Ala Thr Thr Cys Leu
690                 695                 700

Arg Ala Pro Pro Glu Pro Ala Asp Ser Leu Thr Glu Ala Cys Lys Gln
705                 710                 715                 720

Tyr Gly Arg Glu Thr Leu Ala Tyr Leu Ala Ser Leu Glu Glu Glu Gly
                725                 730                 735

Ser Leu Glu Asn Ala Asp Ser Thr Ala Met Arg Asn Cys Leu Ser Lys
            740                 745                 750

Ile Lys Ala Ile Gly Glu Glu Leu Leu Pro Arg Gly Leu Asp Ile Lys
        755                 760                 765

Gln Glu Glu Leu Gly Asp Leu Val Asp Lys Glu Met Ala Ala Thr Ser
770                 775                 780

Ala Ala Ile Glu Thr Ala Thr Ala Arg Ile Glu Glu Met Leu Ser Lys
785                 790                 795                 800

Ser Arg Ala Gly Asp Thr Gly Val Lys Leu Glu Val Asn Glu Arg Ile
                805                 810                 815

Leu Gly Cys Cys Thr Ser Leu Met Gln Ala Ile Gln Val Leu Ile Val
            820                 825                 830

Ala Ser Lys Asp Leu Gln Arg Glu Ile Val Glu Ser Gly Arg Gly Thr
        835                 840                 845

Ala Ser Pro Lys Glu Phe Tyr Ala Lys Asn Ser Arg Trp Thr Glu Gly
850                 855                 860

Leu Ile Ser Ala Ser Lys Ala Val Gly Trp Gly Ala Thr Val Met Val
865                 870                 875                 880

Asp Ala Ala Asp Leu Val Val Gln Gly Arg Gly Lys Phe Glu Glu Leu
                885                 890                 895

Met Val Cys Ser His Glu Ile Ala Ala Ser Thr Ala Gln Leu Val Ala
            900                 905                 910

Ala Ser Lys Val Lys Ala Asp Lys Asp Ser Pro Asn Leu Ala Gln Leu
        915                 920                 925

Gln Gln Ala Ser Arg Gly Val Asn Gln Ala Thr Ala Gly Val Val Ala
930                 935                 940

Ser Thr Ile Ser Gly Lys Ser Gln Ile Glu Glu Thr Asp Asn Met Asp
945                 950                 955                 960

Phe Ser Ser Met Thr Leu Thr Gln Ile Lys Arg Gln Glu Met Asp Ser
                965                 970                 975

Gln Val Arg Val Leu Glu Leu Glu Asn Glu Leu Gln Lys Glu Arg Gln
            980                 985                 990

Lys Leu Gly Glu Leu Arg Lys Lys His Tyr Glu Leu Ala Gly Val Ala
        995                 1000                1005

Glu Gly Trp Glu Gly Thr Glu Ala Ser Pro Pro Thr Leu Gln Glu
    1010                1015                1020

Val Val Thr Glu Lys Glu
1025                1030

<210> SEQ ID NO 18
<211> LENGTH: 81
<212> TYPE: PRT
<213> ORGANISM: Homo sapiens

<400> SEQUENCE: 18

Ser Glu Leu Glu Ala Asp Leu Ala Glu Gln Gln His Leu Arg Gln Gln
1               5                   10                  15

Ala Ala Asp Asp Cys Glu Phe Leu Arg Ala Glu Leu Asp Glu Leu Arg
            20                  25                  30

Arg Gln Arg Glu Asp Thr Glu Lys Ala Gln Arg Ser Leu Ser Glu Ile
        35                  40                  45

Glu Arg Lys Ala Gln Ala Asn Glu Gln Arg Tyr Ser Lys Leu Lys Glu
    50                  55                  60

Lys Tyr Ser Glu Leu Val Gln Asn His Ala Asp Leu Leu Arg Lys Asn
65                  70                  75                  80

Ala

<210> SEQ ID NO 19
<211> LENGTH: 246
<212> TYPE: PRT
<213> ORGANISM: Homo sapiens

<400> SEQUENCE: 19

Met Thr Leu Gln Trp Thr Ala Val Ala Thr Phe Leu Tyr Ala Glu Val
1               5                   10                  15

Phe Val Val Leu Leu Leu Cys Ile Pro Phe Ile Ser Pro Lys Arg Trp
            20                  25                  30

Gln Lys Ile Phe Lys Ser Arg Leu Val Glu Leu Leu Val Ser Tyr Gly
        35                  40                  45

Asn Thr Phe Phe Val Val Leu Ile Val Ile Leu Val Leu Leu Val Ile
    50                  55                  60

Asp Ala Val Arg Glu Ile Arg Lys Tyr Asp Asp Val Thr Glu Lys Val
65                  70                  75                  80

Asn Leu Gln Asn Asn Pro Gly Ala Met Glu His Phe His Met Lys Leu
            85                  90                  95

Phe Arg Ala Gln Arg Asn Leu Tyr Ile Ala Gly Phe Ser Leu Leu Leu
        100                 105                 110

Ser Phe Leu Leu Arg Arg Leu Val Thr Leu Ile Ser Gln Gln Ala Thr
    115                 120                 125

Leu Leu Ala Ser Asn Glu Ala Phe Lys Lys Gln Ala Glu Ser Ala Ser
130                 135                 140

Glu Ala Ala Lys Lys Tyr Met Glu Glu Asn Asp Gln Leu Lys Lys Gly

```
                  145                 150                 155                 160
        Ala Ala Val Asp Gly Gly Lys Leu Asp Val Gly Asn Ala Glu Val Lys
                        165                 170                 175

Leu Glu Glu Glu Asn Arg Ser Leu Lys Ala Asp Leu Gln Lys Leu Lys
                        180                 185                 190

Asp Glu Leu Ala Ser Thr Lys Gln Lys Leu Glu Lys Ala Glu Asn Glu
                        195                 200                 205

Val Leu Ala Met Arg Lys Gln Ser Glu Gly Leu Thr Lys Glu Tyr Asp
                        210                 215                 220

Arg Leu Leu Glu Glu His Ala Lys Leu Gln Ala Ala Val Asp Gly Pro
        225                 230                 235                 240

Met Asp Lys Lys Glu Glu
                        245

<210> SEQ ID NO 20
<211> LENGTH: 63
<212> TYPE: PRT
<213> ORGANISM: Homo sapiens

<400> SEQUENCE: 20

Asp Val Gly Asn Ala Glu Val Lys Leu Glu Glu Glu Asn Arg Ser Leu
          1               5                  10                  15

Lys Ala Asp Leu Gln Lys Leu Lys Asp Glu Leu Ala Ser Thr Lys Gln
                         20                  25                  30

Lys Leu Glu Lys Ala Glu Asn Glu Val Leu Ala Met Arg Lys Gln Ser
                         35                  40                  45

Glu Gly Leu Thr Lys Glu Tyr Asp Arg Leu Leu Glu Glu His Ala
                 50                  55                  60

<210> SEQ ID NO 21
<211> LENGTH: 480
<212> TYPE: PRT
<213> ORGANISM: Homo sapiens

<400> SEQUENCE: 21

Met Ser Ala Glu Val Ile His Gln Val Glu Glu Ala Leu Asp Thr Asp
          1               5                  10                  15

Glu Lys Glu Met Leu Leu Phe Leu Cys Arg Asp Val Ala Ile Asp Val
                         20                  25                  30

Val Pro Pro Asn Val Arg Asp Leu Leu Asp Ile Leu Arg Glu Arg Gly
                         35                  40                  45

Lys Leu Ser Val Gly Asp Leu Ala Glu Leu Leu Tyr Arg Val Arg Arg
                 50                  55                  60

Phe Asp Leu Leu Lys Arg Ile Leu Lys Met Asp Arg Lys Ala Val Glu
         65                  70                  75                  80

Thr His Leu Leu Arg Asn Pro His Leu Val Ser Asp Tyr Arg Val Leu
                         85                  90                  95

Met Ala Glu Ile Gly Glu Asp Leu Asp Lys Ser Asp Val Ser Ser Leu
                        100                 105                 110

Ile Phe Leu Met Lys Asp Tyr Met Gly Arg Gly Lys Ile Ser Lys Glu
                        115                 120                 125

Lys Ser Phe Leu Asp Leu Val Val Glu Leu Glu Lys Leu Asn Leu Val
                        130                 135                 140

Ala Pro Asp Gln Leu Asp Leu Leu Glu Lys Cys Leu Lys Asn Ile His
        145                 150                 155                 160

Arg Ile Asp Leu Lys Thr Lys Ile Gln Lys Tyr Lys Gln Ser Val Gln
```

165                 170                 175
Gly Ala Gly Thr Ser Tyr Arg Asn Val Leu Gln Ala Ile Gln Lys
            180                 185                 190

Ser Leu Lys Asp Pro Ser Asn Asn Phe Arg Leu His Asn Gly Arg Ser
        195                 200                 205

Lys Glu Gln Arg Leu Lys Glu Gln Leu Gly Ala Gln Gln Glu Pro Val
    210                 215                 220

Lys Lys Ser Ile Gln Glu Ser Glu Ala Phe Leu Pro Gln Ser Ile Pro
225                 230                 235                 240

Glu Glu Arg Tyr Lys Met Lys Ser Lys Pro Leu Gly Ile Cys Leu Ile
                245                 250                 255

Ile Asp Cys Ile Gly Asn Glu Thr Glu Leu Leu Arg Asp Thr Phe Thr
            260                 265                 270

Ser Leu Gly Tyr Glu Val Gln Lys Phe Leu His Leu Ser Met His Gly
        275                 280                 285

Ile Ser Gln Ile Leu Gly Gln Phe Ala Cys Met Pro Glu His Arg Asp
    290                 295                 300

Tyr Asp Ser Phe Val Cys Val Leu Val Ser Arg Gly Gly Ser Gln Ser
305                 310                 315                 320

Val Tyr Gly Val Asp Gln Thr His Ser Gly Leu Pro Leu His His Ile
                325                 330                 335

Arg Arg Met Phe Met Gly Asp Ser Cys Pro Tyr Leu Ala Gly Lys Pro
            340                 345                 350

Lys Met Phe Phe Ile Gln Asn Tyr Val Val Ser Glu Gly Gln Leu Glu
        355                 360                 365

Asp Ser Ser Leu Leu Glu Val Asp Gly Pro Ala Met Lys Asn Val Glu
    370                 375                 380

Phe Lys Ala Gln Lys Arg Gly Leu Cys Thr Val His Arg Glu Ala Asp
385                 390                 395                 400

Phe Phe Trp Ser Leu Cys Thr Ala Asp Met Ser Leu Leu Glu Gln Ser
                405                 410                 415

His Ser Ser Pro Ser Leu Tyr Leu Gln Cys Leu Ser Gln Lys Leu Arg
            420                 425                 430

Gln Glu Arg Lys Arg Pro Leu Leu Asp Leu His Ile Glu Leu Asn Gly
        435                 440                 445

Tyr Met Tyr Asp Trp Asn Ser Arg Val Ser Ala Lys Glu Lys Tyr Tyr
    450                 455                 460

Val Trp Leu Gln His Thr Leu Arg Lys Lys Leu Ile Leu Ser Tyr Thr
465                 470                 475                 480

<210> SEQ ID NO 22
<211> LENGTH: 79
<212> TYPE: PRT
<213> ORGANISM: Homo sapiens

<400> SEQUENCE: 22

Ser Asp Tyr Arg Val Leu Met Ala Glu Ile Gly Glu Asp Leu Asp Lys
1               5                   10                  15

Ser Asp Val Ser Ser Leu Ile Phe Leu Met Lys Asp Tyr Met Gly Arg
            20                  25                  30

Gly Lys Ile Ser Lys Glu Lys Ser Phe Leu Asp Leu Val Val Glu Leu
        35                  40                  45

Glu Lys Leu Asn Leu Val Ala Pro Asp Gln Leu Asp Leu Leu Glu Lys
    50                  55                  60

```
Cys Leu Lys Asn Ile His Arg Ile Asp Leu Lys Thr Lys Ile Gln
 65                  70                  75
```

```
<210> SEQ ID NO 23
<211> LENGTH: 221
<212> TYPE: PRT
<213> ORGANISM: Homo sapiens

<400> SEQUENCE: 23
```

```
Met Ser Ala Glu Val Ile His Gln Val Glu Ala Leu Asp Thr Asp
 1               5                  10                  15

Glu Lys Glu Met Leu Leu Phe Leu Cys Arg Asp Val Ala Ile Asp Val
             20                  25                  30

Val Pro Pro Asn Val Arg Asp Leu Leu Asp Ile Leu Arg Glu Arg Gly
             35                  40                  45

Lys Leu Ser Val Gly Asp Leu Ala Glu Leu Leu Tyr Arg Val Arg Arg
 50                  55                  60

Phe Asp Leu Leu Lys Arg Ile Leu Lys Met Asp Arg Lys Ala Val Glu
 65                  70                  75                  80

Thr His Leu Leu Arg Asn Pro His Leu Val Ser Asp Tyr Arg Val Leu
                 85                  90                  95

Met Ala Glu Ile Gly Glu Asp Leu Asp Lys Ser Asp Val Ser Ser Leu
                100                 105                 110

Ile Phe Leu Met Lys Asp Tyr Met Gly Arg Gly Lys Ile Ser Lys Glu
                115                 120                 125

Lys Ser Phe Leu Asp Leu Val Val Glu Leu Glu Lys Leu Asn Leu Val
130                 135                 140

Ala Pro Asp Gln Leu Asp Leu Leu Glu Lys Cys Leu Lys Asn Ile His
145                 150                 155                 160

Arg Ile Asp Leu Lys Thr Lys Ile Gln Leu Tyr Lys Gln Ser Val Gln
                165                 170                 175

Gly Ala Gly Thr Ser Tyr Arg Asn Val Leu Gln Ala Ala Ile Gln Lys
                180                 185                 190

Ser Leu Lys Asp Pro Ser Asn Asn Phe Arg Met Ile Thr Pro Tyr Ala
                195                 200                 205

His Cys Pro Asp Leu Lys Ile Leu Gly Asn Cys Ser Met
                210                 215                 220
```

```
<210> SEQ ID NO 24
<211> LENGTH: 68
<212> TYPE: PRT
<213> ORGANISM: Homo sapiens

<400> SEQUENCE: 24
```

```
Met Ser Ala Glu Val Ile His Gln Val Glu Ala Leu Asp Thr Asp
 1               5                  10                  15

Glu Lys Glu Met Leu Leu Phe Leu Cys Arg Asp Val Ala Ile Asp Val
             20                  25                  30

Val Pro Pro Asn Val Arg Asp Leu Leu Asp Ile Leu Arg Glu Arg Gly
             35                  40                  45

Lys Leu Ser Val Gly Asp Leu Ala Glu Leu Leu Tyr Arg Val Arg Arg
 50                  55                  60

Phe Asp Leu Leu
 65
```

```
<210> SEQ ID NO 25
<211> LENGTH: 429
```

<212> TYPE: PRT
<213> ORGANISM: Homo sapiens

<400> SEQUENCE: 25

```
Met Thr Ala Ala Leu Ala Val Val Thr Thr Ser Gly Leu Glu Asp Gly
 1               5                  10                  15

Val Pro Arg Ser Arg Gly Glu Gly Thr Gly Glu Val Val Leu Glu Arg
            20                  25                  30

Gly Pro Gly Ala Ala Tyr His Met Phe Val Val Met Glu Asp Leu Val
        35                  40                  45

Glu Lys Leu Lys Leu Leu Arg Tyr Glu Glu Glu Phe Leu Arg Lys Ser
50                  55                  60

Asn Leu Lys Ala Pro Ser Arg His Tyr Phe Ala Leu Pro Thr Asn Pro
65                  70                  75                  80

Gly Glu Gln Phe Tyr Met Phe Cys Thr Leu Ala Ala Trp Leu Ile Asn
                85                  90                  95

Lys Ala Gly Arg Pro Phe Glu Gln Pro Gln Glu Tyr Asp Asp Pro Asn
            100                 105                 110

Ala Thr Ile Ser Asn Ile Leu Ser Glu Leu Arg Ser Phe Gly Arg Thr
        115                 120                 125

Ala Asp Phe Pro Pro Ser Lys Leu Lys Ser Gly Tyr Gly Glu His Val
130                 135                 140

Cys Tyr Val Leu Asp Cys Phe Ala Glu Ala Leu Lys Tyr Ile Gly Phe
145                 150                 155                 160

Phe Thr Trp Lys Arg Pro Ile Tyr Pro Val Glu Glu Leu Glu Glu Glu
                165                 170                 175

Ser Val Ala Glu Asp Ala Glu Leu Thr Leu Asn Lys Val Asp Glu Glu
            180                 185                 190

Phe Val Glu Glu Thr Asp Asn Glu Glu Asn Phe Ile Asp Leu Asn
        195                 200                 205

Asn Val Leu Lys Ala Gln Thr Tyr His Leu Asp Met Asn Glu Thr Ala
210                 215                 220

Lys Gln Glu Asp Ile Leu Glu Ser Thr Thr Asp Ala Ala Glu Trp Ser
225                 230                 235                 240

Leu Glu Val Glu Arg Val Leu Pro Gln Leu Lys Val Thr Ile Arg Thr
                245                 250                 255

Asp Asn Lys Asp Trp Arg Ile His Val Asp Gln Met His Gln His Arg
            260                 265                 270

Ser Gly Ile Glu Ser Ala Leu Lys Glu Thr Lys Gly Phe Leu Asp Lys
        275                 280                 285

Leu His Asn Glu Ile Thr Arg Thr Leu Glu Lys Ile Ser Ser Arg Glu
290                 295                 300

Lys Tyr Ile Asn Asn Gln Leu Glu Asn Leu Gln Glu Tyr Arg Ala
305                 310                 315                 320

Ala Gln Ala Gln Leu Ser Glu Ala Lys Glu Arg Tyr Gln Gln Gly Asn
                325                 330                 335

Gly Gly Val Thr Glu Arg Thr Arg Leu Leu Ser Glu Val Met Glu Glu
            340                 345                 350

Leu Glu Lys Val Lys Gln Glu Met Glu Glu Lys Gly Ser Ser Met Thr
        355                 360                 365

Asp Gly Ala Pro Leu Val Lys Ile Lys Gln Ser Leu Thr Lys Leu Lys
370                 375                 380

Gln Glu Thr Val Glu Met Asp Ile Arg Ile Gly Ile Val Glu His Thr
385                 390                 395                 400
```

```
Leu Leu Gln Ser Lys Leu Lys Glu Lys Ser Asn Met Thr Arg Asn Met
                405                 410                 415
His Ala Thr Val Ile Pro Glu Pro Ala Thr Gly Phe Tyr
            420                 425

<210> SEQ ID NO 26
<211> LENGTH: 92
<212> TYPE: PRT
<213> ORGANISM: Homo sapiens

<400> SEQUENCE: 26

Gly Asn Gly Gly Val Thr Glu Arg Thr Arg Leu Leu Ser Glu Val Met
1               5                   10                  15
Glu Glu Leu Glu Lys Val Lys Gln Glu Met Glu Glu Lys Gly Ser Ser
            20                  25                  30
Met Thr Asp Gly Ala Pro Leu Val Lys Ile Lys Gln Ser Leu Thr Lys
        35                  40                  45
Leu Lys Gln Glu Thr Val Glu Met Asp Ile Arg Ile Gly Ile Val Glu
    50                  55                  60
His Thr Leu Leu Gln Ser Lys Leu Lys Glu Lys Ser Asn Met Thr Arg
65                  70                  75                  80
Asn Met His Ala Thr Val Ile Pro Glu Pro Ala Thr
                85                  90

<210> SEQ ID NO 27
<211> LENGTH: 53
<212> TYPE: PRT
<213> ORGANISM: Homo sapiens

<400> SEQUENCE: 27

Lys Leu His Ser Ile Arg Asp Arg Asn Gly Thr His Leu Asp Ala Gly
1               5                   10                  15
Ala Leu Thr Thr Thr Phe Glu Glu Leu His Phe Glu Ile Lys Pro His
            20                  25                  30
His Asp Cys Thr Val Glu Gln Ile Tyr Glu Ile Leu Lys Ile Tyr Gln
        35                  40                  45
Leu Met Asp His Ser
    50

<210> SEQ ID NO 28
<211> LENGTH: 53
<212> TYPE: PRT
<213> ORGANISM: Homo sapiens

<400> SEQUENCE: 28

Lys Leu His Ser Ile Arg Asp Arg Asn Gly Thr His Leu Asp Ala Gly
1               5                   10                  15
Ala Leu Thr Thr Thr Phe Glu Glu Leu His Phe Glu Ile Lys Pro His
            20                  25                  30
Asp Asp Cys Thr Val Glu Gln Ile Tyr Glu Ile Leu Lys Ile Tyr Gln
        35                  40                  45
Leu Met Asp His Ser
    50

<210> SEQ ID NO 29
<211> LENGTH: 74
<212> TYPE: PRT
<213> ORGANISM: Homo sapiens
```

<400> SEQUENCE: 29

Ser Leu Phe Arg Asn Leu Leu Tyr Glu Leu Ser Glu Gly Ile Asp Ser
1               5                   10                  15

Glu Asn Leu Lys Asp Met Ile Phe Leu Leu Lys Asp Ser Leu Pro Lys
            20                  25                  30

Thr Glu Met Thr Ser Leu Ser Phe Leu Ala Phe Leu Glu Lys Gln Gly
        35                  40                  45

Lys Ile Asp Glu Asp Asn Leu Thr Cys Leu Glu Asp Leu Cys Lys Thr
    50                  55                  60

Val Val Pro Lys Leu Leu Arg Asn Ile Glu
65                  70

<210> SEQ ID NO 30
<211> LENGTH: 4
<212> TYPE: PRT
<213> ORGANISM: Homo sapiens

<400> SEQUENCE: 30

Lys Asp Glu Leu
 1

<210> SEQ ID NO 31
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 31
aaggtaccat caatgtccac g                                            21

<210> SEQ ID NO 32
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 32
aagttcagtg cccagctcta c                                            21

<210> SEQ ID NO 33
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 33
cgcttaccga ttcagaatgg                                              20

<210> SEQ ID NO 34
<211> LENGTH: 71
<212> TYPE: PRT
<213> ORGANISM: Homo sapiens

<400> SEQUENCE: 34

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu

```
                    35                  40                  45
Gln Glu Lys Arg Met Leu Glu Glu Ser Asn Leu Ser Phe Leu Lys Glu
    50                  55                  60

Leu Leu Phe Arg Ile Asn Arg
65                  70

<210> SEQ ID NO 35
<211> LENGTH: 71
<212> TYPE: PRT
<213> ORGANISM: Homo sapiens

<400> SEQUENCE: 35

Ser Ala Tyr Arg Val Met Leu Tyr Gln Ile Ser Glu Glu Val Ser Arg
  1               5                  10                  15

Ser Glu Leu Arg Ser Phe Lys Phe Leu Leu Gln Glu Glu Ile Ser Lys
                20                  25                  30

Cys Lys Leu Asp Asp Asp Met Asn Leu Leu Asp Ile Phe Ile Glu Met
                35                  40                  45

Glu Lys Arg Val Ile Leu Gly Glu Gly Lys Leu Asp Ile Leu Lys Arg
    50                  55                  60

Val Cys Ala Gln Ile Asn Lys
65                  70
```